(12) United States Patent
Ursin et al.

(10) Patent No.: US 7,622,632 B2
(45) Date of Patent: Nov. 24, 2009

(54) FATTY ACID DESATURASES FROM FUNGI

(75) Inventors: Virginia M. Ursin, Pawcatuck, CT (US); Toni Voelker, Davis, CA (US); Byron Froman, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 165 days.

(21) Appl. No.: 10/515,283

(22) PCT Filed: May 21, 2003

(86) PCT No.: PCT/US03/16144

§ 371 (c)(1), (2), (4) Date: Jan. 31, 2006

(87) PCT Pub. No.: WO03/099216

PCT Pub. Date: Dec. 4, 2003

(65) Prior Publication Data

US 2006/0156435 A1 Jul. 13, 2006

Related U.S. Application Data

(60) Provisional application No. 60/382,391, filed on May 22, 2002, provisional application No. 60/453,125, filed on Mar. 7, 2003.

(51) Int. Cl.
- *A01H 5/00* (2006.01)
- *C12N 15/82* (2006.01)
- *C07H 21/04* (2006.01)

(52) U.S. Cl. ............... 800/281; 800/298; 536/23.2
(58) Field of Classification Search ................. None
See application file for complete search history.

(56) References Cited

U.S. PATENT DOCUMENTS

| | | | |
|---|---|---|---|
| 5,434,283 A | 7/1995 | Wong et al. | 554/224 |
| 5,952,544 A | 9/1999 | Browse et al. | 800/295 |
| 5,968,809 A | 10/1999 | Knutzon et al. | 435/254.2 |
| 5,972,664 A | 10/1999 | Knutzon et al. | 435/136 |
| 6,063,947 A | 5/2000 | DeBonte et al. | 554/223 |
| 6,075,183 A | 6/2000 | Knutzon et al. | 800/281 |
| 6,459,018 B1 | 10/2002 | Knutzon | 800/281 |
| 2004/0039058 A1 | 2/2004 | Ursin et al. | 514/560 |
| 2005/0132441 A1 | 6/2005 | Damude et al. | 800/281 |
| 2005/0132442 A1 | 6/2005 | Yadav et al. | 800/281 |

FOREIGN PATENT DOCUMENTS

| | | |
|---|---|---|
| WO | WO 99/61602 | 12/1999 |
| WO | WO 99/64614 | 12/1999 |
| WO | WO 01/14538 | 3/2001 |

OTHER PUBLICATIONS

Brenner, SE, TIG 15(4): 132-133, Apr. 1999.*
Bork et al, TIG 12(10): 425-427, Oct. 1996.*
Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Kelder et al., "Expression of fungal desaturase genes in cultured mammalian cells," *Molecular and Cellular Biochemistry* 219:7-11, 2001.
Ursin, "Modification of plant lipids for human health: development of functional land-based omega-3 fatty acids," *Journal of Nutrition*, 33(12):4271-4274, 2003.
Arondel, "Map-based cloning of a gene controlling omega-3 fatty acid desaturation in *arabidopsis*," *Science*, 258(5086):1353-1355, 1992.
Huang, "Modification of liver fatty acid metabolism in mice by n-3 and n-6 $\Delta^6$-desaturase substrates and products," *Biochem. Biophys. Acta*, 1082:319, 1991.
Knutzon et al., "Modification of *brassica* seed oil by antisense expression of a stearoyl-acyl carrier protein desaturase gene," *Proc. Natl. Acad. Sci. USA*, 89(7):2624-2628, 1492.
Mantzioris et al., "Dietary substitution with an α-linolenic acid-rich vegetable oil increases eicosapentaenoic acid concentrations in tissues," *Am. J. Clin. Nutr.*, 59:1304, 1994.
Meesapyodsuk et al., "Characterization of the regiochemistry and cryptoregiochemistry of a *Caenorhabditis elegans* fatty acid desaturase (fat-1) expressed in *Saccharomyces cerevisiae*," *Biochemistry*, 39(39):11948-11954, 2000.
Reed et al., "Characterization of the *Brassica napus* extraplastidial linoleate desaturase by expression in *Saccharomyces cerevisiae*," *Plant Physiol.*, 122:715-720, 2000.
Yamazaki et al., "Comparison of the conversion rates of α-linolenic acid (18:3(n-3)) and stearidonic acid (18:4(n-3)) to longer polyunsaturated fatty acids in rats," *Biochem. Biophys. Acta*, 1123:18, 1992.
DeBlock et al., "Transformation of *Brassica napus* and *Brassica oleracea* using *Agrobacterium tumefaciens* and the expression of the bar and neo genes in the transgenic plants," *Plant Physiol.*, 91:694-701, 1989.

* cited by examiner

*Primary Examiner*—Elizabeth F McElwain
(74) *Attorney, Agent, or Firm*—Byron V. Olsen, Esq.; Sonnenschein Nath & Rosenthal LLP

(57) ABSTRACT

The invention relates generally to methods and compositions concerning fungal desaturase enzymes that modulate the number and location of double bonds in long chain polyunsaturated fatty acids (LC-PUFA's). In Particular, the invention relates to methods and compositions for improving omega-3 fatty acid profiles in plant products and parts using desaturase enzymes and nucleic acids encoding for such enzymes. In particular embodiments, the desaturase enzymes are fungal -15 desaturases. Also provided are improved canola oil compositions having SDA and maintaining beneficial oleic acid content.

32 Claims, 13 Drawing Sheets

FIG. 6

SEQUENCE LISTING

```
<160> NUMBER OF SEQ ID NOS: 43

<210> SEQ ID NO 1
<211> LENGTH: 2125
<212> TYPE: DNA
<213> ORGANISM: Neurospora crassa

<400> SEQUENCE: 1
gagcctcttc gttttcctcc catcaccaat ttctttttct gaaagaggtg tgtcgagtgt      60
gagttgaacc tcaggtcttc ttccacacta cctctaccct cctcttccta ccctctttct     120
tcacttcttg gatatcctca agaaatatca ccacacccaa caaacatgac ggtcaccacc     180
cgcagccaca aggccgcggc cgccaccgag cccgaggttg tcagcaccgg cgttgacgcc     240
gtctctgctg ctgctccctc ctcctcctcc tcctcttcca gccaaaagtc ggccgagccc     300
atcgaatacc ccgacatcaa gaccatccgc gacgccatcc ccgaccactg cttccgcccg     360
cgcgtctgga tctccatggc ctacttcatc cgcgacttcg ccatggcctt tggcctcggc     420
tacctcgcct ggcagtacat cccctgatc gcctccacc cgctccgcta cggcgcctgg      480
gctctgtacg gctacctcca gggtctcgtc tgcacgggca tctggattct ggcgcacgag     540
tgcggccacg gcgccttctc gaggcacacg tggttcaaca acgtcatggg gtggattggc     600
cactccttcc tcttggtccc ttacttcagc tggaagttca gccaccatcg ccaccatcgc     660
ttcaccggcc acatggagaa ggacatggcg tttgtgcctg ccaccgaggc tgatcgcaac     720
```

-continued

```
cagaggaagc tggccaactt gtacatggac aaggagacgg ccgagatgtt tgaggatgtg    780
cccattgtcc agctcgtcaa gctcatcgcc caccagctgg ccggctggca gatgtacctc    840
ctcctcaacg tctccgccgg taagggcagc aagcagtggg agactggcaa gggcggcatg    900
ggctggttga gggttagcca ctttgagcct tcctctgctg tgttccgcaa ctccgaggcc    960
atctacattg ccctgtccga tcttggtctc atgatcatgg gctatatcct ctaccaggcc   1020
gcgcaggttg ttggctggca gatggtaggt ctgctgtact ccagcagta cttctgggtt   1080 caccattggt tgggtaagtt gtctctcgcc catttcgcct ctgtctggtg gttcttgtga   1140
tctttgtgga attagcgcac taactctcgc tccctctcaa acagtcgcc atcacttacc    1200 tccaccacac ccacgaggaa gtccaccact ttgacgccga ctcgtggacc ttcgtcaagg   1260
gcgctctcgc caccgtcgac cgcgattttg gcttcattgg caagcacctc ttccacaaca   1320
ttatcgacca ccacgtcgtc caccacttgt tcccgtaagt cttcagatca gatatccctg   1380
ctattttctc atttaaaacc atcccctcaa tgtccctcgc taacgcccca aatcctgcac   1440
agtcgcatcc ccttctacta cgccgaagaa gccaccaact cgatccgccc catgctcggc   1500
cccctctacc accgcgacga ccgctccttc atgggccagc tgtggtacaa cttcacccac   1560
tgcaagtggg tcgttccgga ccccaggtc ccggcgcgc ttatttgggc gcacaccgtt    1620
cagagcaccc agtaagcagt tctttctgc ttcctggggc actctgagga ggctacctac    1680
ctacctaggt actcgagtgc tggctgctgc cctggtttag tgctacctac ttcggtagct   1740
ctaaccggta ccagaagaac gatgttggaa aaaaggaggg agaaagactg gaagaaaagg   1800
aaaacaaaga aatctcaact cttcttcatg attgatggat ctgtgccacg ttctgattgg   1860
ttcggtcggt caaaaggcgt acataacggt caccattgaa aggtctggat aactcggtac   1920
ctggaatttc acatcaaaca agtgatagac gagagagaga gtctggtaga atagaggtat   1980
ggtagatctg gaagctatta gacttactag agctatagat agacaaagag gatagagcga   2040
gggtatgtgt gtgtagaggt agagatgcat catagaaggg agggcatgca tgcatgattg   2100
aagaaccaaa agaatgatac ccacc                                          2125
```

<210> SEQ ID NO 2
<211> LENGTH: 1290
<212> TYPE: DNA
<213> ORGANISM: Neurospora crassa
<220> FEATURE:
<221> NAME/KEY: CDS
<222> LOCATION: (1)..(1290)

<400> SEQUENCE: 2

```
atg acg gtc acc acc cgc agc cac aag gcc gcg gcc gcc acc gag ccc     48
Met Thr Val Thr Thr Arg Ser His Lys Ala Ala Ala Ala Thr Glu Pro
 1               5                  10                  15 gag gtt gtc agc acc ggc gtt gac gcc gtc tct gct gct gct ccc tcc     96
Glu Val Val Ser Thr Gly Val Asp Ala Val Ser Ala Ala Ala Pro Ser
             20                  25                  30 tcc tcc tcc tcc tct tcc agc caa aag tcg gcc gag ccc atc gaa tac    144
Ser Ser Ser Ser Ser Ser Ser Gln Lys Ser Ala Glu Pro Ile Glu Tyr
         35                  40                  45 ccc gac atc aag acc atc cgc gac gcc atc ccc gac cac tgc ttc cgc    192
Pro Asp Ile Lys Thr Ile Arg Asp Ala Ile Pro Asp His Cys Phe Arg
     50                  55                  60 ccg cgc gtc tgg atc tcc atg gcc tac ttc atc cgc gac ttc gcc atg    240
Pro Arg Val Trp Ile Ser Met Ala Tyr Phe Ile Arg Asp Phe Ala Met
 65                  70                  75                  80
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | ttt | ggc | ctc | ggc | tac | ctc | gcc | tgg | cag | tac | atc | ccc | ctg | atc | gcc | 288  |
| Ala | Phe | Gly | Leu | Gly | Tyr | Leu | Ala | Trp | Gln | Tyr | Ile | Pro | Leu | Ile | Ala |      |
|     |     |     |     | 85  |     |     |     |     | 90  |     |     |     |     | 95  |     |      |
| tcc | acc | ccg | ctc | cgc | tac | ggc | gcc | tgg | gct | ctg | tac | ggc | tac | ctc | cag | 336  |
| Ser | Thr | Pro | Leu | Arg | Tyr | Gly | Ala | Trp | Ala | Leu | Tyr | Gly | Tyr | Leu | Gln |      |
|     |     |     | 100 |     |     |     |     | 105 |     |     |     |     | 110 |     |     |      |
| ggt | ctc | gtc | tgc | acg | ggc | atc | tgg | att | ctg | gcg | cac | gag | tgc | ggc | cac | 384  |
| Gly | Leu | Val | Cys | Thr | Gly | Ile | Trp | Ile | Leu | Ala | His | Glu | Cys | Gly | His |      |
|     |     | 115 |     |     |     |     | 120 |     |     |     |     | 125 |     |     |     |      |
| ggc | gcc | ttc | tcg | agg | cac | acg | tgg | ttc | aac | aac | gtc | atg | ggg | tgg | att | 432  |
| Gly | Ala | Phe | Ser | Arg | His | Thr | Trp | Phe | Asn | Asn | Val | Met | Gly | Trp | Ile |      |
| 130 |     |     |     |     | 135 |     |     |     |     | 140 |     |     |     |     |     |      |
| ggc | cac | tcc | ttc | ctc | ttg | gtc | cct | tac | ttc | agc | tgg | aag | ttc | agc | cac | 480  |
| Gly | His | Ser | Phe | Leu | Leu | Val | Pro | Tyr | Phe | Ser | Trp | Lys | Phe | Ser | His |      |
| 145 |     |     |     | 150 |     |     |     |     | 155 |     |     |     |     | 160 |     |      |
| cat | cgc | cac | cat | cgc | ttc | acc | ggc | cac | atg | gag | aag | gac | atg | gcg | ttt | 528  |
| His | Arg | His | His | Arg | Phe | Thr | Gly | His | Met | Glu | Lys | Asp | Met | Ala | Phe |      |
|     |     |     | 165 |     |     |     |     | 170 |     |     |     |     | 175 |     |     |      |
| gtg | cct | gcc | acc | gag | gct | gat | cgc | aac | cag | agg | aag | ctg | gcc | aac | ttg | 576  |
| Val | Pro | Ala | Thr | Glu | Ala | Asp | Arg | Asn | Gln | Arg | Lys | Leu | Ala | Asn | Leu |      |
|     |     | 180 |     |     |     |     | 185 |     |     |     |     | 190 |     |     |     |      |
| tac | atg | gac | aag | gag | acg | gcc | gag | atg | ttt | gag | gat | gtg | ccc | att | gtc | 624  |
| Tyr | Met | Asp | Lys | Glu | Thr | Ala | Glu | Met | Phe | Glu | Asp | Val | Pro | Ile | Val |      |
|     |     |     | 195 |     |     |     |     | 200 |     |     |     |     | 205 |     |     |      |
| cag | ctc | gtc | aag | ctc | atc | gcc | cac | cag | ctg | gcc | ggc | tgg | cag | atg | tac | 672  |
| Gln | Leu | Val | Lys | Leu | Ile | Ala | His | Gln | Leu | Ala | Gly | Trp | Gln | Met | Tyr |      |
|     | 210 |     |     |     |     | 215 |     |     |     |     | 220 |     |     |     |     |      |
| ctc | ctc | ttc | aac | gtc | tcc | gcc | ggt | aag | ggc | agc | aag | cag | tgg | gag | act | 720  |
| Leu | Leu | Phe | Asn | Val | Ser | Ala | Gly | Lys | Gly | Ser | Lys | Gln | Trp | Glu | Thr |      |
| 225 |     |     |     | 230 |     |     |     |     | 235 |     |     |     |     | 240 |     |      |
| ggc | aag | ggc | ggc | atg | ggc | tgg | ttg | agg | gtt | agc | cac | ttt | gag | cct | tcc | 768  |
| Gly | Lys | Gly | Gly | Met | Gly | Trp | Leu | Arg | Val | Ser | His | Phe | Glu | Pro | Ser |      |
|     |     |     | 245 |     |     |     |     | 250 |     |     |     |     | 255 |     |     |      |
| tct | gct | gtg | ttc | cgc | aac | tcc | gag | gcc | atc | tac | att | gcc | ctg | tcc | gat | 816  |
| Ser | Ala | Val | Phe | Arg | Asn | Ser | Glu | Ala | Ile | Tyr | Ile | Ala | Leu | Ser | Asp |      |
|     |     | 260 |     |     |     |     | 265 |     |     |     |     | 270 |     |     |     |      |
| ctt | ggt | ctc | atg | atc | atg | ggc | tat | atc | ctc | tac | cag | gcc | gcg | cag | gtt | 864  |
| Leu | Gly | Leu | Met | Ile | Met | Gly | Tyr | Ile | Leu | Tyr | Gln | Ala | Ala | Gln | Val |      |
|     |     | 275 |     |     |     |     | 280 |     |     |     |     | 285 |     |     |     |      |
| gtt | ggc | tgg | cag | atg | gta | ggt | ctg | ctg | tac | ttc | cag | cag | tac | ttc | tgg | 912  |
| Val | Gly | Trp | Gln | Met | Val | Gly | Leu | Leu | Tyr | Phe | Gln | Gln | Tyr | Phe | Trp |      |
|     | 290 |     |     |     |     | 295 |     |     |     |     | 300 |     |     |     |     |      |
| gtt | cac | cat | tgg | ttg | gtc | gcc | atc | act | tac | ctc | cac | cac | acc | cac | gag | 960  |
| Val | His | His | Trp | Leu | Val | Ala | Ile | Thr | Tyr | Leu | His | His | Thr | His | Glu |      |
| 305 |     |     |     | 310 |     |     |     |     | 315 |     |     |     |     | 320 |     |      |
| gaa | gtc | cac | cac | ttt | gac | gcc | gac | tcg | tgg | acc | ttc | gtc | aag | ggc | gct | 1008 |
| Glu | Val | His | His | Phe | Asp | Ala | Asp | Ser | Trp | Thr | Phe | Val | Lys | Gly | Ala |      |
|     |     |     | 325 |     |     |     |     | 330 |     |     |     |     | 335 |     |     |      |
| ctc | gcc | acc | gtc | gac | cgc | gat | ttt | ggc | ttc | att | ggc | aag | cac | ctc | ttc | 1056 |
| Leu | Ala | Thr | Val | Asp | Arg | Asp | Phe | Gly | Phe | Ile | Gly | Lys | His | Leu | Phe |      |
|     |     |     | 340 |     |     |     |     | 345 |     |     |     |     | 350 |     |     |      |
| cac | aac | att | atc | gac | cac | cac | gtc | gtc | cac | cac | ttg | ttc | cct | cgc | atc | 1104 |
| His | Asn | Ile | Ile | Asp | His | His | Val | Val | His | His | Leu | Phe | Pro | Arg | Ile |      |
|     |     |     | 355 |     |     |     |     | 360 |     |     |     |     | 365 |     |     |      |
| ccc | ttc | tac | tac | gcc | gaa | gaa | gcc | acc | aac | tcg | atc | cgc | ccc | atg | ctc | 1152 |
| Pro | Phe | Tyr | Tyr | Ala | Glu | Glu | Ala | Thr | Asn | Ser | Ile | Arg | Pro | Met | Leu |      |
|     | 370 |     |     |     |     | 375 |     |     |     |     | 380 |     |     |     |     |      |
| ggc | ccc | ctc | tac | cac | cgc | gac | gac | cgc | tcc | ttc | atg | ggc | cag | ctg | tgg | 1200 |
| Gly | Pro | Leu | Tyr | His | Arg | Asp | Asp | Arg | Ser | Phe | Met | Gly | Gln | Leu | Trp |      |

-continued

```
                385                 390                 395                 400
tac aac ttc acc cac tgc aag tgg gtc gtt ccg gac ccc cag gtc ccc      1248
Tyr Asn Phe Thr His Cys Lys Trp Val Val Pro Asp Pro Gln Val Pro
                405                 410                 415 ggc gcg ctt att tgg gcg cac acc gtt cag agc acc cag taa              1290
Gly Ala Leu Ile Trp Ala His Thr Val Gln Ser Thr Gln
        420                 425                 430
```

<210> SEQ ID NO 3
<211> LENGTH: 429
<212> TYPE: PRT
<213> ORGANISM: Neurospora crassa

<400> SEQUENCE: 3

Met Thr Val Thr Thr Arg Ser His Lys Ala Ala Ala Thr Glu Pro
 1               5                  10                  15

Glu Val Val Ser Thr Gly Val Asp Ala Val Ser Ala Ala Pro Ser
                20                  25                  30

Ser Ser Ser Ser Ser Ser Gln Lys Ser Ala Glu Pro Ile Glu Tyr
            35                  40                  45

Pro Asp Ile Lys Thr Ile Arg Asp Ala Ile Pro Asp His Cys Phe Arg
 50                  55                  60

Pro Arg Val Trp Ile Ser Met Ala Tyr Phe Ile Arg Asp Phe Ala Met
65                  70                  75                  80

Ala Phe Gly Leu Gly Tyr Leu Ala Trp Gln Tyr Ile Pro Leu Ile Ala
                85                  90                  95

Ser Thr Pro Leu Arg Tyr Gly Ala Trp Ala Leu Tyr Gly Tyr Leu Gln
            100                 105                 110

Gly Leu Val Cys Thr Gly Ile Trp Ile Leu Ala His Glu Cys Gly His
        115                 120                 125

Gly Ala Phe Ser Arg His Thr Trp Phe Asn Asn Val Met Gly Trp Ile
    130                 135                 140

Gly His Ser Phe Leu Leu Val Pro Tyr Phe Ser Trp Lys Phe Ser His
145                 150                 155                 160

His Arg His His Arg Phe Thr Gly His Met Glu Lys Asp Met Ala Phe
                165                 170                 175

Val Pro Ala Thr Glu Ala Asp Arg Asn Gln Arg Lys Leu Ala Asn Leu
            180                 185                 190

Tyr Met Asp Lys Glu Thr Ala Glu Met Phe Glu Asp Val Pro Ile Val
        195                 200                 205

Gln Leu Val Lys Leu Ile Ala His Gln Leu Ala Gly Trp Gln Met Tyr
    210                 215                 220

Leu Leu Phe Asn Val Ser Ala Gly Lys Gly Ser Lys Gln Trp Glu Thr
225                 230                 235                 240

Gly Lys Gly Gly Met Gly Trp Leu Arg Val Ser His Phe Glu Pro Ser
                245                 250                 255

Ser Ala Val Phe Arg Asn Ser Glu Ala Ile Tyr Ile Ala Leu Ser Asp
            260                 265                 270

Leu Gly Leu Met Ile Met Gly Tyr Ile Leu Tyr Gln Ala Ala Gln Val
        275                 280                 285

Val Gly Trp Gln Met Val Gly Leu Leu Tyr Phe Gln Gln Tyr Phe Trp
    290                 295                 300

Val His His Trp Leu Val Ala Ile Thr Tyr Leu His His Thr His Glu
305                 310                 315                 320

Glu Val His His Phe Asp Ala Asp Ser Trp Thr Phe Val Lys Gly Ala

```
                              325                 330                 335
Leu Ala Thr Val Asp Arg Asp Phe Gly Phe Ile Gly Lys His Leu Phe
            340                 345                 350

His Asn Ile Ile Asp His His Val Val His His Leu Phe Pro Arg Ile
            355                 360                 365

Pro Phe Tyr Tyr Ala Glu Glu Ala Thr Asn Ser Ile Arg Pro Met Leu
            370                 375                 380

Gly Pro Leu Tyr His Arg Asp Asp Arg Ser Phe Met Gly Gln Leu Trp
385                 390                 395                 400

Tyr Asn Phe Thr His Cys Lys Trp Val Val Pro Asp Pro Gln Val Pro
            405                 410                 415

Gly Ala Leu Ile Trp Ala His Thr Val Gln Ser Thr Gln
            420                 425

<210> SEQ ID NO 4
<211> LENGTH: 1206
<212> TYPE: DNA
<213> ORGANISM: Aspergillus nidulans
<220> FEATURE:
<221> NAME/KEY: CDS
<222> LOCATION: (1)..(1206)

<400> SEQUENCE: 4 atg gct gca act gca aca acc cta gca gag att gaa aag aaa aaa gaa       48
Met Ala Ala Thr Ala Thr Thr Leu Ala Glu Ile Glu Lys Lys Lys Glu
 1               5                  10                  15 gaa ata act ctg cag aca atc aaa aat gcg att ccc aaa cac tgc ttc       96
Glu Ile Thr Leu Gln Thr Ile Lys Asn Ala Ile Pro Lys His Cys Phe
                20                  25                  30 aac cgc tct ctc ctc att tcc tct gcc tac gtc gtc cgc gat ctc ctc      144
Asn Arg Ser Leu Leu Ile Ser Ser Ala Tyr Val Val Arg Asp Leu Leu
            35                  40                  45 tac gcc tcc gtc ctc ttc tac ttt gcc ctg cac att gac acc ctc ttt      192
Tyr Ala Ser Val Leu Phe Tyr Phe Ala Leu His Ile Asp Thr Leu Phe
        50                  55                  60 tcc tcg caa ctc ctc cgc atc ctc gcc tgg acc gcc tac ggt ttc atg      240
Ser Ser Gln Leu Leu Arg Ile Leu Ala Trp Thr Ala Tyr Gly Phe Met
 65                  70                  75                  80 caa ggc tgc gtc ggc acc gga atc tgg atc ctc gca cac gaa tgc ggc      288
Gln Gly Cys Val Gly Thr Gly Ile Trp Ile Leu Ala His Glu Cys Gly
                85                  90                  95 cat gga gct ttc tcc cca tac caa acg tgg aac gat gtc gtc gga tgg      336
His Gly Ala Phe Ser Pro Tyr Gln Thr Trp Asn Asp Val Val Gly Trp
            100                 105                 110 aca ttg cac tcc ctc ctg atg gtc ccg tat ttc agc tgg aag atc acg      384
Thr Leu His Ser Leu Leu Met Val Pro Tyr Phe Ser Trp Lys Ile Thr
        115                 120                 125 cac gct cga cac cac cgg tac aca aac aac aca gag cga gat aca gca      432
His Ala Arg His His Arg Tyr Thr Asn Asn Thr Glu Arg Asp Thr Ala
    130                 135                 140 ttt gtc ccc tgg aca gag aag gaa tac gac act cgc cgc gct tac ttc      480
Phe Val Pro Trp Thr Glu Lys Glu Tyr Asp Thr Arg Pro Arg Tyr Phe
145                 150                 155                 160 cct gcc tgg ttt gag atg ttt gag gac acg ccc gtc tac aac ctt att      528
Pro Ala Trp Phe Glu Met Phe Glu Asp Thr Pro Val Tyr Asn Leu Ile
                165                 170                 175 agc cta ctg gcg cat cag atc gca gga tgg cag atg tat ctc tgt ttt      576
Ser Leu Leu Ala His Gln Ile Ala Gly Trp Gln Met Tyr Leu Cys Phe
            180                 185                 190
```

-continued

```
tac gtt agc gcc ggc gca aag agt aag cct gta ccg cag gga aaa cag      624
Tyr Val Ser Ala Gly Ala Lys Ser Lys Pro Val Pro Gln Gly Lys Gln
        195                 200                 205 agc ggg tgg ttt gga ggc cag cag agc gcc agc cac ttt gat ccg ggc      672
Ser Gly Trp Phe Gly Gly Gln Gln Ser Ala Ser His Phe Asp Pro Gly
    210                 215                 220 agt tcg ctg tgg acg gaa aac cag cgg cat ctg att gcg att tcg gac      720
Ser Ser Leu Trp Thr Glu Asn Gln Arg His Leu Ile Ala Ile Ser Asp
225                 230                 235                 240 ctg ggg ttg ctg ctt gtt gcg gcg gca aat tgg tac ctt gcg cag caa      768
Leu Gly Leu Leu Leu Val Ala Ala Ala Asn Trp Tyr Leu Ala Gln Gln
                245                 250                 255 gtg ggc gtg ctc cgc atg gtg ctg atc tat gtt gtg ccg tac ttc tgg      816
Val Gly Val Leu Arg Met Val Leu Ile Tyr Val Val Pro Tyr Phe Trp
            260                 265                 270 gtg cac cat tgg ctt gtg gcg atc acg tac ctc cac cac aca cac ccc      864
Val His His Trp Leu Val Ala Ile Thr Tyr Leu His His Thr His Pro
        275                 280                 285 tcg atc ccg cac tac act gat agc acc tgg acg ttc acc aaa ggc gct      912
Ser Ile Pro His Tyr Thr Asp Ser Thr Trp Thr Phe Thr Lys Gly Ala
    290                 295                 300 ctg tcc acc gtc gac cgc gac ttc ggt ttc atc ggg cgg cat ttc ttc      960
Leu Ser Thr Val Asp Arg Asp Phe Gly Phe Ile Gly Arg His Phe Phe
305                 310                 315                 320 cac cat atc att gac cac cat gtc gtg cat cac ttg ttt aac cgg atc     1008
His His Ile Ile Asp His His Val Val His His Leu Phe Asn Arg Ile
                325                 330                 335 ccg ttc tac cat gcc gag gag gcg act aat gcc att att ccc gta ctc     1056
Pro Phe Tyr His Ala Glu Glu Ala Thr Asn Ala Ile Ile Pro Val Leu
            340                 345                 350 ggg gac atg tat cat cgc gaa gag acc ggc ttc ttg tgg agt tta atg     1104
Gly Asp Met Tyr His Arg Glu Glu Thr Gly Phe Leu Trp Ser Leu Met
        355                 360                 365 gag acg tac aag aac tgt cgg ttt gta ggc gtt gaa aat gat gtt gga     1152
Glu Thr Tyr Lys Asn Cys Arg Phe Val Gly Val Glu Asn Asp Val Gly
    370                 375                 380 aag gag ggc gtt ttg cat tgg gtt ttt gag gag aag aag ggt gcc aaa     1200
Lys Glu Gly Val Leu His Trp Val Phe Glu Glu Lys Lys Gly Ala Lys
385                 390                 395                 400 gcg gaa                                                              1206
Ala

<210> SEQ ID NO 5
<211> LENGTH: 401
<212> TYPE: PRT
<213> ORGANISM: Aspergillus nidulans

<400> SEQUENCE: 5

Met Ala Ala Thr Ala Thr Thr Leu Ala Glu Ile Glu Lys Lys Lys Glu
1               5                   10                  15

Glu Ile Thr Leu Gln Thr Ile Lys Asn Ala Ile Pro Lys His Cys Phe
            20                  25                  30

Asn Arg Ser Leu Leu Ile Ser Ser Ala Tyr Val Val Arg Asp Leu Leu
        35                  40                  45

Tyr Ala Ser Val Leu Phe Tyr Phe Ala Leu His Ile Asp Thr Leu Phe
    50                  55                  60

Ser Ser Gln Leu Leu Arg Ile Leu Ala Trp Thr Ala Tyr Gly Phe Met
65                  70                  75                  80

Gln Gly Cys Val Gly Thr Gly Ile Trp Ile Leu Ala His Glu Cys Gly
```

-continued

```
                    85                  90                  95
His Gly Ala Phe Ser Pro Tyr Gln Thr Trp Asn Asp Val Val Gly Trp
            100                 105                 110
Thr Leu His Ser Leu Leu Met Val Pro Tyr Phe Ser Trp Lys Ile Thr
            115                 120                 125
His Ala Arg His His Arg Tyr Thr Asn Asn Thr Glu Arg Asp Thr Ala
            130                 135                 140
Phe Val Pro Trp Thr Glu Lys Glu Tyr Asp Thr Arg Pro Arg Tyr Phe
145                 150                 155                 160
Pro Ala Trp Phe Glu Met Phe Glu Asp Thr Pro Val Tyr Asn Leu Ile
                165                 170                 175
Ser Leu Leu Ala His Gln Ile Ala Gly Trp Gln Met Tyr Leu Cys Phe
                180                 185                 190
Tyr Val Ser Ala Gly Ala Lys Ser Lys Pro Val Pro Gln Gly Lys Gln
                195                 200                 205
Ser Gly Trp Phe Gly Gly Gln Gln Ser Ala Ser His Phe Asp Pro Gly
                210                 215                 220
Ser Ser Leu Trp Thr Glu Asn Gln Arg His Leu Ile Ala Ile Ser Asp
225                 230                 235                 240
Leu Gly Leu Leu Leu Val Ala Ala Ala Asn Trp Tyr Leu Ala Gln Gln
                245                 250                 255
Val Gly Val Leu Arg Met Val Leu Ile Tyr Val Val Pro Tyr Phe Trp
                260                 265                 270
Val His His Trp Leu Val Ala Ile Thr Tyr Leu His His Thr His Pro
                275                 280                 285
Ser Ile Pro His Tyr Thr Asp Ser Thr Trp Thr Phe Thr Lys Gly Ala
                290                 295                 300
Leu Ser Thr Val Asp Arg Asp Phe Gly Phe Ile Gly Arg His Phe Phe
305                 310                 315                 320
His His Ile Ile Asp His His Val Val His Leu Phe Asn Arg Ile
                325                 330                 335
Pro Phe Tyr His Ala Glu Glu Ala Thr Asn Ala Ile Ile Pro Val Leu
                340                 345                 350
Gly Asp Met Tyr His Arg Glu Glu Thr Gly Phe Leu Trp Ser Leu Met
                355                 360                 365
Glu Thr Tyr Lys Asn Cys Arg Phe Val Gly Val Glu Asn Asp Val Gly
                370                 375                 380
Lys Glu Gly Val Leu His Trp Val Phe Glu Glu Lys Lys Gly Ala Lys
385                 390                 395                 400
Ala
```

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

```
Trp Ile Leu Ala His Glu Cys Gly His Gly Ala Ser Phe
1               5                   10
```

<210> SEQ ID NO 7
<211> LENGTH: 7
<212> TYPE: PRT

```
<213> ORGANISM: Artificial Sequence
<220> FEATURE:
<223> OTHER INFORMATION: Description of Artificial Sequence: Synthetic
      Peptide

<400> SEQUENCE: 7

Leu Ala His Glu Cys Gly His
 1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

His Ser Phe Leu Leu Val Pro Tyr Phe Ser Trp Lys
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Leu Leu Val Pro Tyr Phe Ser Trp Lys
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

His His Arg His His Arg Phe Thr Thr
 1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Trp Val His His Trp Leu Val Ala Ile Thr Tyr Leu His His Thr His
 1               5                  10                  15

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Ala Ile Thr Tyr Leu His Gln His Thr
 1               5
```

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Gly Ala Leu Ala Thr Val Asp Arg
  1               5

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (8)
<223> OTHER INFORMATION: X = anything

<400> SEQUENCE: 14

His Val Val His His Leu Phe Xaa Arg Ile Pro Phe Tyr
  1               5                  10

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
aagatggcgt ccgtctcctc tgcccttccc                                        30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ttagttggtt ttgggagct tggcaggctt g                                       31

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gcggccgcaa catgacggtc accacccgca gcca                                   34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic

```
            Primer

<400> SEQUENCE: 18
cctgcaggtt actgggtgct ctgaacggtg tgcg                              34

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

His His Arg His His Arg Tyr Thr Thr
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

His Ala Arg His His Arg Phe Thr Thr
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

His Ala Arg His His Arg Tyr Thr Thr
 1               5

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Trp Val His His Trp Leu Val Ala Ile Thr Tyr Leu Gln His Thr
 1               5                  10                  15

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
aatatggctg caactgcaac aaccc                                       25

<210> SEQ ID NO 24
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 24
ttccgctttg gcacccttct tc                                              22

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
gtcgacacca tggcctctac cactgctctc                                      30

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ctgcagtgcc ttgagcttca ttggtggtgt a                                    31

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (7)..(22)
<223> OTHER INFORMATION: N = A, C, G, or T/U
<220> FEATURE:
<223> OTHER INFORMATION: Description of Artificial Sequence: Synthetic
      Primer

<400> SEQUENCE: 27
gccrtgnccr caytcrtgng cnagdat                                         27

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
acgatgactc tcgattacac aagtcacccg                                      30

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
```

```
gtcgacacga tgactctcga ttacacaagt cacc                                34
```

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30

```
ctgcagaatg cttgagctat cagcagatcc caa                                 33
```

<210> SEQ ID NO 31
<211> LENGTH: 1428
<212> TYPE: DNA
<213> ORGANISM: Botrytis cinerea

<400> SEQUENCE: 31

```
atggcctcta ccactgctct cccaaagcgc accgccgttc aaagaacggt gacctcctcc    60
actgccgaat cagctccctc gacagctgcc ggttccccca atgataccccc aagacaatcc   120 ccctcgtcta cttctctgtc atctatgtca tctctaggcg aagatgttaa gagcaccaag   180
ccatatggca aactcatcga tacttacgga acgaatttg agcttccaga ttataccgtc    240
aatgacatcc gtaacgcaat tccaaagcat tgttacgagc gatctggagt aagggggttg   300
gcttatgttg ctcgcgatat tgccagctta gccaccacat tcttcctctt caacaaatac   360
cttacaccag aaaacgttcc ctcaactyca gcgcgcgctg tgctgtgggc tttatacacc   420
gttgttcagg gtttgtttgg tactggtctc tgggttcttg ctcatgagtg tggccatcaa   480
tctttctcga cttcaaaggt cttgaacgat acaactggat ggatctgcca ctctgctctt   540
ctcgtcccat acttttcatg gaagatctct cacggcaagc atcacaaagc tactggcaac   600
atggagcgtg atatggtttt cgttccaaag accgtcaag attatgctac ccgcgtcggc    660
aagttcgttc atgagcttca cgagctcacc gaggagactc caatcgcaac tcttattcac   720
tccatcggac aacaacttgc tggctggcct ttgtacttat tcatgaacgt caccggtcac   780
aacaaccatg agcgtcaaca tgagggtcgt ggaaagggta aggtcaacag tttctggacc   840
gtcagtcact tcaacccagc cagtcctctt tatgaagcta aggatgccaa attgatcttg   900
ttgagtgatc tcggtatcgc catcaccgcc gctgtcctta tcatgcttag caagacatac   960
ggattttaca acatggctat ctggtacttc attccatacc tctgggtaaa ccactggctt  1020
gttgctatca ccttcctcca acacaccgac ccaactcttc ctcactactc tggcgagagc  1080
tggaactatg ttcgtggagc cgcagcaacc atcgatcgtg aattcggatt catcggacgc  1140
actcttcttc acggtatcat cgagacccac gttcttcacc actacgtcag caccattcct  1200
ttctaccacg ccgatgaggc taccgaggcc atcaagccta tcatgggtcg tcactacaga  1260
gccgatgttc gaggcggatc ccttggattt ttgaagagct tgtggtccag cgctcgttgg  1320
tgccagtggg tcgagccatc tgagggtgct gaaggtgagg caagaaggt attcttcttc   1380 cgtaaccgca atggactcgg tacaccacca atgaagctca aggcataa               1428
```

<210> SEQ ID NO 32
<211> LENGTH: 475
<212> TYPE: PRT
<213> ORGANISM: Botrytis cinerea
<220> FEATURE:
<221> NAME/KEY: MOD_RES
<222> LOCATION: (130)

<223> OTHER INFORMATION: X = anything

<400> SEQUENCE: 32

```
Met Ala Ser Thr Thr Ala Leu Pro Lys Arg Thr Ala Val Gln Arg Thr
 1               5                  10                  15

Val Thr Ser Ser Thr Ala Glu Ser Ala Pro Ser Thr Ala Ala Gly Ser
            20                  25                  30

Pro Asn Asp Thr Pro Arg Gln Ser Pro Ser Ser Thr Ser Leu Ser Ser
        35                  40                  45

Met Ser Ser Leu Gly Glu Asp Val Lys Ser Thr Lys Pro Tyr Gly Lys
    50                  55                  60

Leu Ile Asp Thr Tyr Gly Asn Glu Phe Glu Leu Pro Asp Tyr Thr Val
 65                  70                  75                  80

Asn Asp Ile Arg Asn Ala Ile Pro Lys His Cys Tyr Glu Arg Ser Gly
                85                  90                  95

Val Arg Gly Leu Ala Tyr Val Ala Arg Asp Ile Ala Ser Leu Ala Thr
            100                 105                 110

Thr Phe Phe Leu Phe Asn Lys Tyr Leu Thr Pro Glu Asn Val Pro Ser
        115                 120                 125

Thr Xaa Ala Arg Ala Val Leu Trp Ala Leu Tyr Thr Val Val Gln Gly
    130                 135                 140

Leu Phe Gly Thr Gly Leu Trp Val Leu Ala His Glu Cys Gly His Gln
145                 150                 155                 160

Ser Phe Ser Thr Ser Lys Val Leu Asn Asp Thr Thr Gly Trp Ile Cys
                165                 170                 175

His Ser Ala Leu Leu Val Pro Tyr Phe Ser Trp Lys Ile Ser His Gly
            180                 185                 190

Lys His His Lys Ala Thr Gly Asn Met Glu Arg Asp Met Val Phe Val
        195                 200                 205

Pro Lys Thr Arg Gln Asp Tyr Ala Thr Arg Val Gly Lys Phe Val His
    210                 215                 220

Glu Leu His Glu Leu Thr Glu Glu Thr Pro Ile Ala Thr Leu Ile His
225                 230                 235                 240

Ser Ile Gly Gln Gln Leu Ala Gly Trp Pro Leu Tyr Leu Phe Met Asn
                245                 250                 255

Val Thr Gly His Asn Asn His Glu Arg Gln His Glu Gly Arg Gly Lys
            260                 265                 270

Gly Lys Val Asn Ser Phe Trp Thr Val Ser His Phe Asn Pro Ala Ser
        275                 280                 285

Pro Leu Tyr Glu Ala Lys Asp Ala Lys Leu Ile Leu Leu Ser Asp Leu
    290                 295                 300

Gly Ile Ala Ile Thr Ala Ala Val Leu Ile Met Leu Ser Lys Thr Tyr
305                 310                 315                 320

Gly Phe Tyr Asn Met Ala Ile Trp Tyr Phe Ile Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Ser Gly Glu Ser Trp Asn Tyr Val Arg Gly Ala Ala
        355                 360                 365

Ala Thr Ile Asp Arg Glu Phe Gly Phe Ile Gly Arg Thr Leu Leu His
    370                 375                 380

Gly Ile Ile Glu Thr His Val Leu His His Tyr Val Ser Thr Ile Pro
385                 390                 395                 400
```

```
Phe Tyr His Ala Asp Glu Ala Thr Glu Ala Ile Lys Pro Ile Met Gly
            405                 410                 415

Arg His Tyr Arg Ala Asp Val Arg Gly Gly Ser Leu Gly Phe Leu Lys
            420                 425                 430

Ser Leu Trp Ser Ser Ala Arg Trp Cys Gln Trp Val Glu Pro Ser Glu
            435                 440                 445

Gly Ala Glu Gly Glu Gly Lys Lys Val Phe Phe Phe Arg Asn Arg Asn
450                 455                 460

Gly Leu Gly Thr Pro Pro Met Lys Leu Lys Ala
465                 470                 475

<210> SEQ ID NO 33
<211> LENGTH: 1293
<212> TYPE: DNA
<213> ORGANISM: Botrytis cinerea

<400> SEQUENCE: 33
atgactctcg attacacaag tcacccggcg agctggtca aaggagggga ggtccctaca      60
aaccctaaag tgactgtcaa ggatttgcgc aatgcgattc ctgagcactg cttcaagcca     120
tcttacaagc tttcattttg gtaccttttc agagacctat ttgttgctac aataacggtg     180
gttgtagcat atttatatat acctcgaatc gagactaacg tgcttcgtta tgcggcttgg     240
gctacttatg gagttattca aggactaacg gctactggca tctgggtact tggccatgag     300
tgtggacact ctgcattctc cccgtccgac attttgaatg atactctggg ctggattctg     360
cattctgctc tcctcacgcc ctacttctcc tggcaatcta gccatcgacg ccatcatata     420
tatgcaaatc atttggtaaa agaccacaac tacgtgcccc taccaaagga tgagtatgcc     480
gcgctcttat ctgttgacgt tagtcgacta aaagagctta ctgaggattc tcccatttac     540
acattactac gcatagtagc acaacatctc ttcggttttc cattgtacct tacagcgaac     600
atcactgcat ctcaaggttc actgaatcag gctcaatcca aaaatattct aggcaacagt     660
cacttctcac cagcaagcac actatttcgt cccgaggaat cacatctcat tattctttcg     720
gatattggca ttggccttgt cgtgtttgga ctttggtacg ctagccaaat atttggtgga     780
tccatgattg cattgttgta tcttcaacct tatctctggg tcaaccactg gattgtcgct     840
atcacctatc tgcatcatac acaccctgat gtacccaaat acgaaccgga agcatggaca     900
tttcttaaag gtgcacttgc aacagttgat cgggagctgg ggtgggtggg aaagcacatg     960
ctacacaaca ttgccgagtt ccatgttatt caccacctat tttcacgtat ccctcaatat    1020
cacgctgagg aagcgaccaa ggctattatg ccattgctga aaagctctta ccgtagtgat    1080
aagaagcgaa acttttggat gtgtatgtgg gagtctttta ctaagtgcca gtacgttgtt    1140
ccatatgacg ttaaggctaa gctagaagat cgtacaatgg tctacaaggg tggtccaacg    1200
ccaacctcag agatctttat gaggaagaaa ggatgggtca aggaggtgaa tcagagtaaa    1260
cagttgggat ctgctgatag ctcaagcatt tga                                 1293

<210> SEQ ID NO 34
<211> LENGTH: 430
<212> TYPE: PRT
<213> ORGANISM: Botrytis cinerea

<400> SEQUENCE: 34

Met Thr Leu Asp Tyr Thr Ser His Pro Ala Glu Leu Val Lys Gly Gly
1               5                   10                  15

Glu Val Pro Thr Asn Pro Lys Val Thr Val Lys Asp Leu Arg Asn Ala
```

```
                20                  25                  30
Ile Pro Glu His Cys Phe Lys Pro Ser Tyr Lys Leu Ser Phe Trp Tyr
             35                  40                  45

Leu Phe Arg Asp Leu Phe Val Ala Thr Ile Thr Val Val Ala Tyr
 50                  55                  60

Leu Tyr Ile Pro Arg Ile Glu Thr Asn Val Leu Arg Tyr Ala Ala Trp
 65                  70                  75                  80

Ala Thr Tyr Gly Val Ile Gln Gly Leu Thr Ala Thr Gly Ile Trp Val
                 85                  90                  95

Leu Gly His Glu Cys Gly His Ser Ala Phe Ser Pro Ser Asp Ile Leu
            100                 105                 110

Asn Asp Thr Leu Gly Trp Ile Leu His Ser Ala Leu Leu Thr Pro Tyr
            115                 120                 125

Phe Ser Trp Gln Ser Ser His Arg His His Ile Tyr Ala Asn His
            130                 135                 140

Leu Val Lys Asp His Asn Tyr Val Pro Leu Pro Lys Asp Glu Tyr Ala
145                 150                 155                 160

Ala Leu Leu Ser Val Asp Val Ser Arg Leu Glu Glu Leu Thr Glu Asp
                165                 170                 175

Ser Pro Ile Tyr Thr Leu Leu Arg Ile Val Ala Gln His Leu Phe Gly
            180                 185                 190

Phe Pro Leu Tyr Leu Thr Ala Asn Ile Thr Ala Ser Gln Gly Ser Leu
            195                 200                 205

Asn Gln Ala Gln Ser Lys Asn Ile Leu Gly Asn Ser His Phe Ser Pro
            210                 215                 220

Ala Ser Thr Leu Phe Arg Pro Glu Glu Ser His Leu Ile Ile Leu Ser
225                 230                 235                 240

Asp Ile Gly Ile Gly Leu Val Val Phe Gly Leu Trp Tyr Ala Ser Gln
                245                 250                 255

Ile Phe Gly Gly Ser Met Ile Ala Leu Leu Tyr Leu Gln Pro Tyr Leu
            260                 265                 270

Trp Val Asn His Trp Ile Val Ala Ile Thr Tyr Leu His His Thr His
            275                 280                 285

Pro Asp Val Pro Lys Tyr Glu Pro Glu Ala Trp Thr Phe Leu Lys Gly
            290                 295                 300

Ala Leu Ala Thr Val Asp Arg Glu Leu Gly Trp Val Gly Lys His Met
305                 310                 315                 320

Leu His Asn Ile Ala Glu Phe His Val Ile His His Leu Phe Ser Arg
                325                 330                 335

Ile Pro Gln Tyr His Ala Glu Glu Ala Thr Lys Ala Ile Met Pro Leu
            340                 345                 350

Leu Lys Ser Ser Tyr Arg Ser Asp Lys Arg Asn Phe Trp Met Cys
            355                 360                 365

Met Trp Glu Ser Phe Thr Lys Cys Gln Tyr Val Val Pro Tyr Asp Val
            370                 375                 380

Lys Ala Lys Leu Glu Asp Arg Thr Met Val Tyr Lys Gly Gly Pro Thr
385                 390                 395                 400

Pro Thr Ser Glu Ile Phe Met Arg Lys Lys Gly Trp Val Lys Glu Val
                405                 410                 415

Asn Gln Ser Lys Gln Leu Gly Ser Ala Asp Ser Ser Ser Ile
            420                 425                 430

<210> SEQ ID NO 35
```

<211> LENGTH: 30
<212> TYPE: DNA
<213> ORGANISM: Artificial Sequence
<220> FEATURE:
<223> OTHER INFORMATION: Description of Artificial Sequence: Synthetic Primer

<400> SEQUENCE: 35
aacatgacgg tcaccacccg cagccacaag         30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic Primer

<400> SEQUENCE: 36
ctgggtgctc tgaacggtgt gcgcccaaat         30

<210> SEQ ID NO 37
<211> LENGTH: 1290
<212> TYPE: DNA
<213> ORGANISM: Neurospora crassa

<400> SEQUENCE: 37
atggctgtca ctactaggtc acacaaagcc gccgctgcca ccgaacctga agttgtgtct    60
acaggagtgg atgcagtcag cgctgccgca ccaagcagta gtagctcctc atcctcccaa   120
aagtcagctg agcctatcga atatccagac atcaagacaa ttcgtgacgc ataccagac    180
cactgcttta gacctcgcgt ttggatatcc atggcgtact ttattcgcga ttttgcaatg   240
gctttcggcc tcggatactt ggcatggcaa tacatccctt tgattgcaag taccccattg   300
agatacggag cttgggcttt gtacggttac ctccagggac tcgtctgtac tggaatttgg   360
atcttggctc acgaatgcgg tcacggagcc ttttctagac acacctggtt caacaacgtt   420
atgggttgga ttggtcactc tttcctacta gtcccatatt ttagctggaa attttcccat   480
caccgtcatc ataggttcac cggacatatg gaaaaagata tggcgttcgt tccagccacg   540
gaggcggaca gaaatcagag aaaactagct aatctctata tggacaaaga gactgcggag   600
atgttcgagg atgttcctat tgtgcagttg gttaaactaa ttgctcacca actcgccggt   660
tggcagatgt atctcttgtt caacgttagt gccggaaaag gctccaaaca gtgggaaacc   720
ggcaaaggtg gaatgggatg gctccgcgtg agccatttcg aaccaagttc agccgttttc   780
agaaacagcg aagcaattta catagctcta agcgatctcg gacttatgat tatgggatac   840
attctctacc aggcagccca agttgttgga tgcaaatgg ttggtctctt gtattttcaa   900
cagtacttct gggttcacca ttggctcgtt gccatcactt accttcatca cacacacgaa   960
gaagttcacc actttgatgc agattcttgg acatttgtta agggtgccct cgctaccgtg  1020
gacagagact tcggtttcat cggcaagcac ctcttccata acatcattga ccatcatgtt  1080
gttcatcacc tcttcccaag aatccctttc tactacgctg aagaagctac caattcaata  1140
agacctatgc tcggacctct ttaccacaga gatgaccgtt ctttcatggg gcaactctgg  1200
tacaacttca cacactgcaa atgggttgtc cctgatcctc aagtgccagg tgctctaatc  1260
tgggctcaca ccgttcagag tactcagtaa                                   1290

<210> SEQ ID NO 38
<211> LENGTH: 1209

<212> TYPE: DNA
<213> ORGANISM: Aspergillus nidulans

<400> SEQUENCE: 38

```
atggccgcaa ccgcgaccac tctcgctgaa atagaaaaga agaaggaaga gattacacta      60
cagacaatca agaatgccat accaaagcac tgttttaacc gtagtttgct tatttcaagt     120
gcctacgtcg tcagagacct cctctacgca tcagttttgt tctattttgc acttcatatt     180
gatacgctct tctcatccca gctccttagg atcttggcat ggacagctta cggtttcatg     240
caaggctgcg tgggaacggg tatatggata ttggcacatg aatgcggaca cggagctttt     300
agcccttacc aaacctggaa cgacgttgtt gggtggaccc ttcattctct tctcatggtc     360
ccttacttct cttggaaaat aacccacgca aggcaccaca gatatacgaa caataccgag     420
agggacacag ccttcgttcc ctggaccgag aaggaatacg acaccagacc tcgttacttc     480
cctgcatggt tcgagatgtt tgaagacaca ccagtgtata acttgatttc attgctcgcc     540
catcagatcg ccggctggca aatgtacctc tgcttctacg tctcagccgg agccaaaagt     600
aagcctgttc cacaaggcaa gcagtccgga tggtttggag gtcaacaatc tgcatcacac     660
tttgacccag gaagctctct atggaccgaa aaccagcgcc atctaatcgc aatctccgac     720
cttggactcc ttctcgtggc cgccgcgaat tggtacttgg ctcaacaagt tggtgttcta     780
agaatggtgc tcatttacgt cgtccccta cttttgggtcc accactggct agtcgccatc     840
acgtacctcc accacactca cccatccata ccacactaca ccgactctac ctggacattc     900
actaaaggag cactctcaac agtggatcgt gacttcggat ttataggaag gcacttcttt     960
caccacatca ttgatcacca cgtcgttcat cacttgttca ataggatacc attctatcac    1020
gcagaggaag ctactaacgc aataatacca gttctcggtg atatgtacca tagagaagaa    1080
accggattcc tctggagtct tatggaaact tataaaaact gtcgctttgt tggcgtggag    1140
aacgatgtgg gtaaggaggg agttctccat tgggttttcg aagaaaagaa aggcgctaaa    1200
gctgaatag                                                            1209
```

<210> SEQ ID NO 39
<211> LENGTH: 1446
<212> TYPE: DNA
<213> ORGANISM: Neurospora crassa

<400> SEQUENCE: 39

```
atggcgtccg tctcctctgc ccttcccgag ggcaacaagc ctgccctgcg caggacccaa      60
accgaggcca cctccgactc ataccctggt accgctgatg cctctccctt cgactctccc     120
cttgagcgct cggcctccaa cacctcgctt tcttcccagg cctctgacaa cgtcaagacc     180
gacaaggccg agttcggcaa gctgctcgac acgtatggca acgagttcga ggtccccgac     240
ttcaccatca aggacatccg cgatgccatc ccgcccact gctttgagcg ttcggctctt     300
cacagcttgg cgcacgtcgt ccgcgacatc atttacctca ccgtcacttt ttacgtctgg     360
aacaagtatg tcactcccga gtacatcccc atgaaggctg cccgtgtcgt cctctggggt     420
ctgtacacct tcatgcaggg ccttttcggc accggtctct gggttcttgc ccatgagtgc     480
ggtcaccagg ctttctcccc gtccaggttg atcaacgaca ccgtcggctg gtcctccac     540
tctgcccttc tcgtcccta cttctcgtgg aagttctccc acagcaagca ccacaaggcc     600
accggcaaca tcgagcgtga catggtcttc gttcctcgga cccgcgagca gtttgcgtct     660
cgcatcggcc gtttcgtcca tgagatttcc gagttgaccg aggagacccc catctacacc    720
```

-continued

```
ttgatccacc ttatcggtca gcagctcatc ggctggccca actacctcat gaccaacgtc    780
accggccaca acttccacga gaggcagcgc gagggtcgtg gcaagggcaa gaagaacggc    840
tggttcactg gtgtcaacca cttcaacccc agctctcccc tctatgagga gcgtgaggcc    900
ccctggatca tcgtctccga catcggtatc gctatcgccg ccaccgccct catctacctc    960
ggcaacacct tcggctggtc aacatgttc gtctggtact tccttcccta cctctgggtc   1020
aaccactggc ttgttgccat cacctacctc agcacaccg accctcgct ccccactac     1080 accctgatc agtggaactt tgtccgtggt gccgccgcga ctattgaccg cgagttcggc    1140
ttcatcggcc gtcacctcct ccacggcatt atcgagaccc acgttctcca ccactacgtc   1200
agcaccattc ccttttacca cgccgacgag gcctccgagg ccatcaagaa ggtcatgggc   1260
cgtcactacc gcgctgacgt ccaagatggc cccatcggtt tcatcaaggc catgtggaag   1320
gctgctcgtt ggtgccagtg ggttgagcct accgagggcg ctgagggtaa gggcaagggc   1380
gtcttgttct accgcaacca gaacggtctc ggtgtcaagc tgccaagct ccccaaaacc    1440 aactaa                                                              1446
```

<210> SEQ ID NO 40
<211> LENGTH: 481
<212> TYPE: PRT
<213> ORGANISM: Neurospora crassa

<400> SEQUENCE: 40

```
Met Ala Ser Val Ser Ser Ala Leu Pro Glu Gly Asn Lys Pro Ala Leu
  1               5                  10                  15

Arg Arg Thr Gln Thr Glu Ala Thr Ser Asp Ser Tyr Pro Gly Thr Ala
             20                  25                  30

Asp Ala Ser Pro Phe Asp Ser Pro Leu Glu Arg Ser Ala Ser Asn Thr
         35                  40                  45

Ser Leu Ser Ser Gln Ala Ser Asp Asn Val Lys Thr Asp Lys Ala Glu
     50                  55                  60

Phe Gly Lys Leu Leu Asp Thr Tyr Gly Asn Glu Phe Glu Val Pro Asp
 65                  70                  75                  80

Phe Thr Ile Lys Asp Ile Arg Asp Ala Ile Pro Ala His Cys Phe Glu
                 85                  90                  95

Arg Ser Ala Leu His Ser Leu Ala His Val Val Arg Asp Ile Ile Tyr
            100                 105                 110

Leu Thr Val Thr Phe Tyr Val Trp Asn Lys Tyr Val Thr Pro Glu Tyr
        115                 120                 125

Ile Pro Met Lys Ala Ala Arg Val Val Leu Trp Gly Leu Tyr Thr Phe
    130                 135                 140

Met Gln Gly Leu Phe Gly Thr Gly Leu Trp Val Leu Ala His Glu Cys
145                 150                 155                 160

Gly His Gln Ala Phe Ser Pro Ser Arg Leu Ile Asn Asp Thr Val Gly
                165                 170                 175

Trp Val Leu His Ser Ala Leu Leu Val Pro Tyr Phe Ser Trp Lys Phe
            180                 185                 190

Ser His Ser Lys His His Lys Ala Thr Gly Asn Ile Glu Arg Asp Met
        195                 200                 205

Val Phe Val Pro Arg Thr Arg Glu Gln Phe Ala Ser Arg Ile Gly Arg
    210                 215                 220

Phe Val His Glu Ile Ser Glu Leu Thr Glu Glu Thr Pro Ile Tyr Thr
225                 230                 235                 240
```

```
Leu Ile His Leu Ile Gly Gln Gln Leu Ile Gly Trp Pro Asn Tyr Leu
            245                 250                 255

Met Thr Asn Val Thr Gly His Asn Phe His Glu Arg Gln Arg Glu Gly
            260                 265                 270

Arg Gly Lys Gly Lys Lys Asn Gly Trp Phe Thr Gly Val Asn His Phe
        275                 280                 285

Asn Pro Ser Ser Pro Leu Tyr Glu Glu Arg Glu Ala Pro Trp Ile Ile
    290                 295                 300

Val Ser Asp Ile Gly Ile Ala Ile Ala Ala Thr Ala Leu Ile Tyr Leu
305                 310                 315                 320

Gly Asn Thr Phe Gly Trp Ser Asn Met Phe Val Trp Tyr Phe Leu Pro
                325                 330                 335

Tyr Leu Trp Val Asn His Trp Leu Val Ala Ile Thr Tyr Leu Gln His
            340                 345                 350

Thr Asp Pro Ser Leu Pro His Tyr Thr Pro Asp Gln Trp Asn Phe Val
        355                 360                 365

Arg Gly Ala Ala Ala Thr Ile Asp Arg Glu Phe Gly Phe Ile Gly Arg
    370                 375                 380

His Leu Leu His Gly Ile Ile Glu Thr His Val Leu His His Tyr Val
385                 390                 395                 400

Ser Thr Ile Pro Phe Tyr His Ala Asp Glu Ala Ser Glu Ala Ile Lys
                405                 410                 415

Lys Val Met Gly Arg His Tyr Arg Ala Asp Val Gln Asp Gly Pro Ile
            420                 425                 430

Gly Phe Ile Lys Ala Met Trp Lys Ala Ala Arg Trp Cys Gln Trp Val
        435                 440                 445

Glu Pro Thr Glu Gly Ala Glu Gly Lys Gly Lys Gly Val Leu Phe Tyr
    450                 455                 460

Arg Asn Gln Asn Gly Leu Gly Val Lys Pro Ala Lys Leu Pro Lys Thr
465                 470                 475                 480

Asn

<210> SEQ ID NO 41
<211> LENGTH: 1200
<212> TYPE: DNA
<213> ORGANISM: Mortierella alpina

<400> SEQUENCE: 41
atggcacctc caacactat cgatgccggt ttgacccagc gtcatatcag cacctcggcc      60
ccaaactcgg ccaagcctgc cttcgagcgc aactaccagc tccccgagtt caccatcaag     120
gagatccgag agtgcatccc tgcccactgc tttgagcgct ccggtctccg tggtctctgc     180
cacgttgcca tcgatctgac ttgggcgtcg ctcttgttcc tggctgcgac ccagatcgac     240
aagtttgaga tcccttgat ccgctatttg gcctggcctg tttactggat catgcagggt     300
attgtctgca ccggtgtctg ggtgctggct cacgagtgtg gtcatcagtc cttctcgacc     360
tccaagaccc tcaacaacac agttggttgg atcttgcact cgatgctctt ggtcccctac     420
cactcctgga gaatctcgca ctcgaagcac acaaggcca ctggccatat gaccaaggac     480
caggtctttg tgcccaagac ccgctcccag gttggcttgc ctcccaagga gaacgctgct     540
gctgccgttc aggaggagga catgtccgtg cacctggatg aggaggctcc cattgtgact     600
ttgttctgga tggtgatcca gttcttgttc ggatggcccg cgtacctgat tatgaacgcc     660
tctggccaag actacggccg ctggacctcg cacttccaca cgtactcgcc catctttgag     720
```

| cccgcaact | tttcgacat | tattatctcg | gacctcggtg | tgttggctgc | cctcggtgcc | 780 |
| ctgatctatg | cctccatgca | gttgtcgctc | ttgaccgtca | ccaagtacta | tattgtcccc | 840 |
| tacctctttg | tcaactttg | gttggtcctg | atcaccttct | tgcagcacac | cgatcccaag | 900 |
| ctgccccatt | accgcgaggg | tgcctggaat | ttccagcgtg | gagctctttg | caccgttgac | 960 |
| cgctcgtttg | gcaagttctt | ggaccatatg | ttccacggca | ttgtccacac | ccatgtggcc | 1020 |
| catcacttgt | tctcgcaaat | gccgttctac | catgctgagg | aagctaccta | tcatctcaag | 1080 |
| aaactgctgg | gagagtacta | tgtgtacgac | ccatccccga | tcgtcgttgc | ggtctggagg | 1140 |
| tcgttccgtg | agtgccgatt | cgtggaggat | cagggagacg | tggtcttttt | caagaagtaa | 1200 |

<210> SEQ ID NO 42
<211> LENGTH: 1290
<212> TYPE: DNA
<213> ORGANISM: Neurospora crassa

<400> SEQUENCE: 42

| atggcggtca | ccacccgcag | ccacaaggcc | gcggccgcca | ccgagcccga | ggttgtcagc | 60 |
| accggcgttg | acgccgtctc | tgctgctgct | ccctcctcct | cctcctcctc | ttccagccaa | 120 |
| aagtcggccg | agcccatcga | ataccccgac | atcaagacca | tccgcgacgc | catccccgac | 180 |
| cactgcttcc | gcccgcgcgt | ctggatctcc | atggcctact | tcatccgcga | cttcgccatg | 240 |
| gcctttggcc | tcggctacct | cgcctggcag | tacatccccc | tgatcgcctc | caccccgctc | 300 |
| cgctacggcg | cctgggctct | gtacggctac | ctccagggtc | tcgtctgcac | gggcatctgg | 360 |
| attctggcgc | acgagtgcgg | ccacggcgcc | ttctcgaggc | acacgtggtt | caacaacgtc | 420 |
| atggggtgga | ttggccactc | cttcctcttg | gtcccttact | tcagctggaa | gttcagccac | 480 |
| catcgccacc | atcgcttcac | cggccacatg | gagaaggaca | tggcgtttgt | gcctgccacc | 540 |
| gaggctgatc | gcaaccagag | gaagctggcc | aacttgtaca | tggacaagga | gacggccgag | 600 |
| atgtttgagg | atgtgcccat | tgtccagctc | gtcaagctca | tcgcccacca | gctggccggc | 660 |
| tggcagatgt | acctcctctt | caacgtctcc | gccggtaagg | gcagcaagca | gtgggagact | 720 |
| ggcaagggcg | gcatgggctg | gttgagggtt | agccactttg | agccttcctc | tgctgtgttc | 780 |
| cgcaactccg | aggccatcta | cattgccctg | tccgatcttg | gtctcatgat | catgggctac | 840 |
| atcctctacc | aggccgcgca | ggttgttggc | tggcagatgg | tgggtctgct | gtacttccag | 900 |
| cagtacttct | gggttcacca | ttggttggtc | gccatcactt | acctccacca | cacccacgag | 960 |
| gaagtccacc | actttgacgc | cgactcgtgg | accttcgtca | agggcgctct | cgccaccgtc | 1020 |
| gaccgcgatt | ttggcttcat | tggcaagcac | ctcttccaca | acattatcga | ccaccacgtc | 1080 |
| gtccaccact | tgttccctcg | catccccttc | tactacgccg | aagaagccac | caactcgatc | 1140 |
| cgccccatgc | tcggcccccT | ctaccaccgc | gacgaccgct | ccttcatggg | ccagctgtgg | 1200 |
| tacaacttca | cccactgcaa | gtgggtcgtt | ccggaccccc | aggtccccgg | cgcgcttatt | 1260 |
| tgggcgcaca | ccgttcagag | cacccagtaa | | | | 1290 |

<210> SEQ ID NO 43
<211> LENGTH: 1617
<212> TYPE: DNA
<213> ORGANISM: Mortierella alpina delta six

<400> SEQUENCE: 43

| cgacactcct | tccttcttct | cacccgtcct | agtccccttc | aaccccctc | tttgacaaag | 60 |
| acaacaaacc | atggctgctg | ctcccagtgt | gaggacgttt | actcgggccg | aggttttgaa | 120 |

```
tgccgaggct ctgaatgagg gcaagaagga tgccgaggca cccttcttga tgatcatcga    180
caacaaggtg tacgatgtcc gcgagttcgt ccctgatcat cccggtggaa gtgtgattct    240
cacgcacgtt ggcaaggacg gcactgacgt ctttgacact tttcaccccg aggctgcttg    300
ggagactctt gccaactttt acgttggtga tattgacgag agcgaccgcg atatcaagaa    360
tgatgacttt gcggccgagg tccgcaagct gcgtaccttg ttccagtctc ttggttacta    420
cgattcttcc aaggcatact acgccttcaa ggtctcgttc aacctctgca tctggggttt    480
gtcgacggtc attgtggcca agtggggcca gacctcgacc ctcgccaacg tgctctcggc    540
tgcgcttttg ggtctgttct ggcagcagtg cggatggttg gctcacgact ttttgcatca    600
ccaggtcttc caggaccgtt tctggggtga tcttttcggc gccttcttgg gaggtgtctg    660
ccagggcttc tcgtcctcgt ggtggaagga caagcacaac actcaccacg ccgcccccaa    720
cgtccacggc gaggatcccg acattgacac ccaccctctg ttgacctgga gtgagcatgc    780
gttggagatg ttctcggatg tcccagatga ggagctgacc cgcatgtggt cgcgtttcat    840
ggtcctgaac cagacctggt tttacttccc cattctctcg tttgcccgtc tctcctggtg    900
cctccagtcc attctctttg tgctgcctaa cggtcaggcc cacaagccct cgggcgcgcg    960
tgtgcccatc tcgttggtcg agcagctgtc gcttgcgatg cactggacct ggtacctcgc   1020
caccatgttc ctgttcatca aggatcccgt caacatgctg gtgtacttt tggtgtcgca   1080
ggcggtgtgc ggaaacttgt tggcgatcgt gttctcgctc aaccacaacg gtatgcctgt   1140
gatctcgaag gaggaggcgg tcgatatgga tttcttcacg aagcagatca tcacgggtcg   1200
tgatgtccac ccgggtctat ttgccaactg gttcacgggt ggattgaact atcagatcga   1260
gcaccacttg ttcccttcga tgcctcgcca aacttttca aagatccagc ctgctgtcga   1320
gaccctgtgc aaaaagtaca atgtccgata ccacaccacc ggtatgatcg agggaactgc   1380
agaggtcttt agccgtctga acgaggtctc caaggctgcc tccaagatgg gtaaggcgca   1440
gtaaaaaaaa aaacaaggac gttttttttc gccagtgcct gtgcctgtgc ctgcttccct   1500
tgtcaagtcg agcgtttctg gaaaggatcg ttcagtgcag tatcatcatt ctccttttac   1560
ccccgctca tatctcattc atttctctta ttaaacaact tgttccccc ttcaccg       1617
```

FATTY ACID DESATURASES FROM FUNGI

This application is a national stage application under 35 U.S.C. §371 of International Application No. PCT/US03/16144 filed May 21, 2003, which claims the priority of U.S. Provisional Patent Application Ser. No. 60/382,391, filed May 22, 2002, and U.S. Provisional Patent Application Ser. No. 60/453,125, filed Mar. 7, 2003. The entire disclosure of each of the above applications is specifically incorporated herein by reference in the entirety.

BACKGROUND OF THE INVENTION

1. Field of the Invention

The invention relates generally to desaturase enzymes that modulate the number and location of double bonds in long chain poly-unsaturated fatty acids (LC-PUFA's), methods of use thereof and compositions derived therefrom. In particular, the invention relates to improved fatty acid profiles using desaturase enzymes and nucleic acids encoding for such enzymes identified in fungi.

2. Description of the Related Art

The primary products of fatty acid biosynthesis in most organisms are 16- and 18-carbon compounds. The relative ratio of chain lengths and degree of unsaturation of these fatty acids vary widely among species. Mammals, for example, produce primarily saturated and monosaturated fatty acids, while most higher plants produce fatty acids with one, two, or three double bonds, the latter two comprising polyunsaturated fatty acids (PUFA's).

Two main families of PUFAs are the omega-3 fatty acids (also represented as "n-3" fatty acids), exemplified by eicosapentaenoic acid (EPA, 20:4, n-3), and the omega-6 fatty acids (also represented as "n-6" fatty acids), exemplified by arachidonic acid (ARA, 20:4, n-6). PUFAs are important components of the plasma membrane of the cell and adipose tissue, where they may be found in such forms as phospholipids and as triglycerides, respectively. PUFAs are necessary for proper development in mammals, particularly in the developing infant brain, and for tissue formation and repair.

Several disorders respond to treatment with fatty acids. Supplementation with PUFAs has been shown to reduce the rate of restenosis after angioplasty. The health benefits of certain dietary omega-3 fatty acids for cardiovascular disease and rheumatoid arthritis also have been well documented (Simopoulos, 1997; James et al., 2000). Further, PUFAs have been suggested for use in treatments for asthma and psoriasis. Evidence indicates that PUFAs may be involved in calcium metabolism, suggesting that PUFAs may be useful in the treatment or prevention of osteoporosis and of kidney or urinary tract stones. The majority of evidence for health benefits applies to the long chain omega-3 fats, EPA and DHA which are in fish and fish oil. With this base of evidence, health authorities and nutritionists in Canada (Scientific Review Committee, 1990, Nutrition Recommendations, Minister of National Health and Welfare, Canada, Ottowa), Europe (de Deckerer et al., 1998), the United Kingdom (The British Nutrition Foundation, 1992, Unsaturated fatty-acids—nutritional and physiological significance: The report of the British Nutrition Foundation's Task Force, Chapman and Hall, London), and the United States (Simopoulos et al., 1999) have recommended increased dietary consumption of these PUFAs.

PUFAs also can be used to treat diabetes (U.S. Pat. No. 4,826,877; Horrobin et al., 1993). Altered fatty acid metabolism and composition has been demonstrated in diabetic animals. These alterations have been suggested to be involved in some of the long-term complications resulting from diabetes, including retinopathy, neuropathy, nephropathy and reproductive system damage. Primrose oil, which contains GLA, has been shown to prevent and reverse diabetic nerve damage.

PUFAs, such as linoleic acid (LA, 18:2, $\Delta 9$, 12) and $\alpha$-linolenic acid (ALA18:3, $\Delta 9$, 12, 15), are regarded as essential fatty acids in the diet because mammals lack the ability to synthesize these acids. However, when ingested, mammals have the ability to metabolize LA and ALA to form the n-6 and n-3 families of long-chain polyunsaturated fatty acids (LC-PUFA). These LC-PUFA's are important cellular components conferring fluidity to membranes and functioning as precursors of biologically active eicosanoids such as prostaglandins, prostacyclins, and leukotrienes, which regulate normal physiological functions.

In mammals, the formation of LC-PUFA is rate-limited by the step of $\Delta 6$ desaturation, which converts LA to $\gamma$-linolenic acid (GLA, 18:3, $\Delta 6$, 9, 12) and ALA to SDA (18:4, $\Delta 6$, 9, 12, 15). Many physiological and pathological conditions have been shown to depress this metabolic step, and consequently, the production of LC-PUFA. However, bypassing the $\Delta 6$-desaturation via dietary supplementation with EPA or DHA can effectively alleviate many pathological diseases associated with low levels of PUFA. However, as set forth in more detail below, currently available sources of PUFA are not desirable for a multitude of reasons. The need for a reliable and economical source of PUFA's has spurred interest in alternative sources of PUFA's.

Major long chain PUFAs of importance include docosahexaenoic acid (DHA, 22:6, n-3) and EPA, which are primarily found in different types of fish oil, and arachidonic acid (ARA, 20:4, n-6), found in filamentous fungi. For DHA, a number of sources exist for commercial production including a variety of marine organisms, oils obtained from cold water marine fish, and egg yolk fractions. Commercial sources of SDA include the genera *Trichodesma* and *Echium*. However, there are several disadvantages associated with commercial production of PUFAs from natural sources. Natural sources of PUFAs, such as animals and plants, tend to have highly heterogeneous oil compositions. For example, oil from the seeds of *Echum*, in addition to SDA, contain almost equivalent levels of the omega-6 fatty acid GLA. The oils obtained from these sources therefore can require extensive purification to separate out one or more desired PUFAs or to produce an oil which is enriched in one or more PUFA.

Natural sources of PUFAs also are subject to uncontrollable fluctuations in availability. Fish stocks may undergo natural variation or may be depleted by overfishing. In addition, even with overwhelming evidence of their therapeutic benefits, dietary recommendations regarding omega-3 fatty acids are not heeded. Fish oils have unpleasant tastes and odors, which may be impossible to economically separate from the desired product, and can render such products unacceptable as food supplements. Animal oils, and particularly fish oils, can accumulate environmental pollutants. Foods may be enriched with fish oils, but again, such enrichment is problematic because of cost and declining fish stocks worldwide. This problem is an impediment to consumption and intake of whole fish. Nonetheless, if the health messages to increase fish intake were embraced by communities, there would likely be a problem in meeting demand for fish. Furthermore, there are problems with sustainability of this industry which relies heavily on wild fish stocks for aquaculture feed (Naylor et al., 2000).

Other natural limitations favor a novel approach for the production of omega-3 fatty acids. Weather and disease can cause fluctuation in yields from both fish and plant sources.

Cropland available for production of alternate oil-producing crops is subject to competition from the steady expansion of human populations and the associated increased need for food production on the remaining arable land. Crops that do produce PUFAs, such as borage, have not been adapted to commercial growth and may not perform well in monoculture. Growth of such crops is thus not economically competitive where more profitable and better-established crops can be grown. Large scale fermentation of organisms such as *Mortierella* is also expensive. Natural animal tissues contain low amounts of ARA and are difficult to process. Microorganisms such as *Porphyridium* and *Mortierella* are difficult to cultivate on a commercial scale.

A number of enzymes are involved in PUFA biosynthesis. LA, (18:2, Δ9, 12) is produced from oleic acid (OA, 18:1, Δ9) by a Δ12-desaturase while ALA (18:3) is produced from LA by a Δ15-desaturase. SDA (18:4, Δ6, 9, 12, 15) and GLA (18:3, Δ6, 9, 12) are produced from LA and ALA by a Δ6-desaturase. However, as stated above, mammals cannot desaturate beyond the Δ9 position and therefore cannot convert oleic acid into LA. Likewise, ALA cannot be synthesized by mammals. Other eukaryotes, including fungi and plants, have enzymes which desaturate at the carbon 12 and carbon 15 position. The major poly-unsaturated fatty acids of animals therefore are derived from diet via the subsequent desaturation and elongation of dietary LA and ALA.

U.S. Pat. No. 5,952,544 describes nucleic acid fragments isolated and cloned from *Brassica napus* that encode fatty acid desaturase enzymes. Expression of the nucleic acid fragments of the '544 patent are expressed in plants and result in accumulation of ALA. However, in transgenic plants expressing the plant Δ15-desaturase, substantial LA remains unconverted by the desaturase. A more active enzyme that converts more LA to ALA would be advantageous. Increased conversion from LA to ALA would create greater amounts of ALA. Increased ALA levels allow the Δ6-desaturase, when co-expressed with nucleic acid encoding for the Δ15-desaturase, to act upon the ALA, thereby producing greater levels of SDA. Because of the multitude of beneficial uses for SDA, there is a need to create a substantial increase in the yield of SDA. Nucleic acids from various sources have been sought to increase SDA yield. However, innovations that would allow for improved commercial production in land-based crops are still highly desired. (See, e.g., Reed et al., 2000). Furthermore, the use of desaturase polynucleotides derived from *Caenorhabditis elegans* (Meesapyodsuk et al., 2000) is not ideal for the commercial production of enriched plant seed oils.

Nucleic acids encoding Δ15-desaturases have been isolated from several species of cyanobacteria and plants, including *Arabidopsis*, soybean, and parsley. The deduced amino acid sequences of these desaturases demonstrate a high degree of similarity, most notable in the region of three histidine-rich motifs that, without being bound by any one theory, are believed to be involved in iron-binding. However, no Δ15-desaturase has been isolated from any fungal species. Furthermore, even with the genomes of several fungal species having been sequenced, and using sophisticated algorithms, searches utilizing known Δ15-desaturase cDNA and amino acid sequences against *Aspergillus* and *Neurospora* DNA databases have not yielded Δ15-desaturases.

Therefore, it would be advantageous to obtain genetic material involved in PUFA biosynthesis and to express the isolated material in a plant system, in particular, a land-based terrestrial crop plant system, which can be manipulated to provide production of commercial quantities of one or more PUFA's. There is also a need to increase omega-3 fat intake in humans and animals. Thus there is a need to provide a wide range of omega-3 enriched foods and food supplements so that subjects can choose feed, feed ingredients, food and food ingredients which suit their usual dietary habits. Currently there is only one omega-3 fatty acid, ALA, available in vegetable oils. However, there is poor conversion of ingested ALA to the longer-chain omega-3 fatty acids such as EPA and DHA. It has been demonstrated in copending U.S. Application Ser. No. 10/384,369 for "Treatment And Prevention Of Inflammatory Disorders," that elevating ALA intake from the community average of 1/g day to 14 g/day by use of flaxseed oil, only modestly increased plasma phospholipid EPA levels. A 14-fold increase in ALA intake resulted in a 2-fold increase in plasma phospholipid EPA (Manzioris et al., 1994).

Thus, to that end, there is a need for efficient and commercially viable production of PUFAs using fatty acid desaturases, genes encoding them, and recombinant methods of producing them. A need also exists for oils containing higher relative proportions of and/or enriched in specific PUFA's and food compositions and supplements containing them. A need also exists for reliable economical methods of producing specific PUFA's.

Despite inefficiencies and low yields as described above, the production of omega-3 fatty acids via the terrestrial food chain is an enterprise beneficial to public health and, in particular, the production of SDA. SDA in particular is important because, as described above, there is low conversion of ALA to EPA. This is because in this three enzyme process (requiring Δ6, Δ12, and Δ15) the initial enzyme, Δ6-desaturase, has low activity in humans and is rate-limiting. Evidence that Δ6-desaturase is rate-limiting is provided by studies which demonstrate that the conversion of its substrate, ALA, is less efficient than the conversion of its product, SDA to EPA in mice and rats (Yamazaki et al., 1992; Huang, 1991).

Based on such studies, it is seen that in commercial oilseed crops, such as canola, soybean, corn, sunflower, safflower, or flax, the conversion of some fraction of the mono and poly-unsaturated fatty acids that typify their seed oil to SDA, requires the seed-specific expression of multiple desaturase enzymes, including Δ6- and Δ12, and an enzyme that has Δ15-desaturase activity. Oils derived from plants expressing elevated levels of Δ6, Δ12, and Δ15-desaturases are rich in SDA and other omega-3 fatty acids. Such oils can be utilized to produce foods and food supplements enriched in omega-3 fatty acids and consumption of such foods effectively increases tissue levels of EPA and DHA. Foods and food stuffs, such as milk, margarine and sausages, all made or prepared with omega-3 enriched oils will result in therapeutic benefits. It has been shown that subjects can have an omega-3 intake comparable to EPA and DHA of at least 1.8 g/day without altering their dietary habits by utilizing foods containing oils enriched with omega-3 fatty acids (Naylor, supra.). Thus, there exists a strong need for novel nucleic acids of Δ15-desaturases for use in transgenic crop plants to produce oils enriched in PUFAs. New plant seed oils enriched for PUFAs and, particular, omega-3 fatty acids such as stearidonic acid are similarly needed.

SUMMARY OF THE INVENTION

In one aspect, the invention provides isolated nucleic acids encoding a polypeptide capable of desaturating a fatty acid molecule at carbon 15 (Δ15-desaturase). These may be used to transform cells or modify the fatty acid composition of a plant or the oil produced by a plant. One embodiment of the invention is an isolated polynucleotide sequence isolated from a fungal species having unique desaturase activity. The isolated polynucleotides may be isolated from fungal species preferably belonging to a phyla selected from the group consisting of zygomycota, basidiomycota, and ascomycota. In certain embodiments, the isolated polynucleotides are isolated from a fungal species selected from the group consisting of *Neurospora crassa, Aspergillus nidulans*, and *Botrytis cinerea*.

In another aspect, the invention provides an isolated polynucleotide comprising a sequence selected from the group consisting of: (a) a polynucleotide encoding the polypeptide of SEQ ID NO:3, SEQ ID NO:5 or SEQ ID NO:34; (b) a polynucleotide comprising the nucleic acid sequence of SEQ ID NO:1, SEQ ID NO:2, SEQ ID NO:4 or SEQ ID NO: 33; (c) a polynucleotide hybridizing to one or more of SEQ ID NO:1, SEQ ID NO:2, SEQ ID NO:4 or SEQ ID NO: 33, or a complement thereof, under conditions of 5×SSC, 50% formamide and 42° C.; and (d) a fungal polynucleotide encoding a polypeptide having at least one of the amino acid motifs: TrpIleLeuAlaHisGluCysGlyHisGlyAlaSerPhe (WILAHECGHGASF) (SEQ ID NO:6); LeuAlaHisGluCysGlyHis (LAHECGH) (SEQ ID NO:7); HisSerPheLeuLeuValProTyrPheSerTrpLys (HSFLLVPYFSWK) (SEQ ID NO:8); LeuLeuValProTyrPheSerTrpLys (LLVPYFSWK) (SEQ ID NO:9); His(His/Ala)ArgHisHisArg(Phe/Tyr)ThrThr (H(H/A)RHHR(F/Y)TT) (SEQ ID NO:10, SEQ ID NO:19, SEQ ID NO:20, or SEQ ID NO:21); TrpValHisHisTrpLeuValAlaIleThrTyrLeu(His/Gln)HisThrHis (WVHHWLVAITYL(H/Q)HTH) (SEQ ID NO:11); AlaIleThrTyrLeu(His/Gln)HisThr (AITYL(H/Q)HT) (SEQ ID NO:12); GlyAlaLeuAlaThrValAspArg (GALATVDR) (SEQ ID NO:13) or HisValValHisHisLeuPheXaaArgIleProPheTyr (HVVHHLFXRIPFY) (SEQ ID NO:14 or SEQ ID NO:22).

In yet another aspect, the invention provides a recombinant vector comprising an isolated polynucleotide in accordance with the invention. The term "recombinant vector" as used herein, includes any recombinant segment of DNA which one desires to introduce into a host cell, tissue and/or organism, and specifically includes expression cassettes isolated from a starting polynucleotide. A recombinant vector may be linear or circular. In various aspects, a recombinant vector may comprise at least one additional sequence chosen from the group consisting of: regulatory sequences operatively coupled to the polynucleotide; selection markers operatively coupled to the polynucleotide; marker sequences operatively coupled to the polynucleotide; a purification moiety operatively coupled to the polynucleotide; and a targeting sequence operatively coupled to the polynucleotide.

In still yet another aspect, the invention provides cells, such as mammal, plant, insect, yeast and bacteria cells transformed with the polynucleotides of the instant invention. In a further embodiment, the cells are transformed with recombinant vectors containing constitutive and tissue-specific promoters in addition to the polynucleotides of the instant invention. In certain embodiments of the invention, such cells may be further defined as transformed with a nucleic acid sequence encoding a polypeptide having desaturase activity that desaturates a fatty acid molecule at carbon 6.

In still yet another aspect, the invention provides a polypeptide, including fragments and proteins having desaturase activity that desaturates a fatty acid molecule at carbon 15. In one embodiment of the invention, the polypeptide comprises at least one of the amino acid motifs: TrpIleLeuAlaHisGluCysGlyHisGlyAlaSerPhe (WILAHECGHGASF) (SEQ ID NO:6); LeuAlaHisGluCysGlyHis (LAHECGH) (SEQ ID NO:7); HisSerPheLeuLeuValProTyrPheSerTrpLys (HSFLLVPYFSWK) (SEQ ID NO:8); LeuLeuValProTyrPheSerTrpLys (LLVPYFSWK) (SEQ ID NO:9); His(His/Ala)ArgHisHisArg(Phe/Tyr)ThrThr (H(H/A)RHHR(F/Y)TT) (SEQ ID NO:10, SEQ ID NO:19, SEQ ID NO:20, or SEQ ID NO:21); TrpValHisHisTrpLeuValAlaIleThrTyrLeu(His/Gln)HisThrHis (WVHHWLVAITYL(H/Q)HTH) (SEQ ID NO:11); AlaIleThrTyrLeu(His/Gln)HisThr (AITYL(H/Q)HT) (SEQ ID NO:12); GlyAlaLeuAlaThrValAspArg (GALATVDR) (SEQ ID NO:13) or HisValValHisHisLeuPheXaaArgIleProPheTyr (HVVHHLFXRIPFY) (SEQ ID NO:14 or SEQ ID NO:22). In further embodiments the polypeptide is further defined as comprising all of said amino acid motifs. The invention also provides a fungal polypeptide comprising the amino acid sequence of SEQ ID NO:3, SEQ ID NO:5 or SEQ ID NO:34; or a fragment thereof having desaturase activity that desaturates a fatty acid molecule at carbon 15.

Still yet another aspect of the invention provides a method of producing seed oil containing omega-3 fatty acids from plant seeds, comprising the steps of (a) obtaining seeds of a plant according to the invention; and (b) extracting the oil from said seeds. Examples of such a plant seed include canola, soy, soybeans, rapeseed, sunflower, cotton, cocoa, peanut, safflower, coconut, flax, oil palm, oilseed *Brassica napus*, and corn. Preferred methods of transforming such plant cells include the use of Ti and Ri plasmids of *Agrobacterium*, electroporation, and high-velocity ballistic bombardment.

In still yet another aspect, a method is provided of producing a plant comprising seed oil containing altered levels of omega-3 fatty acids comprising introducing a recombinant vector of the invention into an oil-producing plant. In the method, introducing the recombinant vector may comprise plant breeding and may comprise the steps of: (a) transforming a plant cell with the recombinant vector; and (b) regenerating said plant from the plant cell, wherein the plant has altered levels of omega-3 fatty acids. In the method, the plant may, for example, be selected from the group consisting of *Arabidopsis thaliana*, oilseed *Brassica*, rapeseed, sunflower, safflower, canola, corn, soybean, cotton, flax, jojoba, Chinese tallow tree, tobacco, cocoa, peanut, fruit plants, citrus plants, and plants producing nuts and berries. The plant may be further defined as transformed with a nucleic acid sequence encoding a polypeptide having desaturase activity that desaturates a fatty acid molecule at carbon 6 and the plant may have SDA increased. The method may also further comprise introducing the recombinant vector into a plurality of oil-producing plants and screening the plants or progeny thereof having inherited the recombinant vector for a plant having a desired profile of omega-3 fatty acids.

In still yet another aspect, the invention provides an endogenous canola seed oil having a SDA content of from about 8% to about 27% and an oleic acid content of from about 40% to about 70%. In certain embodiments, the canola seed oil may be further defined as comprising less than 10% combined ALA acid, LA and GLA. The oil may also comprise a SDA content further defined as from about 10% to about 20%, including from about 12% to about 20%, about 15% to about 20%, about 10% to about 17% and about 12% to about 17%. In further embodiments of the invention, the canola seed oil may have an oleic acid content further defined as from about 45% to about 65%, including from about 50% to about 65%, from about 50% to about 60% and from about 55% to about 65%. In still further embodiments of the invention, the SDA content is further defined as from about 12% to about 17% and the oleic acid content is further defined as from about 55% to about 65%. In one embodiment of the invention, a canola seed oil is from *Brassica napus* or *Brassica rapa* seed. In certain embodiments, an oil provided has a ratio of omega-6 to omega-3 fatty acids of from about 1:1 to about 1:4, including from about 1:2 to about 1:4.

In still yet another aspect, the invention provides a method of increasing the nutritional value of an edible product for human or animal consumption, comprising adding a canola seed oil provided by the invention to the edible product. In certain embodiments, the product is human and/or animal food. The edible product may also be animal feed and/or a food supplement. In the method, the canola seed oil may increase the SDA content of the edible product and/or may decrease the ratio of omega-6 to omega-3 fatty acids of the edible product. The edible product may lack SDA prior to adding the canola seed oil.

In still yet another aspect, the invention provides a method of manufacturing food or feed, comprising adding a canola seed oil provided by the invention to starting food or feed ingredients to produce the food or feed. In certain embodiments, the method is further defined as a method of manufacturing food and/or feed. The invention also provides food or feed made by the method.

In still yet another aspect, the invention comprises a method of providing SDA to a human or animal, comprising administering the canola seed oil of claim 1 to said human or animal. In the method, the canola seed oil may be administered in an edible composition, including food or feed. Examples of food include beverages, infused foods, sauces, condiments, salad dressings, fruit juices, syrups, desserts, icings and fillings, soft frozen products, confections or intermediate food. The edible composition may be substantially a liquid or solid. The edible composition may also be a food supplement and/or nutraceutical. In the method, the canola seed oil may be administered to a human and/or an animal. Examples of animals the oil may be administered to include livestock or poultry.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein. The invention can be more fully understood from the following description of the figures:

Figure 6:
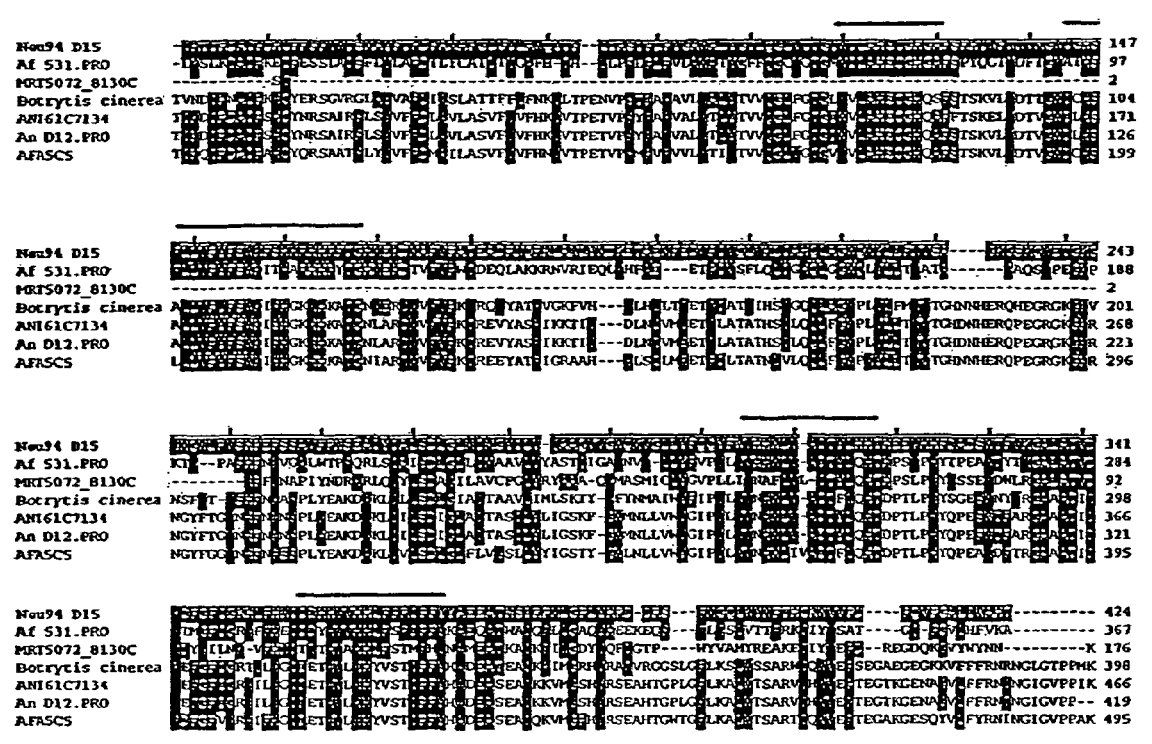

FIG. 6 shows a sequence alignment of exemplary desaturase polypeptides relative to N. crassa Δ15-desaturase.

DETAILED DESCRIPTION OF THE INVENTION

Figure 1:
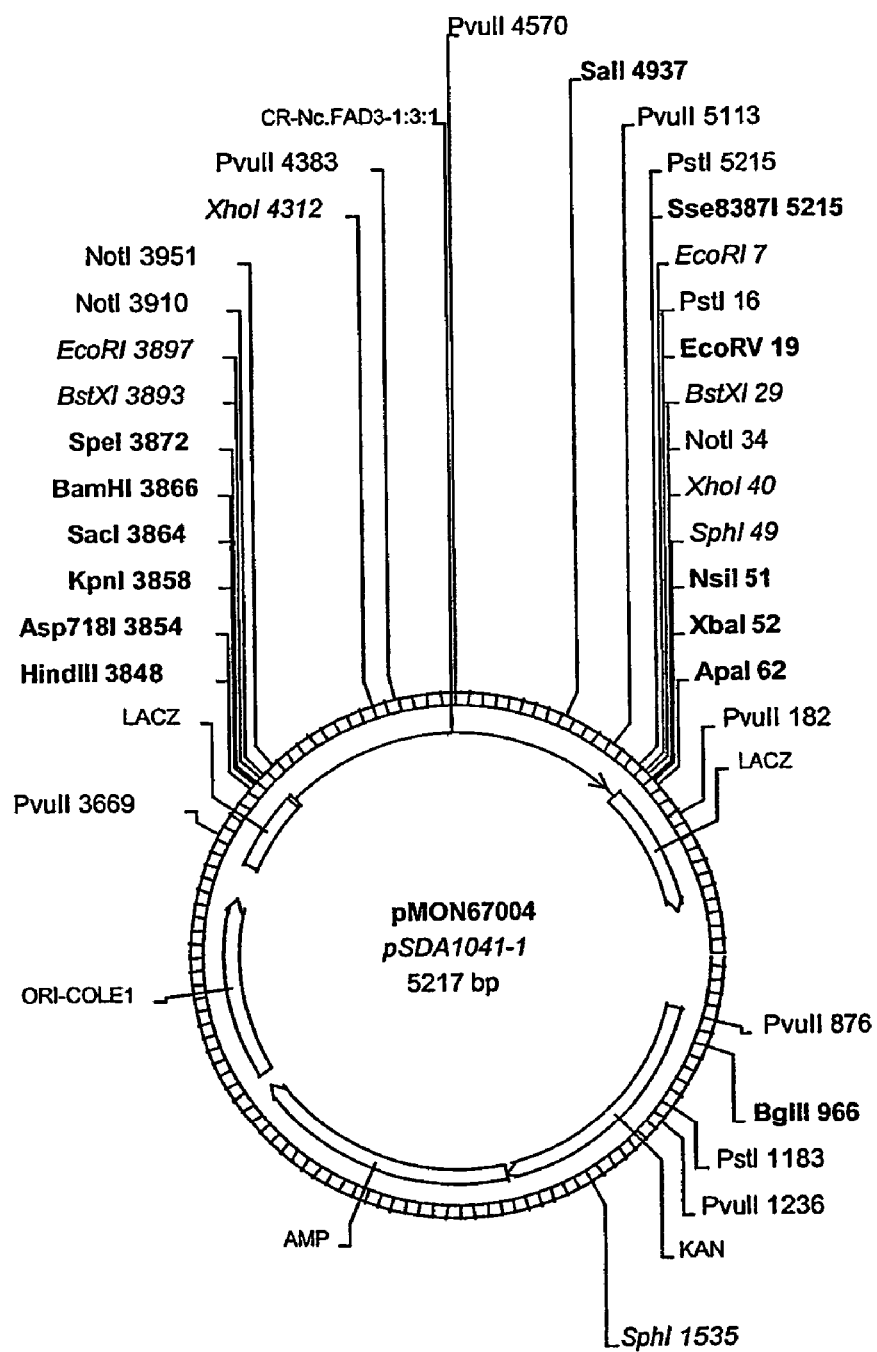
FIG. 1 shows the fungal Δ15-desaturase NcD15D coding region in a pCR2.1 cassette (pMON67004).

The invention overcomes the limitations of the prior art by providing methods and compositions for creation of plants with improved PUFA content. The modification of fatty acid content of an organism such as a plant presents many advantages, including improved nutrition and health benefits. Modification of fatty acid content can be used to achieve beneficial levels or profiles of desired PUFA's in plants, plant parts, and plant products, including plant seed oils. For example, when the desired PUFA's are produced in the seed tissue of a plant, the oil may be isolated from the seeds typically resulting in an oil high in desired PUFAs or an oil having a desired fatty acid content or profile, which may in turn be used to provide beneficial characteristics in food stuffs and other products. The invention in particular provides endogenous canola oil having SDA while also containing a beneficial oleic acid content.

Various aspects of the invention include methods and compositions for modification of PUFA content of a cell, for example, modification of the PUFA content of a plant cell(s). Compositions related to the invention include novel isolated polynucleotide sequences, polynucleotide constructs and plants and/or plant parts transformed by polynucleotides of the invention. The isolated polynucleotide may encode fungal fatty acid desaturases and, in particular, may encode a fungal Δ15-desaturase. Host cells may be manipulated to express a polynucleotide encoding a desaturase polypeptide(s) which catalyze desaturation of a fatty acid(s).

Some aspects of the invention include various desaturase polypeptides and polynucleotides encoding the same. Various embodiments of the invention may use a combinations of desaturase polynucleotides and the encoded polypeptides that typically depend upon the host cell, the availability of substrate(s), and the desired end product(s). "Desaturase" refers to a polypeptide that can desaturate or catalyze formation of a double bond between consecutive carbons of one or more fatty acids to produce a mono- or poly-unsaturated fatty acid or precursor thereof. Of particular interest are polypeptides which can catalyze the conversion of stearic acid to oleic acid, oleic acid to LA, LA to ALA, or ALA to SDA, which includes enzymes which desaturate at the 12, 15, or 6 positions. The term "polypeptide" refers to any chain of amino acids, regardless of length or post-translational modification (e.g., glycosylation or phosphorylation). Considerations for choosing a specific polypeptide having desaturase activity include, but are not limited to the pH optimum of the polypeptide, whether the polypeptide is a rate limiting enzyme or a component thereof, whether the desaturase used is essential for synthesis of a desired PUFA, and/or a co-factor is required by the polypeptide. The expressed polypeptide preferably has characteristics that are compatible with the biochemical environment of its location in the host cell. For example, the polypeptide may have to compete for substrate(s).

Analyses of the $K_m$ and specific activity of a polypeptide in question may be considered in determining the suitability of a given polypeptide for modifying PUFA(s) production, level, or profile in a given host cell. The polypeptide used in a particular situation is one which typically can function under the conditions present in the intended host cell, but otherwise may be any desaturase polypeptide having a desired characteristic or being capable of modifying the relative production, level or profile of a desired PUFA(s) or any other desired characteristics as discussed herein. The substrate(s) for the expressed enzyme may be produced by the host cell or may be exogenously supplied. To achieve expression, the polypeptide(s) of the instant invention are encoded by polynucleotides as described below.

The inventors have isolated and produced enzymes of fungal origin which exhibit Δ15-desaturase activity. Fungal sources include, but are not limited to the genus *Aspergillus*, e.g., *Aspergillus nidulans*; the genus *Botrytis*, e.g., *Botrytis cinerea*; the genus *Neurospora*, e.g., *Neurospora crassa*; and other fungi that exhibit Δ15-desaturase activity.

Of particular interest are *Neurospora crassa* and/or *Aspergillus nidulans* Δ15-desaturase(s). The amino acid sequence of the *N. crassa* Δ15-desaturase, set forth in SEQ ID NO:3 and encoded by the nucleotide sequence in SEQ ID NO:1 and SEQ ID NO:2, was determined to have a molecular weight of approximately 49,123.37 Daltons. The sequence consists of 429 amino acids; 32 of which are strongly basic (lysine, arginine); 35 of which are strongly acidic (aspartic acid, glutamic acid); 170 hydrophobic amino acids (alanine, isoleucine, leucine, phenylalanine, tryptophan, valine); and 100 polar amino acids (asparagine, cysteine, glutamine, serine, threonine, tyrosine). SEQ ID NO:3 has an isoelectric point of 7.187; a charge of 1.634 at pH 7.0; a Davis, Botsein, Roth Melting Temperature of 89.65° C. and a Wallace Temperature of 5098.00.

The amino acid sequence of the *A. nidulans* Δ15-desaturase, set forth in SEQ ID NO:5 and encoded by the nucleic acid sequence set forth in SEQ ID NO:4, was determined to have a molecular weight of approximately 46,300 Daltons. The sequence consists of 401 amino acids; of which 31 are strongly basic (lysine, arginine); 34 are strongly basic (aspartic acid, glutamic acid); 161 hydrophobic amino acids (alanine, isoleucine, leucine, phenylalanine, tryptophan, valine); and 100 polar amino acids (asparagine, cysteine, glutamine, serine, threonine, tyrosine). SEQ ID NO:5 has an isoelectric point of 6.83.

The sequences encoding the *Neurospora crassa* and/or the *Aspergillus nidulans* Δ15-desaturase may be expressed in transgenic plants, microorganisms or animals to effect greater synthesis of ALA from LA, as well as SDA. Other polynucleotides which are substantially identical to the *N. crassa* and/or the *A. nidulans* Δ15-desaturase polynucleotide, or which encode polypeptides which are substantially identical to the *N. crassa* and/or the *A. nidulans* Δ15-desaturase polypeptide, also can be used. "Substantially identical" refers to an amino acid sequence or nucleic acid sequence exhibiting in order of increasing preference at least 80%, 90% or 95% identity to the *N. crassa* and/or the *A. nidulans* Δ15-desaturase amino acid sequence or nucleic acid sequence encoding the amino acid sequence. Polypeptide or polynucleotide comparisons may be carried out using sequence analysis software, for example, the Sequence Analysis software package of theGCG Wisconsin Package (Accelrys, San Diego, Calif.), MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of similarity or identity.

Encompassed by the present invention are related desaturases from the same or other related organisms. Such related desaturases include variants of the disclosed Δ15-desaturases naturally occurring within the same or different species of fungus. Related desaturases can be identified by their ability to function substantially the same as the disclosed desaturases; that is, are still able to effectively convert LA to ALA and GLA to SDA. Related desaturases also can be identified by screening sequence databases for sequences homologous to the disclosed desaturases, by hybridization of a probe based on the disclosed desaturases to a library constructed from the source organism, or by RT-PCR using mRNA from the source organism and primers based on the disclosed desaturases.

Certain aspects of the invention include variants and fragments of a fungal Δ15-desaturase polypeptide and the nucleic acids encoding such that retain desaturase activity. In another aspect of the invention, a vector containing a nucleic acid, or fragment thereof, containing a promoter, a Δ15-desaturase coding sequence and a termination region may transferred into an organism in which the promoter and termination regions are functional. Accordingly, organisms producing recombinant Δ15-desaturase are provided by this invention. Yet another aspect of this invention provides isolated Δ15-desaturase, which can be purified from the recombinant organisms by standard methods of protein purification. (For example, see Ausubel et al., 1987).

Various aspects of the invention include nucleic acid sequences that encode desaturases, described herein. Nucleic acids may be isolated from fungi including, but not limited to *Neurospora crassa*, *Aspergillus nidulans*, *Botrytis cinerea* and the like. The genomes of these fungi have all been sequenced and it has been determined that each is rich in ALA. A cloning strategy based on oligonucleotide primers designed to amplify sequences identified as potential fatty acid desaturases, based on BLAST searches of the *N. crassa* genomic DNA database, may be used to sequence individual clones. These clones may then be functionally characterized.

Nucleic acid constructs may be provided that integrate into the genome of a host cell or are autonomously replicated (e.g., episomally replicated) in the host cell. For production of ALA and/or SDA, the expression cassettes, (i.e., a polynucleotide encoding a protein that is operatively linked to nucleic acid sequence(s) that directs the expression of the polynucleotide) generally used include an expression cassette which provides for expression of a polynucleotide encoding a Δ15-desaturase. In certain embodiments a host cell may have wild type oleic acid content.

Methods and compositions for the construction of expression vectors, when taken in light of the teachings provided herein, for expression of fungal desaturase enzymes will be apparent to one of ordinary skill in the art. Expression vectors, as described herein, are DNA or RNA molecules engineered for controlled expression of a desired polynucleotide, e.g., the Δ15-desaturase encoding polynucleotide. Examples of vectors include plasmids, bacteriophages, cosmids or viruses. Shuttle vectors, e.g. (Wolk et al. 1984; Bustos et al., 1991) are also contemplated in accordance with the present invention. Reviews of vectors and methods of preparing and using them can be found in Sambrook et al. (1989); Goeddel (1990); and Perbal (1988). Sequence elements capable of effecting expression of a polynucleotide include promoters, enhancer elements, upstream activating sequences, transcription termination signals and polyadenylation sites.

Polynucleotides encoding desaturases may be placed under transcriptional control of a strong promoter. In some cases this leads to an increase in the amount of desaturase enzyme expressed and concomitantly an increase in the fatty acid produced as a result of the reaction catalyzed by the enzyme. There is a wide variety of plant promoter sequences which may be used to drive tissue-specific expression of polynucleotides encoding desaturases in transgenic plants. For instance, the napin promoter and the acyl carrier protein promoters have previously been used in the modification of seed oil composition by expression of an antisense form of a desaturase (Knutzon et al. 1999). Similarly, the promoter for the β-subunit of soybean β-conglycinin has been shown to be highly active and to result in tissue-specific expression in transgenic plants of species other than soybean (Bray et al., 1987). Arondel et al. (1992) increased the amount of linolenic acid (18:3) in tissues of transgenic *Arabidopsis* plants by placing the endoplasmic reticulum-localized fad3 gene under transcriptional control of the strong constitutive cauliflower mosaic virus 35S promoter.

The ordinarily skilled artisan can determine vectors and regulatory elements (including operably linked promoters and coding regions) suitable for expression in a particular host cell. "Operably linked" in this context means that the promoter and terminator sequences effectively function to regulate transcription. As a further example, a vector appropriate for expression of Δ15-desaturase in transgenic plants can comprise a seed-specific promoter sequence derived from helianthinin, napin, or glycinin operably linked to the Δ15-desaturase coding region and further operably linked to a seed storage protein termination signal or the nopaline synthase termination signal. As a still further example, a vector for use in expression of Δ15-desaturase in plants can comprise a constitutive promoter or a tissue specific promoter operably linked to the Δ15-desaturase coding region and further operably linked to a constitutive or tissue specific terminator or the nopaline synthase termination signal.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

Standard techniques for the construction of such recombinant vectors are well-known to those of ordinary skill in the art and can be found in references such as Sambrook et al. (1989), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in a nucleic acid vector other nucleotide sequence elements which facilitate cloning, expression or processing, for example sequences encoding signal peptides, a sequence encoding KDEL, which is required for retention of proteins in the endoplasmic reticulum or sequences encoding transit peptides which direct Δ15-desaturase to the chloroplast. Such sequences are known to one of ordinary skill in the art. An optimized transit peptide is described, for example, by Van den Broeck et al. (1985). Prokaryotic and eukaryotic signal sequences are disclosed, for example, by Michaelis et al. (1982).

In certain embodiments, the expression cassettes may include a cassette which provides for Δ6- and/or Δ15-desaturase activity, particularly in a host cell which produces or can take up LA or ALA, respectively. Production of omega-6 type unsaturated fatty acids, such as LA, is favored in a host organism which is incapable of producing ALA. The host ALA production can be removed, reduced and/or inhibited by inhibiting the activity of a Δ15-desaturase. This can be accomplished by standard selection, providing an expression cassette for an antisense Δ15-desaturase, by disrupting a target Δ15-desaturase gene through insertion, deletion, substitution of part or all of the target gene, or by adding an inhibitor of Δ15-desaturase. Similarly, production of LA or ALA is favored in a microorganism or animal having Δ6-desaturase activity by providing an expression cassette for an antisense Δ6 transcript, by disrupting a Δ6-desaturase gene, or by use of a Δ6-desaturase inhibitor.

Polynucleotides encoding desired desaturases can be identified in a variety of ways. As an example, a source of the desired desaturase, for example genomic or cDNA libraries from *Neurospora*, is screened with detectable enzymatically- or chemically-synthesized probes, which can be made from DNA, RNA, or non-naturally occurring nucleotides, or mixtures thereof. Probes may be enzymatically synthesized from polynucleotides of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

Some or all of the coding sequence for a polypeptide having desaturase activity may be from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for function in the host cell, such as a longer half-life or a higher rate of production of a desired polyunsaturated fatty acid.

Once the polynucleotide encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the polynucleotide encoding the desaturase polypeptide. Expression of the polypeptide coding region can take place in vitro or in a host cell. Transcriptional and translational initiation and termination regions are derived from a variety of nonexclusive sources, including the polynucleotide to be expressed, genes known or suspected to be capable of expression in the desired system, expression vectors, chemical synthesis, or from an endogenous locus in a host cell.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source organism is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

It is contemplated that more than one polynucleotide encoding a desaturase or a polynucleotide encoding more than one desaturase may be introduced and propagated in a host cell through the use of episomal or integrated expression vectors. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced polynucleotides are expressed at the necessary levels to provide for synthesis of the desired products.

When necessary for transformation, the Δ15-desaturase coding sequences of the present invention can be inserted into a plant transformation vector, e.g. the binary vector described by Bevan (1984). Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

The subject invention finds many applications. Probes based on the polynucleotides of the present invention may find use in methods for isolating related molecules or in methods to detect organisms expressing desaturases. When used as probes, the polynucleotides or oligonucleotides must be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labeling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

Constructs comprising the gene of interest may be introduced into a host cell by standard techniques. For convenience, a host cell which has been manipulated by any method to take up a DNA sequence or construct will be referred to as "transformed" or "recombinant" herein. The subject host will have at least have one copy of the expression construct and may have two or more, for example, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host. Selection of a transformed host can also occur when the expressed marker protein can be detected, either directly or indirectly. The marker protein may be expressed alone or as a fusion to another protein. The marker protein can be detected by its enzymatic activity; for example, beta-galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies. Desirably, resistance to kanamycin and the amino glycoside G418 are of interest, as well as ability to grow on media lacking uracil, leucine, lysine or tryptophan.

Of particular interest is the Δ15-desaturase-mediated production of PUFA's in eukaryotic host cells. Eukaryotic cells include plant cells, such as those from oil-producing crop plants, and other cells amenable to genetic manipulation including fungal cells. The cells may be cultured or formed as part or all of a host organism including a plant. In a preferred embodiment, the host is a plant cell which produces and/or can assimilate exogenously supplied substrate(s) for a Δ15-desaturase, and preferably produces large amounts of one or more of the substrates.

The transformed host cell is grown under appropriate conditions adapted for a desired end result. For host cells grown in culture, the conditions are typically optimized to produce the greatest or most economical yield of PUFA's, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection.

Another aspect of the present invention provides transgenic plants or progeny of plants containing the isolated DNA of the invention. Both monocotyledonous and dicotyledonous plants are contemplated. Plant cells are transformed with an isolated DNA encoding Δ15-desaturase by any of the plant transformation methods described above. The transformed plant cell, usually in a callus culture or leaf disk, is regenerated into a complete transgenic plant by methods well-known to one of ordinary skill in the art (e.g. Horsch et al., 1985). In one embodiment, the transgenic plant is selected from the group consisting of *Arabidopsis thaliana*, canola, soy, soybean, rapeseed, sunflower, cotton, cocoa, peanut, safflower, coconut, flax, oil palm, oilseed *Brassica napes*, corn, jojoba, Chinese tallow tree, tobacco, fruit plants, citrus plants or plants producing nuts and berries. Since progeny of transformed plants inherit the polynucleotide encoding Δ15-desaturase, seeds or cuttings from transformed plants may be used to maintain the transgenic plant line.

The present invention further provides a method for providing transgenic plants with an increased content of ALA and/or SDA. This method includes, for example, introducing DNA encoding Δ15-desaturase into plant cells which lack or have low levels of ALA or SDA but contain LA, and regenerating plants with increased ALA and/or SDA content from the transgenic cells. In certain embodiments of the invention, a DNA encoding a Δ6- and/or Δ12-desaturase may also be introduced into the plant cells. Such plants may or may not also comprise endogenous Δ6- and/or Δ12-desaturase activity. In certain embodiments, modified commercially grown crop plants are contemplated as the transgenic organism, including, but not limited to, *Arabidopsis thaliana*, canola, soy, soybean, rapeseed, sunflower, cotton, cocoa, peanut, safflower, coconut, flax, oil palm, oilseed *Brassica napus*, corn, jojoba, Chinese tallow tree, tobacco, fruit plants, citrus plants or plants producing nuts and berries.

The present invention further provides a method for providing transgenic plants which may contain elevated levels of ALA and/or SDA, wherein said elevated levels are greater than levels found in non-transformed plants. This method may comprise introducing one or more polynucleotide encoding Δ15-desaturase into a plant which lacks or has low levels of ALA, but contains LA. Expression vectors comprising DNA encoding a Δ15-desaturase, or a Δ15-desaturase and a Δ6-desaturase, can be constructed by methods of recombinant technology known to one of ordinary skill in the art (Sambrook et al., 1989). In particular, commercially grown crop plants are contemplated as the transgenic organism, including, but not limited to, *Arabidopsis thaliana*, canola, soy, soybean, rapeseed, sunflower, cotton, cocoa, peanut, safflower, coconut, flax, oil palm, oilseed *Brassica napus*, and corn.

For dietary supplementation, the purified PUFAs, transformed plants or plant parts, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

As used herein, "edible composition" is defined as compositions which may be ingested by a mammal such as foodstuffs, nutritional substances and pharmaceutical compositions. As used herein "foodstuffs" refer to substances that can be used or prepared for use as food for a mammal and include substances that may be used in the preparation of food (such as frying oils) or food additives. For example, foodstuffs include animals used for human consumption or any product therefrom, such as, for example, eggs. Typical foodstuffs include but are not limited to beverages, (e.g., soft drinks, carbonated beverages, ready to mix beverages), infused foods (e.g. fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yogurts, soft frozen toppings such as dairy or non-dairy whipped toppings), oils and emulsified products (e.g., shortening, margarine, mayonnaise, butter, cooking oil, and salad dressings) and intermediate moisture foods (e.g., rice and dog foods).

Furthermore, edible compositions described herein can also be ingested as an additive or supplement contained in foods and drinks. These can be formulated together with a nutritional substance such as various vitamins and minerals and incorporated into substantially liquid compositions such as nutrient drinks, soymilks and soups; substantially solid compositions; and gelatins or used in the form of a powder to be incorporated into various foods. The content of the effective ingredient in such a functional or health food can be similar to the dose contained in a typical pharmaceutical agent.

The purified PUFAs, transformed plants or plant parts may also be incorporated into animal, particularly livestock, feed. In this way, the animals themselves may benefit from a PUFA rich diet, while human consumers of food products produced from such livestock may benefit as well. It is expected in certain embodiments that SDA will be converted to EPA in animals and thus such animals may benefit from an increase in EPA by consumption of SDA.

For pharmaceutical use (human or veterinary), the compositions may generally be administered orally but can be administered by any route by which they may be successfully absorbed, e.g., parenterally (i.e. subcutaneously, intramuscularly or intravenously), rectally, vaginally or topically, for example, as a skin ointment or lotion. The PUFAs transformed plants or plant parts of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids.

If desired, the regions of a desaturase polypeptide important for desaturase activity can be determined through routine mutagenesis followed by expression of the resulting mutant polypeptides and determination of their activities. Mutants may include substitutions, deletions, insertions and point mutations, or combinations thereof. Substitutions may be made on the basis of conserved hydrophobicity or hydrophilicity byte and Doolittle, 1982), or on the basis of the ability to assume similar polypeptide secondary structure (Chou and Fasman, 1978). A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites.

Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR. Chemical mutagenesis may also be used for identifying regions of a desaturase polypeptide important for activity. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

As described herein above, certain embodiments of the current invention concern plant transformation constructs. For example, one aspect of the current invention is a plant transformation vector comprising one or more desaturase gene(s) or cDNA(s). Exemplary coding sequences for use with the invention include *Neurospora crassa* gene Δ15-desaturase NcD15D (SEQ ID NO:1 and SEQ ID NO:2) and *Aspergillus nidulans* Δ15-desaturase AnD15D (SEQ ID NO:4). In certain embodiments, antisense desaturase sequences can also be employed with the invention. Exemplary desaturase encoding nucleic acids include at least 20, 40, 80, 120, 300 and up to the full length of the nucleic acid sequences of SEQ ID NO:1, SEQ ID NO:2, SEQ ID NO:4 or SEQ ID NO:33 may be used. In certain aspects, a nucleic acid may encode 1, 2, 3, 4, or more desaturase enzymes. In particular embodiments, a nucleic acid may encode a Δ6- and a Δ15-desaturase.

In certain embodiments of the invention, coding sequences are provided operably linked to a heterologous promoter, in either sense or antisense orientation. Expression constructs are also provided comprising these sequences, as are plants and plant cells transformed with the sequences. The construction of constructs which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One use of the sequences provided by the invention will be in the alteration of plant phenotypes, e.g., oil composition, by genetic transformation with desaturase genes, in particular embodiments a fungal Δ15-desaturase. The desaturase gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the desaturase coding sequences will often depend on the purpose of the transformation. One of the major purposes of transformation of crop plants is to add commercially desirable, agronomically important traits to the plant. As PUFAs are known to confer many beneficial effects on health, concomitant increases in SDA production may also be beneficial and could be achieved by expression of fungal Δ15-desaturase. Such increasing of SDA may, in certain embodiments of the invention, comprise expression of Δ6 and/or Δ12 desaturase, including fungal or plant Δ6 and/or Δ12 desaturases.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce various desaturase encoding nucleic acids. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

In one embodiment the instant invention utilizes certain promoters. Examples of such promoters that may be used with the instant invention include, but are not limited to, the 35S CaMV (cauliflower mosaic virus), 34S FMV (figwort mosaic virus) (see, e.g., U.S. Pat. No. 5,378,619, the contents of which are herein incorporated in their entirety), Napin (from *Brassica*), 7S (from soybean), Glob and Lec (from corn). The 35S CaMV promoter and promoters, which are regulated during plant seed maturation, are of particular interest for use with the instant invention. All such promoter and transcriptional regulatory elements, singly or in combination, are contemplated for use in the present replicable expression vectors and are known to one of ordinary skill in the art.

The CaMV 35S promoter is described, for example, by Restrepo et al. (1990). Genetically transformed and mutated regulatory sequences which lead to seed-specific expression may also be employed for the production of modified seed oil composition. Such modifications of the invention described here will be obvious to one skilled in the art.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

Transformation constructs prepared in accordance with the invention will typically include a 3' end DNA sequence that acts as a signal to terminate transcription and allow for the poly-adenylation of the mRNA produced by coding sequences operably linked to a desaturase gene (e.g., cDNA). In one embodiment of the invention, the native terminator of a desaturase gene is used. Alternatively, a heterologous 3' end may enhance the expression of desaturase coding regions. Examples of terminators deemed to be useful include those from the nopaline synthase gene of *Agrobacterium tumefaciens* (nos 3' end) (Bevan et al., 1983), the terminator for the T7 transcript from the octopine synthase gene of *Agrobacterium tumefaciens*, the 3' end of the protease inhibitor I or II genes from potato or tomato and the CaMV 35S terminator (tml3'). Regulatory elements such as an Adh intron (Callis et al., 1987), sucrose synthase intron (Vasil et al., 1989) or TMV omega element (Gallie et al., 1989), may further be included where desired.

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to maturation of embryoids. Cultures are transferred every 2 weeks on this medium. Shoot development will signal the time to transfer to medium lacking growth regulators.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

In addition to direct transformation of a particular plant genotype with a construct prepared according to the current invention, transgenic plants may be made by crossing a plant having a selected DNA of the invention to a second plant lacking the DNA. Plant breeding techniques may also be used to introduce a multiple desaturases, for example Δ6, Δ12, and/or Δ15-desaturase(s) into a single plant. In this manner, Δ15-desaturase can be effectively up-regulated. By creating plants homozygous for a Δ15-desaturase activity and/or other desaturase activity (e.g., Δ6- and/or Δ12-desaturase activity) beneficial metabolites can be increased in the plant.

As set forth above, a selected desaturase gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

EXAMPLES

The following examples are included to illustrate embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Strains and Growth Conditions

*Neurospora crassa* mating type A and *Aspergillus nidulans* Glasgow wild type were obtained from the Fungal Genetics Stock Center. Cultures were grown in Vogel's medium N. (Case et al., Neurospora Newsletter, 8:25-26, 1965). Liquid cultures were inoculated with ascospores and grown for three days at 15°~C. with shaking at 100 RPM. Mycelium was harvested by filtration in a Buchner funnel through Whatman number 1 paper and stored at 80° C. for RNA isolation or directly lyophilized for fatty acid composition determination by gas chromatography. The *Saccharomyces cerevisiae* strain used was INVSc1, a diploid strain that is auxotrophic for histidine, leucine, tryptophan, and uracil (Invitrogen). Cells were maintained on YPD media at 30° C.

Example 2

Isolation of Fungal RNA

Total RNA was isolated from fungal mycelium of the 3 strains described in Example 1 using the acid guanidinium-phenol-chloroform method of Chomczynski and Sacchi, (1987, Tri-Reagent, SIGMA). This method provides 500 mg of mycelium being ground in liquid nitrogen then added to 7 ml of Tri-Reagent. Chloroform was added to separate the aqueous phase from the organic phase. The RNA was precipitated with isopropanol then washed with 70% ethanol before being resuspended in deionized water.

Example 3

Cloning of the *N. crassa* Δ12 and Δ15-Desaturase Sequences

Based on sequence comparisons to the *N. crassa* genomic sequences, gene specific primers were designed to amplify the full-length coding regions of the putative Δ12-desaturase (Nc111F2 and Nc111R3) and the putative Δ15-desaturase (Nc94F6 and Nc94R8). Forward primers were designed to include three nucleotides 5' of the start Met site

```
                                                  (SEQ ID NO:15)
Nc111F2: 5'-AAGATGGCGTCCGTCTCCTCTGCCCTTCCC-3'

(SEQ ID NO:16)
Nc111R3: 5'-TTAGTTGGTTTTGGGGAGCTTGGCAGGCTTG-3'

(SEQ ID NO:17)
Nc94F6:  5'-GCGGCCGCAACATGACGGTCACCACCCGCAGCCA-3'.
```

The NotI site added to the 5' end of the oligonucleotide is italicized.

Nc94R8: 5'-*CCTGCAGG*TTACTGGGTGCTCTGAACGGTGTGCG-3'. (SEQ ID NO:18)

The Sse83871 site added to the 5' end of the oligonucleotide is italicized.

The cDNA for *N. crassa* was prepared using the Marathon cDNA Amplification kit (Clontech Laboratories). These primers were used with 3'-RACE ready cDNA to amplify putative desaturases using a Gene Amp PCR system 9700 (PE Applied Biosystems) with the recommended cycle conditions. The PCR product generated with oligonucleotides Nc94F6 and Nc94R8 was ligated into pCR2.1-TOPO (Invitrogen) and named pMON67004 (FIG. 1). The cDNA was sequenced and three "His-boxes", a conserved feature among membrane-bound desaturases, were found to be present at amino acid positions 124-128, 160-164, and 359-363.

Figure 2:
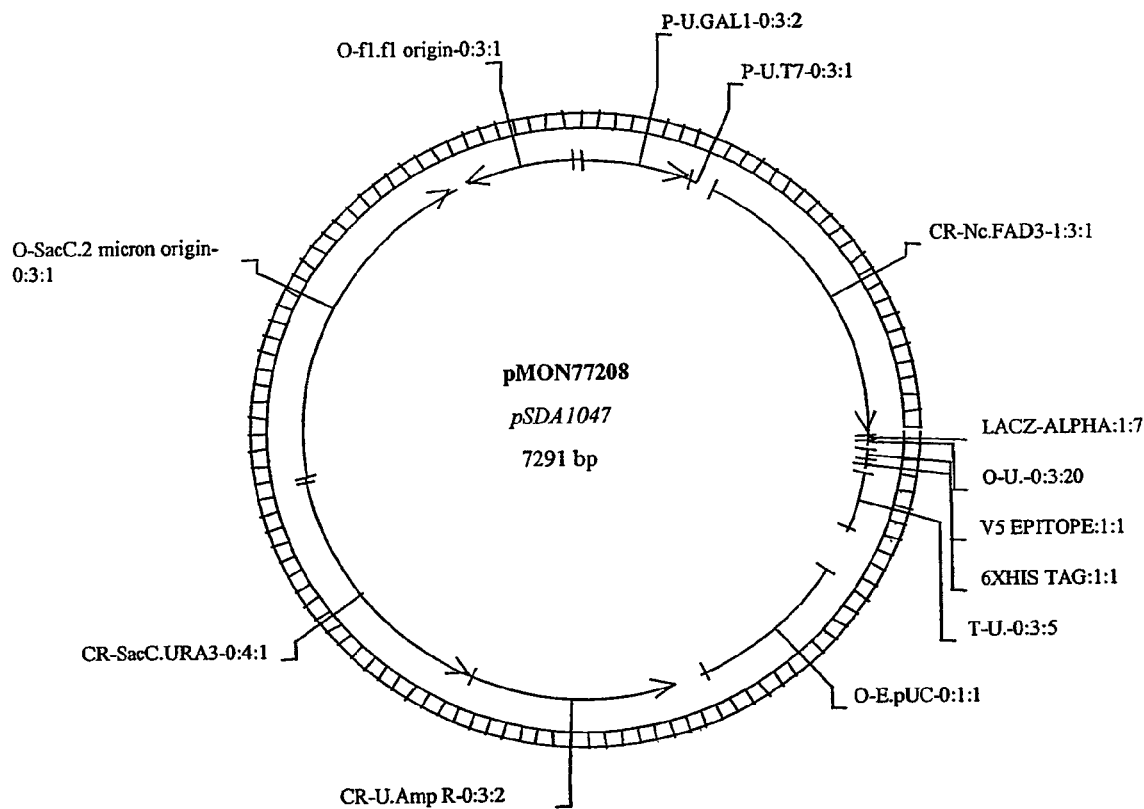
FIG. 2 shows the fungal Δ15-desaturase NcD15D coding region in the yeast expression vector pYES 2.1 (pMON77208).
Figure 4:
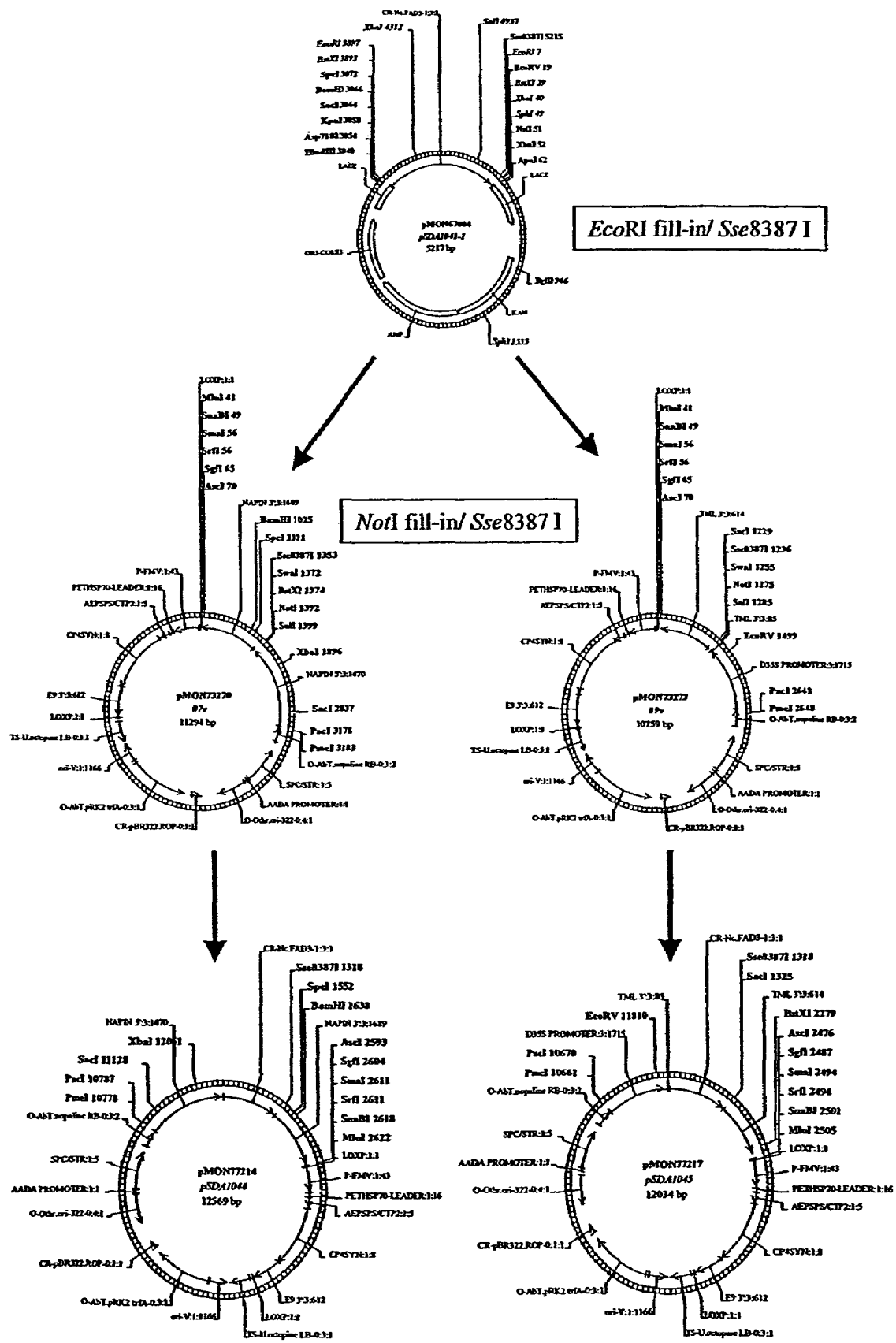
FIG. 4 shows a flow chart or plasmids maps resulting in plasmids pMON77214 and pMON77217.
Figure 5:
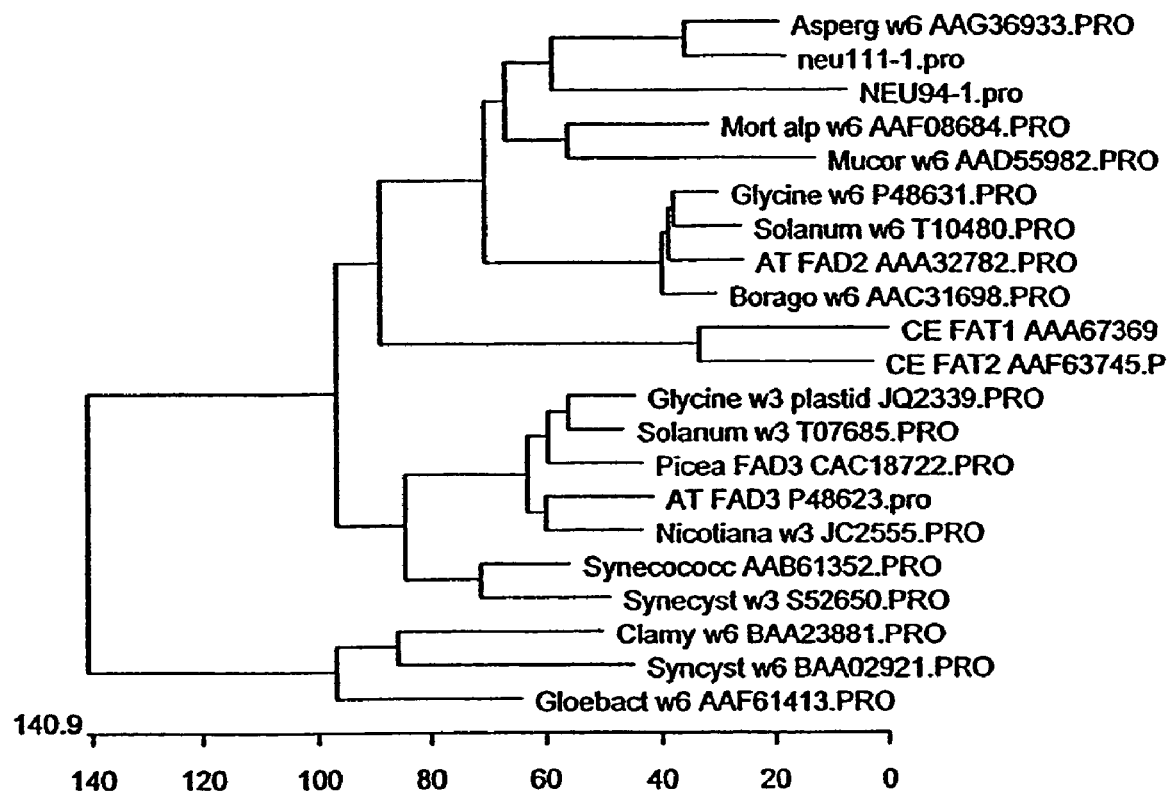
FIG. 5 shows an exemplary dendrogram of desaturase polypeptides, including N. crassa Δ15-desaturase.

When compared to other membrane-bound Δ12 and Δ15-desaturases, the final "HXXHH" histidine box motif was found to be intact as well. The corresponding nucleotide and polypeptide sequences for the Δ15-desaturase (NcD15D) are given in SEQ ID NO:2 and SEQ ID NO:3, respectively, and the genomic clone is given in SEQ ID NO: 1. pMON67004 was digested with EcoR1 and ligated into the EcoR1 site of the yeast expression vector pYES2/CT to generate pMON77208 (FIG. 2). For the plant transformation vectors, pMON67004 was digested with EcoRI, followed by a fill-in reaction, and then cut by Sse8387I. The gene fragment was ligated into the binary vector, pMON73270, which was digested by NotI, followed by a fill-in reaction, and then by Sse83871. This gave rise to vector pMON77214 (FIG. 4) in which the Δ15-desaturase gene, NcD15D, was under regulation of the seed-specific Napin promoter. The EcoRI/Sse8387I-digested DNA fragment was also ligated into the binary vector, pMON73273, giving rise to pMON77217 (FIG. 4), in which NcD15D was under regulation of the constitutive 35S promoter.

Figure 7A:
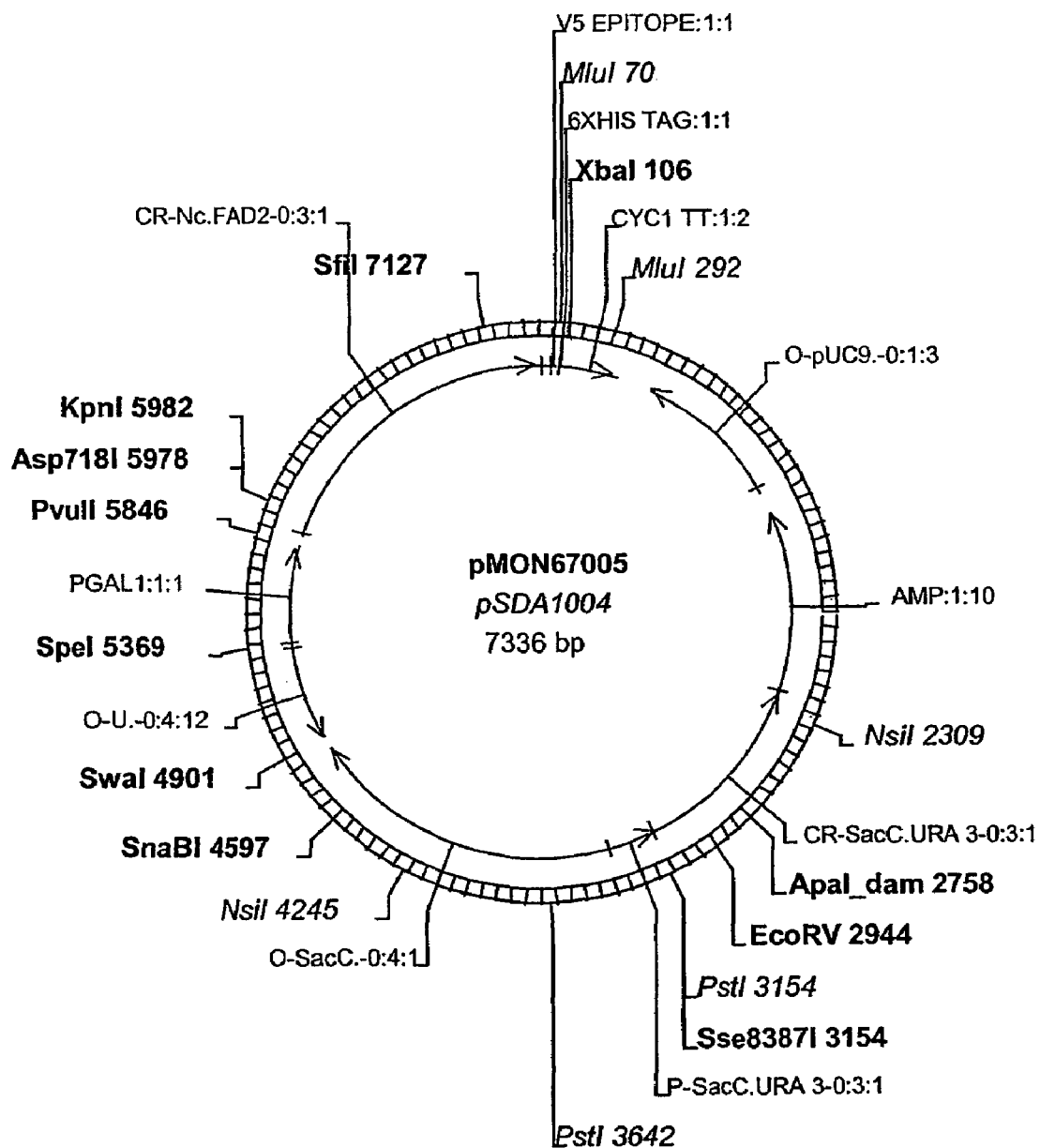
FIG. 7A-7G shows plasmid maps of constructs prepared.

The PCR product generated with oligonucleotides Nc111F2 and Nc111R3 was ligated directly into pYES2.1/V5-His-TOPO (Invitrogen) to generate pMON67005 (FIG. 7A). The cDNA was sequenced and three "His-boxes" were found to be present at amino acid positions 158-162, 194-198, and 394-398. When compared to other membrane-bound Δ12 and Δ15-desaturases, the final "HXXHH" histidine box motif was found to be intact as well. The corresponding nucleotide and polypeptide sequences for the putative Δ12-desaturase (NcD12D) are given in SEQ ID NO:39 and SEQ ID NO:40, respectively.

Example 4

Yeast Transformation and Expression

Constructs pMON67005 and pMON77208 were introduced into the host strain *S. cerevisiae* INVSc1 (auxotrophic for uracil) using the PEG/Li Ac protocol as described in the Invitrogen manual for pYES2.1/V5-His-TOPO. Transformants were selected on plates made of SC minimal media minus uracil with 2% glucose. Colonies of transformants were used to inoculate 5 ml of SC minimal media minus uracil and 2% glucose grown overnight at 30° C. For induction, stationary phase yeast cells were pelleted and resuspended in SC minimal media minus uracil supplemented with 2% galactose and grown for 3 days at 15° C. When exogenous fatty acids were provide to the cultures, 0.01% LA (Δ9,12-18:2) was added with the emulsifier 0.1% Tergitol. The cultures were grown for 3 days at 15° C., and subsequently harvested by centrifugation. Cell pellets were washed once with sterile TE buffer pH 7.5, to remove the media, and lyophilized for 24 h. The host strain transformed with the vector containing the LacZ gene was uses as a negative control in all experiments.

For fatty acid analysis, the extraction of the yeast lipids followed the procedures described previously. Briefly, lyophilized yeast pellets were extracted with 15 mL of methanol and 30 mL of chloroform containing 100 μg of tridecanoin. After extraction, the yeast lipids were first saponified, and the liberated fatty acids were methylated. The distribution of fatty acid methyl esters was then analyzed by gas chromatography (GC) using a Hewlett-Packard 5890 II Plus gas chromatograph (Hewlett-Packard, Palo Alto, Calif.) equipped with a flame-ionization detector and a fused-silica capillary column (Supelcomega; 50 m×0.25 mm, i.d., Supelco, 15 Bellefonte, Pa.).

In yeast transformed with the expression vector containing LacZ as a control, no LA or ALA (18:3) was measured in lines grown in the absence of added LA. In yeast transformed with an expression vector containing NcD15D or BnD15D, in the absence of added LA, no ALA accumulated. In yeast transformed with an expression vector containing NcD12D, without added LA, LA accumulated to 22% of the fatty acids, indicative of D12D activity. When LA was added to the yeast line expressing NcD15D, ALA compromised 1% of the fatty acids. In the yeast line expressing the *Brassica napus* Δ15-desaturase BnD15D), ALA compromised 0.2% of the fatty acids after addition of LA. In the LacZ control, no ALA was detected after LA addition.

TABLE 1

Yeast Expression Data

| Construct | Identity | FA Substrate Added | % Fatty Acids in Yeast | | | | | |
|---|---|---|---|---|---|---|---|---|
| | | | 16:0% | 16:1% | 18:0% | 18:1% | 18:2% | 18:3% |
| pMON77208 | NcD15D | none | 13.96 | 48.33 | 5.06 | 29.07 | 0.02 | 0.02 |
| pMON67003 | BnD15D | none | 13.22 | 48.15 | 5.18 | 29.82 | 0.00 | 0.00 |
| PMON67005 | NcD12D | none | 15.24 | 47.95 | 5.18 | 10.3 | 22.3 | 0 |
| LacZ | LacZ | none | 14.01 | 49.61 | 5.27 | 27.29 | 0.02 | 0.01 |
| pMON77208 | NcD15D | 18:2 | 18.34 | 25.98 | 5.94 | 16.09 | 30.30 | 1.04 |
| pMON67003 | BnD15D | 18:2 | 18.45 | 26.19 | 5.91 | 16.26 | 30.61 | 0.20 |
| LacZ | LacZ | 18:2 | 19.26 | 18.87 | 6.00 | 10.82 | 42.47 | 0.01 |

Example 5

Arabidopsis Transformation with NcD15D

This example describes the transformation and regeneration of transgenic *Arabidopsis thaliana* plants expressing a heterologous Δ15-desaturase coding sequence. *Arabidopsis* plants were grown by sowing seeds into 4 inch pots containing reverse osmosis water (ROW) and saturated MetroMix 200 (The SCOTTS Co., Columbus, Ohio). The plants were vernalized by placing the pots in a flat, covered with a humidity dome, in a growth chamber at 4-7° C., 8 hours light/day for 4-7 days. The flats were transferred to a growth chamber at 22° C., 55% relative humidity, and 16 hours light/day at an average intensity of 160-200 ~Mol/sec*m². After germination, the dome was lifted and slid back 1" to allow for mild air circulation without desiccation. The humidity dome was removed when the true leaves had formed. The plants were bottom watered, as needed, with ROW until 2-3 weeks after germination. Plants were then bottom watered, as needed, with PLANTEX 18-18-15 solution (Plantex Corporation Ottawa, Canada) at 50 ppm $N_2$. Pots were thinned so that 1 plant remained per pot at 2-3 weeks after germination. Once the plants began to bolt, the primary inflorescence was trimmed to encourage the growth of axillary bolts.

The transformation vectors pMON77214 and pMON77217 were introduced into *Agrobacterium tumefaciens* strain ABI using methodology well known in the art. Transgenic *A. thaliana* plants were obtained as described by Bent et al. (1994) or Bechtold et al. (1993). Briefly, cultures of *Agrobacterium* containing binary vectors pMPON77214 or pMON77217, were grown overnight in LB (10% bacto-tryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet-77. The aerial portion of whole *A. thaliana* plants (~5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants reached maturity, water was withheld for 2-7 days prior to seed harvest. Harvested seed was passed through a stainless steel mesh screen.

To select transformants, seed was plated on agar medium containing 50 mg/L glyphosate. Green seedlings were rescued and transplanted into 4" pots and grown under the conditions described above. Leaves were harvested for fatty acid analysis when the rosette was at the 4-leaf stage. After lyophylization, leaf fatty acids were analyzed as described above.

Example 6

Functional Expression of *N. crassa* Clones

In order to assess the functional specificity of the *N. crassa* D15D clone, the coding region from pMON67004 was cloned into a plant expression vector in which the constitutive 35S promoter drives expression of the transgene. The resulting construct, pMON77217, was transformed into *A. thaliana* and leaves of transformed T2 plants were analyzed for fatty acid composition. In non-transformed lines, approximately 20% of the fatty acids were LA, and approximately 48% ALA. In two independent *A. thaliana* transformation events, LA levels were reduced to approximately 3% and 5%, and ALA levels increased to 65% and 63%, respectively, indicating Δ15-desaturase activity in planta. These data are summarized in Table 2. Controls are designated as CONT.

TABLE 2

Fatty Acid Content of *Arabidopsis* Leaves

| EVENT | 16:0 | 16:1 | 18:0 | 18:1 | 18:2 (LA) | 18:3 (ALA) |
|---|---|---|---|---|---|---|
| CONT 1 | 14.9 | 0.8 | 1.4 | 4.8 | 19.7 | 48.2 |
| CONT 2 | 15.3 | 0.9 | 1.4 | 5.1 | 20.5 | 49.2 |
| CONT 3 | 14.5 | 0.9 | 1.4 | 5.1 | 19.6 | 49.5 |
| ATG174 | 15.6 | 1.0 | 1.6 | 4.6 | 15.4 | 51.9 |
| AT G717 | 15.3 | 0.7 | 1.4 | 4.2 | 17.9 | 52.1 |
| AT G716 | 14.9 | 0.6 | 1.6 | 3.1 | 15.8 | 55.1 |
| ATG718 | 15.3 | 0.8 | 1.8 | 4.0 | 5.4 | 63.7 |
| AT G709 | 17.0 | 0.9 | 1.9 | 4.3 | 3.5 | 64.0 |

In order to assess the functional specificity of the *N. crassa* D15D clone to direct production of ALA in seeds, the coding region of pMON67004 was cloned into a seed-specific expression vector in which the Napin promoter drives expression of the transgene. The resulting construct, pMON77214, was transformed into *A. thaliana* and seeds of transformed T2 plants were analyzed for fatty acid composition. In non-transformed lines, approximately 26% of the seed lipids was present as LA, and approximately 18% as ALA. In two independent *A. thaliana* transformation events, LA acid levels were reduced to approximately. 14% and 13%, and ALA acid levels increased to 26% and 30%, respectively, indicating Δ15-desaturase activity in seeds. These data are shown in Table 3.

TABLE 3

Fatty Acid Content of *Arabidopsis* Seeds

| EVENT | 16:0 | 16:1 | 18:0 | 18:1 | 18:2 (LA) | 18:3 (ALA) |
|---|---|---|---|---|---|---|
| Control | 6.86 | 0.39 | 2.94 | 14.7 | 27.95 | 17.75 |
| Control | 7.11 | 0.37 | 3.33 | 15.22 | 26.48 | 18.11 |
| G709 | 7.1 | 0.37 | 3.13 | 13.16 | 24.58 | 20.85 |
| G711 | 7.08 | 0.37 | 3.16 | 13.49 | 24.24 | 21.07 |
| G705 | 7.75 | 0.38 | 3.09 | 12.62 | 19.26 | 26.3 |
| G707 | 8.12 | 0.36 | 2.98 | 14.2 | 15.71 | 29.74 |

These results indicate that the protein encoded by the *Neurospora* NcD15D cDNA is a functional Δ15-desaturase in plants and can direct synthesis of ALA in leaves and in seeds.

Example 7

Activity of the *Neurospora crassa* Δ15-Desaturase in Canola

Lines were transformed with construct pMON77214, which contains the *Neurospora* Δ15-desaturase driven by the Napin promoter. Both Quantum and Ebony canola varieties were transformed and controls for both varieties included. Data shown in Table 4 is percent 18:2 (LA) and 18:3 (ALA) in pools of 20 seeds from $R_0$ plants.

TABLE 4

Percent PUFAs in Pools of 20 Seeds from $R_0$ Plants.

| STRAIN ID | 18:2 (LA) | 18:3 (ALA) |
|---|---|---|
| EBONY | 19.78 | 5.94 |
| EBONY | 18.13 | 7.51 |

TABLE 4-continued

Percent PUFAs in Pools of 20 Seeds from R₀ Plants.

| STRAIN ID | 18:2 (LA) | 18:3 (ALA) |
|---|---|---|
| EBONY | 19.46 | 7.56 |
| QUANTUM | 22.51 | 11.09 |
| QUANTUM | 23.39 | 11.17 |
| EBONY | 19.11 | 11.49 |
| QUANTUM | 23.05 | 12.03 |
| QUANTUM | 21.04 | 12.27 |
| BN_G1289 | 12.48 | 12.53 |
| BN_G1248 | 12.55 | 13.31 |
| BN_G1275 | 12.67 | 13.45 |
| BN_G1256 | 9.33 | 13.7 |
| BN_G1251 | 12.3 | 13.89 |
| BN_G1311 | 10.07 | 14.08 |
| BN_G1282 | 11.41 | 14.69 |
| BN_G1321 | 8.98 | 14.83 |
| BN_G1317 | 11.17 | 14.84 |
| BN_G1283 | 10.54 | 15.05 |
| BN_G1281 | 11.66 | 15.24 |
| BN_G1272 | 8.12 | 15.71 |
| BN_G1312 | 10.36 | 15.9 |
| BN_G1249 | 15.65 | 16.09 |
| BN_G1270 | 10.46 | 16.48 |
| BN_G1271 | 9.45 | 16.48 |
| BN_G1322 | 9.57 | 16.61 |
| BN_G1347 | 7.18 | 17.15 |
| BN_G1353 | 9.84 | 17.17 |
| BN_G1348 | 15.69 | 17.27 |
| BN_G1323 | 7.33 | 17.52 |
| BN_G1287 | 5.95 | 17.53 |
| BN_G1318 | 11 | 17.96 |
| BN_G1389 | 13.72 | 18 |
| BN_G1295 | 10.46 | 18.03 |
| BN_G1319 | 7.53 | 18.44 |
| BN_G1286 | 7.88 | 19.11 |
| BN_G1316 | 5.67 | 19.32 |
| BN_G1355 | 9.86 | 19.38 |
| BN_G1400 | 14.17 | 19.4 |
| BN_G1354 | 6.4 | 19.72 |
| BN_G1285 | 8.97 | 19.77 |
| BN_G1392 | 8.71 | 19.84 |
| BN_G1385 | 9.53 | 19.89 |
| BN_G1288 | 7.88 | 20.04 |
| BN_G1386 | 14.81 | 20.16 |
| BN_G1250 | 3.78 | 20.28 |
| BN_G1393 | 10.49 | 20.55 |
| BN_G1280 | 5.81 | 20.63 |
| BN_G1315 | 8.82 | 20.76 |
| BN_G1329 | 8.21 | 20.77 |
| BN_G1328 | 3.71 | 21.09 |
| BN_G1279 | 5.47 | 21.18 |
| BN_G1387 | 11.1 | 21.32 |
| BN_G1284 | 4.28 | 21.33 |
| BN_G1447 | 7.7 | 21.76 |
| BN_G1401 | 4.97 | 21.82 |
| BN_G1298 | 9.7 | 21.99 |
| BN_G1297 | 7.4 | 22.15 |
| BN_G1350 | 5.41 | 23.5 |
| BN_G1405 | 7.86 | 23.73 |
| BN_G1390 | 7.74 | 24.52 |
| BN_G1351 | 9.05 | 24.78 |
| BN_G1398 | 6.24 | 24.82 |
| BN_G1296 | 4.05 | 25.04 |
| BN_G1394 | 7.43 | 27.34 |
| BN_G1395 | 9.8 | 30.17 |

The production of ALA at levels greater than ~12% of seed fatty acids in these lines was indicative of the heterologous Δ15-desaturase activity. The highest level of ALA observed from this transformation was in line BN_G1395, which contains 30.17% ALA.

Figure 3:
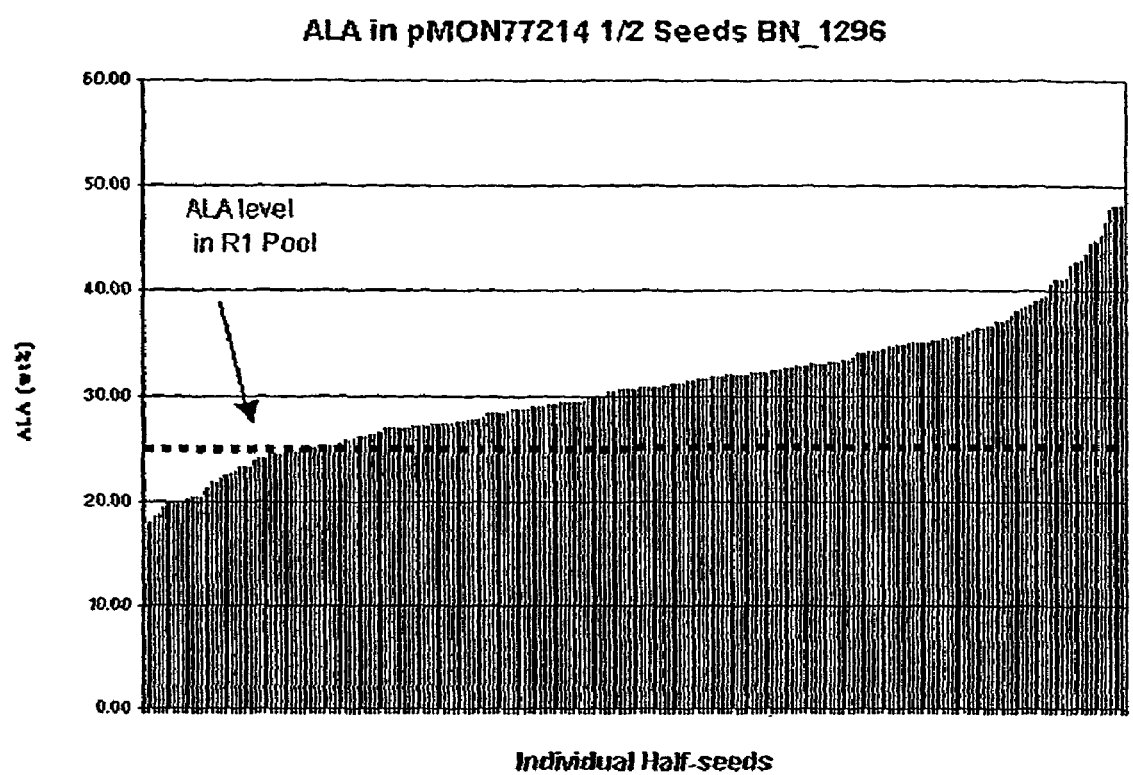
FIG. 3 shows the ALA levels in 200 half-seeds (seeds cut in half), ordered from lowest to highest ALA.

For several of the lines expressing pMON77214, fatty acids in single seeds were determined and lines advanced to the next generation. As expected, ALA levels increased up to nearly 2-fold in individual seeds relative to the pools, indicative of homozygosity for the transgenes in individual segregants within each silique. In line BN_1296, Pooled R1 seed contained 25.04% ALA. In the highest single seed from this line (BN_G1296-14), 48.2% ALA was observed. The ALA levels in 200 half-seeds, ordered from lowest to highest ALA, is shown in FIG. 3.

Example 8

Cloning of the Δ15-desaturase Sequence from *A. nidulans* and the Δ12- and Δ15Desaturase Sequences from *B. cinerea*

Based on sequence comparisons to the *A. nidulans* genomic sequence, gene specific primers were designed to amplify the full-length coding regions of the putative Δ15-desaturase (AnD15-F1 and AnD15-R1). The forward primer was designed to include three nucleotides 5' of the start Met site (SEQ ID NO:23)
AnD15-F1: 5'-AATATGGCTGCAACTGCAACAACCC-3'

(SEQ ID NO:24)
AnD15-R1: 5'-TTCCGCTTGGCACCCTTCTTC-3'

Oligonucleotide primers BcD12F1 and BcD12R1 were designed from a partial genomic sequence (Monsanto proprietary partial gDNA clone found with BLASTALL) to amplify the full-length coding regions of *B. cinerea* Δ12-desaturase. The degenerate primer D15D-R9 was designed to amplify any putative *B. cinerea* Δ15-desaturase in a 5'-RACE reaction. Oligonucleotide BCD15-F1 was designed for a 3' RACE reaction of the PCR product generated from oligonucleotide D15D-R9. Oligonucleotides BcD15F3 and BcD15R1F were designed to amplify the full-length coding region of a putative *B. cinerea* Δ15-desaturase.

(SEQ ID NO:25)
BcD12F1: 5'-GTCGACACCATGGCCTCTACCACTGCTCTC-3',
5' end contains SalI-3'.

(SEQ ID NO:26)
BcD12R1: 5'-CTGCAGTGCCTTGAGCTTCATTGGTGGTGTA-3',
5' end contains PstI (SEQ ID NO:27)
D15D-R9: 5'-GCCRTGNCCRCAYTCRTGNGCNAGDAT-3'

(SEQ ID NO:28)
BcD15-F1: 5'-ACGATGACTCTCGATTACACAAGTCACCCG-3'

Figure 7B:
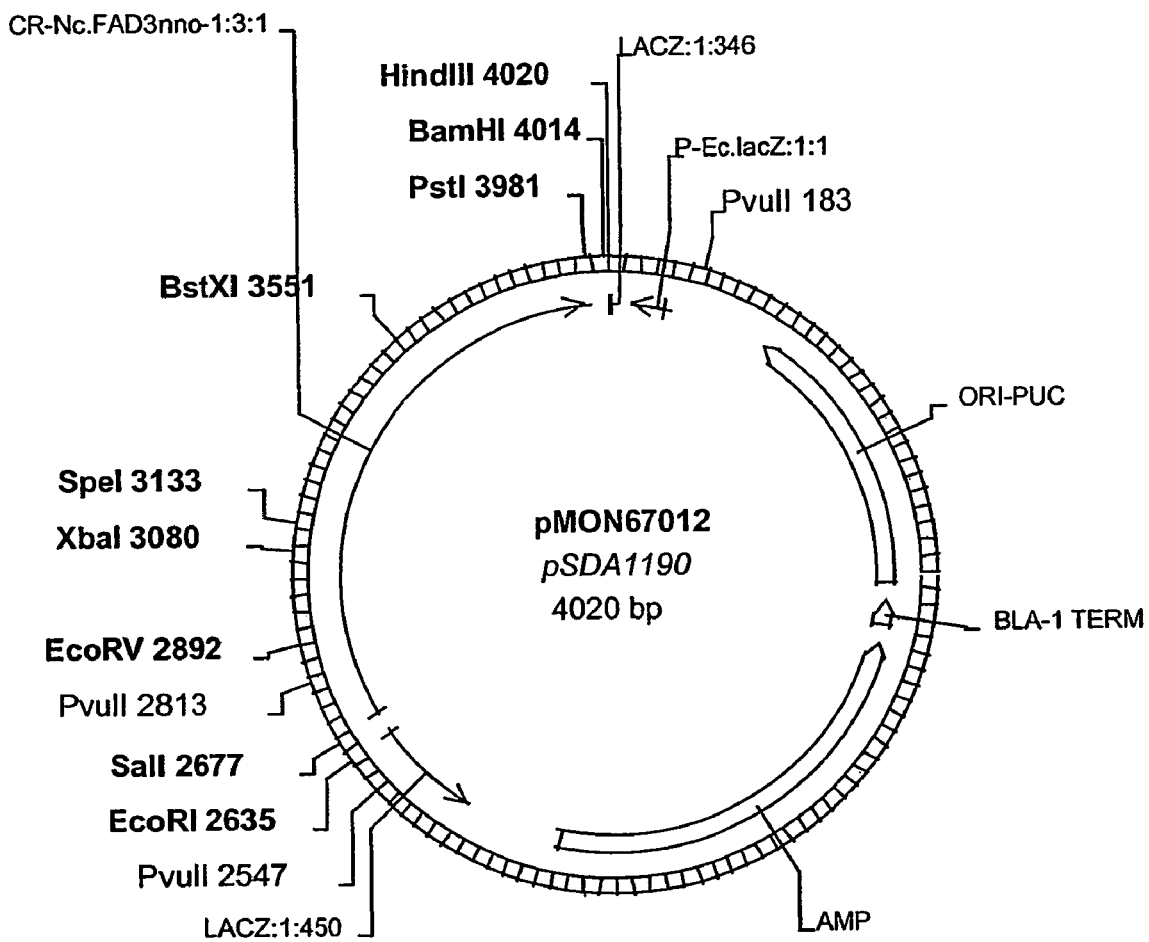

(SEQ ID NO:29)
BcD15F3: 5'-GTCGACACGATGACTCTCGATTACACAAGTCACC-3',
5' end contains SalI (SEQ ID NO:30)
BcD15R1: 5'-CTGCAGAATGCTTGAGCTATCAGCAGATCCCAA-3',
5' end contains PstI cDNA for *A. nidulans* and *B. cinerea* were prepared using the GeneRacer kit (Invitrogen). These primers were used with 3'-RACE ready cDNA to amplify putative desaturases using a GeneAmp PCR system 9700 (PE APPLIED BIOSYSTEMS) with the recommended cycle conditions. The PCR product encoding *A. nidulans* Δ15-desaturase was generated with oligonucleotides AnD15-F1 and AnD15-R1, was ligated into pYES2.1-TOPO (Invitrogen) and named pMON67010 (FIG. 7B). The cDNA was sequenced and three "His-boxes", a conserved feature among membrane-bound desaturases, were found to be present at amino acid positions 93-97, 129-133, and 327-331. The corresponding nucleotide and polypeptide sequences for the Δ15-desaturase (AnD15D) are given in SEQ ID NO:4 and SEQ ID NO:5, respectively.

Figure 7C:
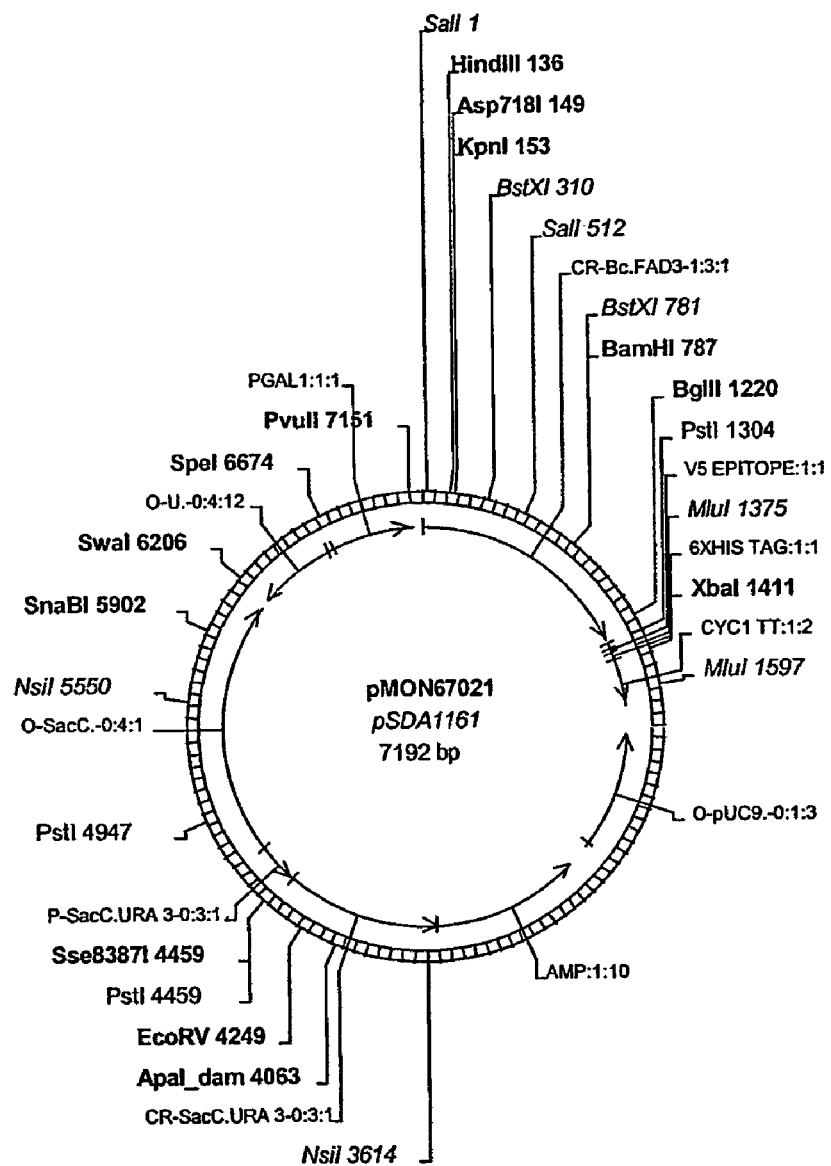
Figure 7D:
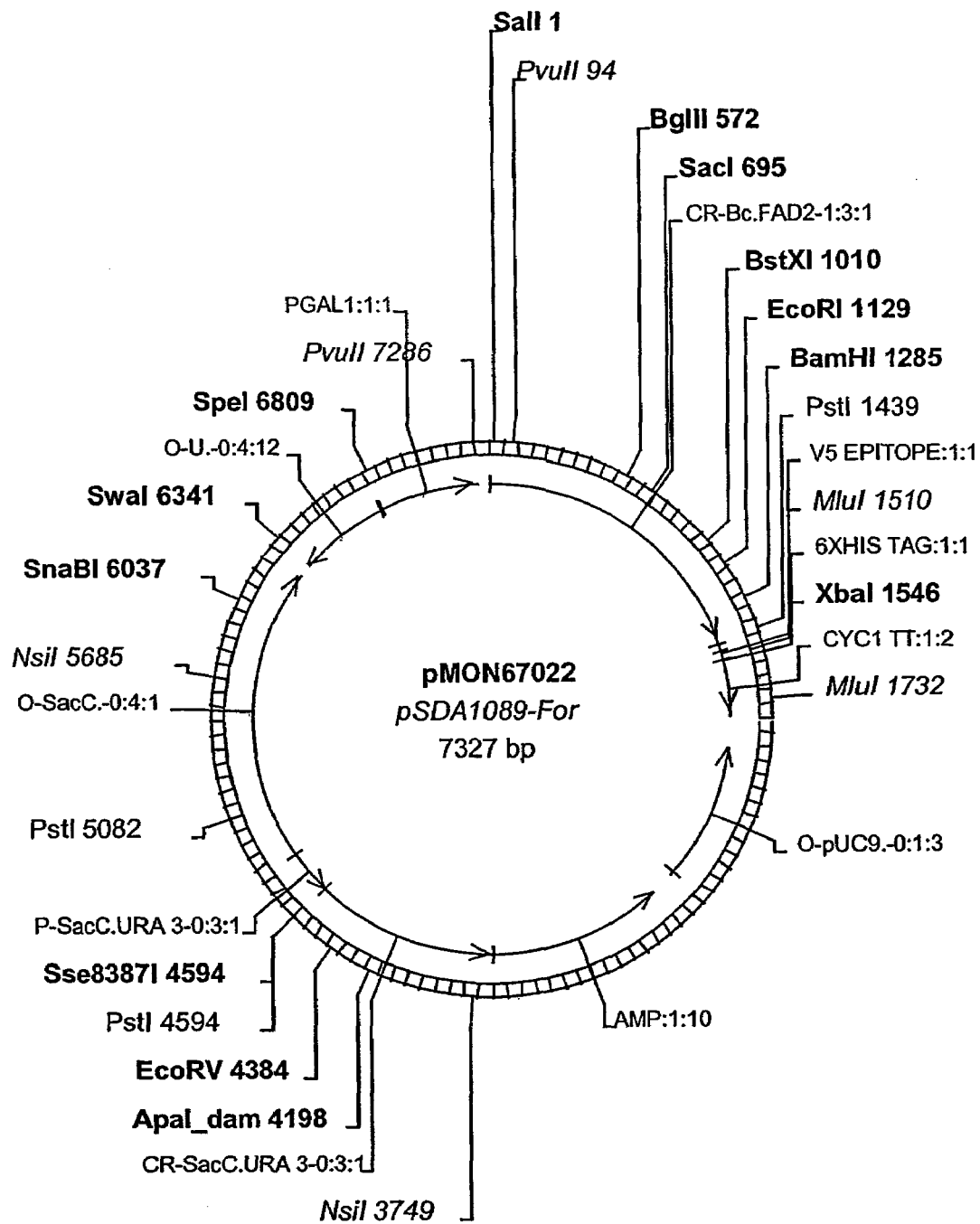

A *B. cinerea* Δ12-desaturase-encoding cDNA was amplified by PCR with oligonucleotides BcD12F1 and BcD12R1 and subsequently ligated directly into pYES2.1/V5-His-TOPO (Invitrogen) to generate pMON67022 (FIG. 7D). The cDNA was sequenced and three "His-boxes", a conserved feature among membrane-bound desaturases, were found to be present at amino acid positions 155-159, 191-195, and 390-394. The corresponding nucleotide and polypeptide sequences for the putative Δ12-desaturase (BcD12D) are given in SEQ ID NO:31 and SEQ ID NO:32, respectively.

To clone a Δ15-desaturase from *B. cinerea* a degenerate oligonucleotide was generated based on an amino acid sequence alignment of the *N. crassa*, and *Aspergillus* sp. Δ12 and Δ15-desaturases. A 5'-RACE reaction was performed using a GeneRacer Kit (Invitrogen, Carlsbad Calif.) following the conditions recommended by the manufacturer. Following cDNA synthesis, the 5' end of a putative Δ15-desaturase cDNA was amplified by PCR using the degenerate oligonucleotide D15D-R9 and ligated into pCR2.1-TOPO. The resulting 742 bp fragment was sequenced and determined by deduced amino acid alignment to be similar to the other fungal Δ15-desaturases. A 3'-RACE reaction was used to amplify 664 bp from the 3' end of the putative B. cinerea Δ15-desaturase using oligonucleotide BcD15-F1 and ligated into pCR2.1-TOPO. Oligonucleotides BcD15F3 and BcD15R1 were designed from the composite sequence of the 5'- and 3'-RACE products, and used to amplify a full length *B. cinerea* putative Δ15-desaturase cDNA by 3'-RACE reaction and ligated into pYES2.1-TOPO. The resulted plasmid was named pMON67021 (FIG. 7C). The corresponding nucleotide and polypeptide sequences for the putative Δ15-desaturase (BcD15D) are given in SEQ ID NO:33 and SEQ ID NO:34, respectively.

Figure 7E:
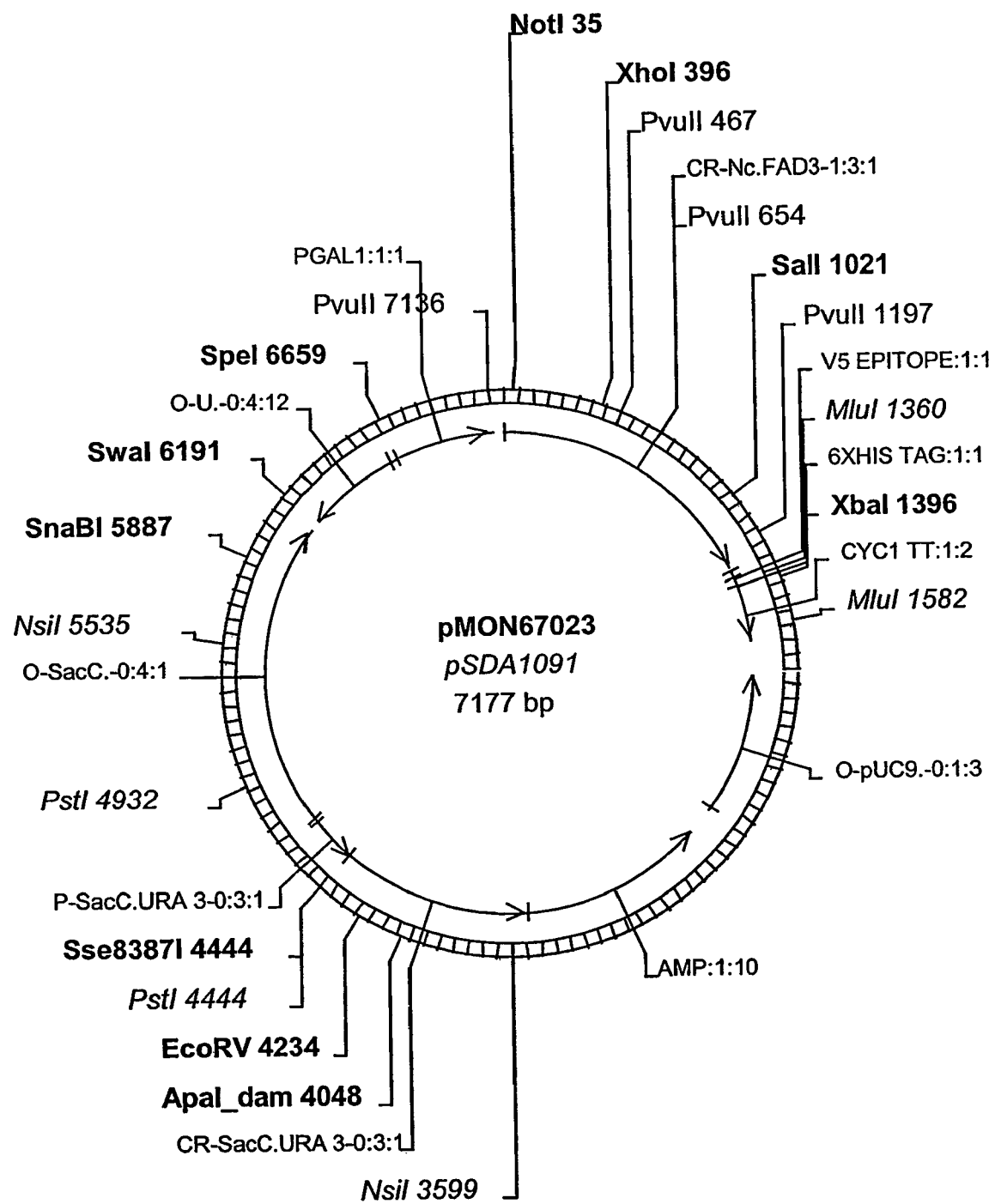

To assess Δ15-desaturase activity of the putative AnD15D in the yeast expression assay, yeast expressing the putative Δ15-desaturase were fed the substrate for this enzyme, i.e., LA, and the production of ALA quantified. These data, in which the production of ALA by the *N. crassa* Δ15-desaturase, pMON67023, was compared with that of the *A. nidulans* Δ15-desaturase, are shown in the Table 5. pMON67023 (FIG. 7E) was constructed as follows:

Primers Nc94F2 and Nc94R2 were used to amplify the coding region of NcD15D without a stop codon. The resulting fragment was ligated into pYES2.1-TOPO to generate an inframe fusion between the NcD15D coding region and the V5 epitope and 6-His region contained on the pYES2.1 expression vector.

TABLE 5

Production of ALA by *Neurospora crassa* Δ15-Desaturase and *Aspergillus nidulans* Δ15-desaturase

| Construct | Gene | Added Substrate | LA (added as substrate) | ALA |
|---|---|---|---|---|
| pMON67010 | AnD15D | LA | 28.43 | 20.32 |
| pMON67010 | AnD15D | LA | 24.66 | 19.65 |
| pMON67023 | NcD15D | LA | 47.98 | 10.94 |
| pMON67023 | NcD15D | LA | 47.52 | 9.24 |

These results indicate that in this expression system, the *A. nidulans* desaturase is approximately 2-fold more active than NcD15D.

TABLE 6

Analysis of AnD15D Substrate Utilization in Yeast

| Construct | Gene | Added Substrate | GLA | ALA | SDA |
|---|---|---|---|---|---|
| pMON67010 | AnD15D | — | 0 | 0.54 | 0 |
| pMON67010 | AnD15D | LA | 0 | 16.45 | 0 |
| pMON67010 | AnD15D | GLA | 9.19 | 0.27 | 8.82 |
| pMON67010 | AnD15D | LA + GLA | 9.46 | 5.99 | 5.35 |
| pMON67010 | AnD15D | — | 0 | 0.64 | 0 |
| pMON67010 | AnD15D | LA | 0 | 14.96 | 0 |
| pMON67010 | AnD15D | GLA | 8.36 | 0.27 | 8.63 |
| pMON67010 | AnD15D | LA + GLA | 8.1 | 6.31 | 5.48 |

These results indicate that in this expression system, the *A. nidulans* D15D is capable of desaturating both LA and GLA.

Example 9

Codon Optimization of the Δ15Desaturases From *A. nidulans* and *N. crassa* for Soybean A codon usage table was constructed from 8 highly expressed seed specific proteins from soybean (conglycinin, glycinin, globulin) and 17 highly expressed seed specific proteins from canola (cuciferin, napin, oleosin). The NcD15D and AnD15D nucleic acid sequences, along with the codon usage table described above, were sent to Blue Heron Biotechnology Inc., (Bothell, Wash.), who then utilized a proprietary algorithm to generate the final codon-optimized sequences with the lowest free energy-of-forming RNA secondary structures. The codon-optimized sequence of NcD15D was synthesized by Blue Heron Biotechnology Inc., (SEQ ID NO:35)
Nc94F2: 5'-AACATGACGGTCACCACCCGCAGCCACAAG-3'

(SEQ ID NO:36)
Nc94R2: 5'-CTGGGTGCTCTGAACGGTGTGCGCCCAAAT-3' and named NcD15Dnno (SEQ ID NO:37). The codon-optimized sequence of AnD15D was synthesized by Midland (Midland, Tex.), and named AnD15Dnno (SEQ ID NO:38).

Example 10

Activity of the Neurospora Δ15-desaturase in combination with the Δ6- and Δ12-desaturases from *Mortierella alpina*

Figure 7F:
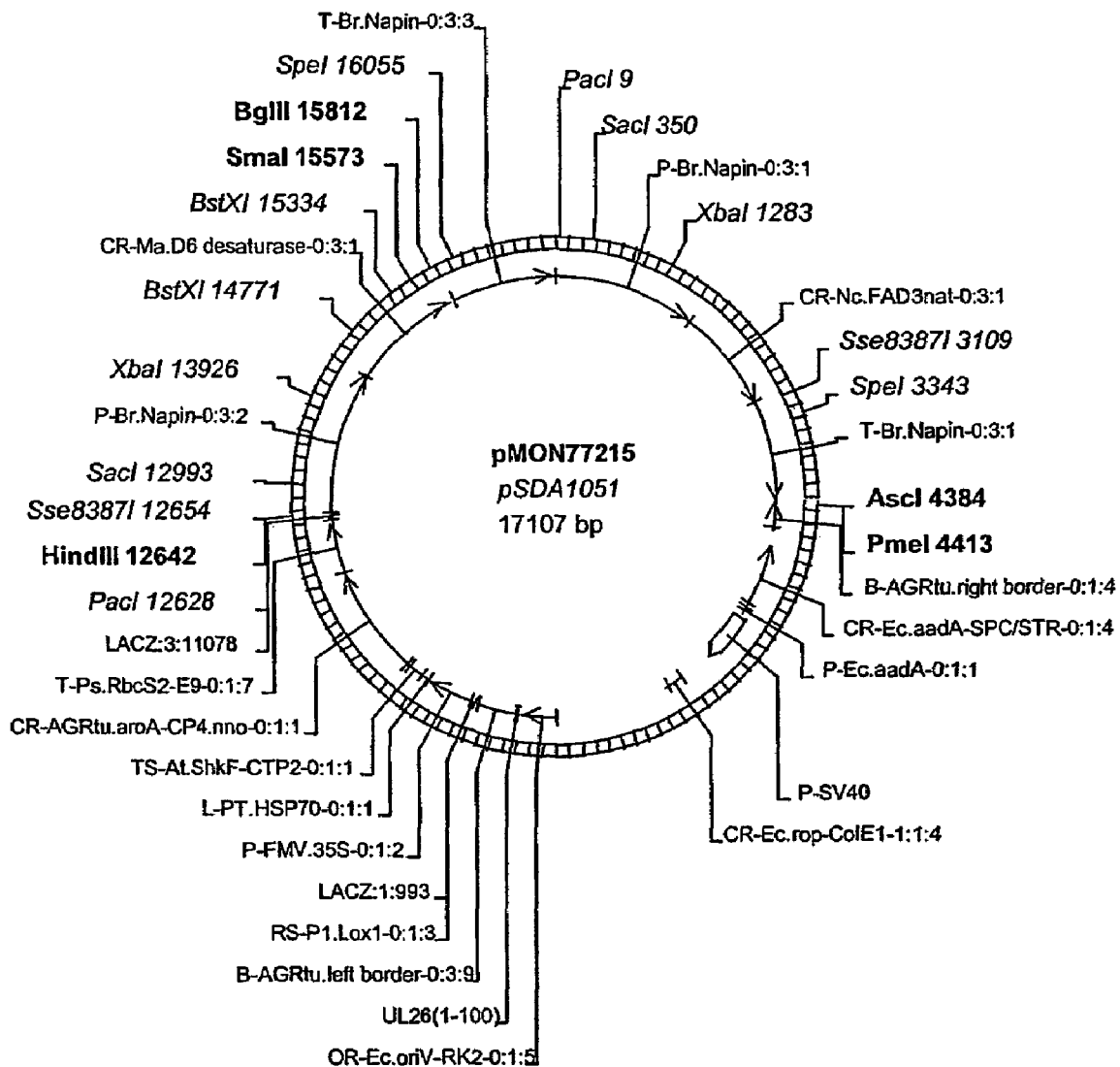
Figure 7G:
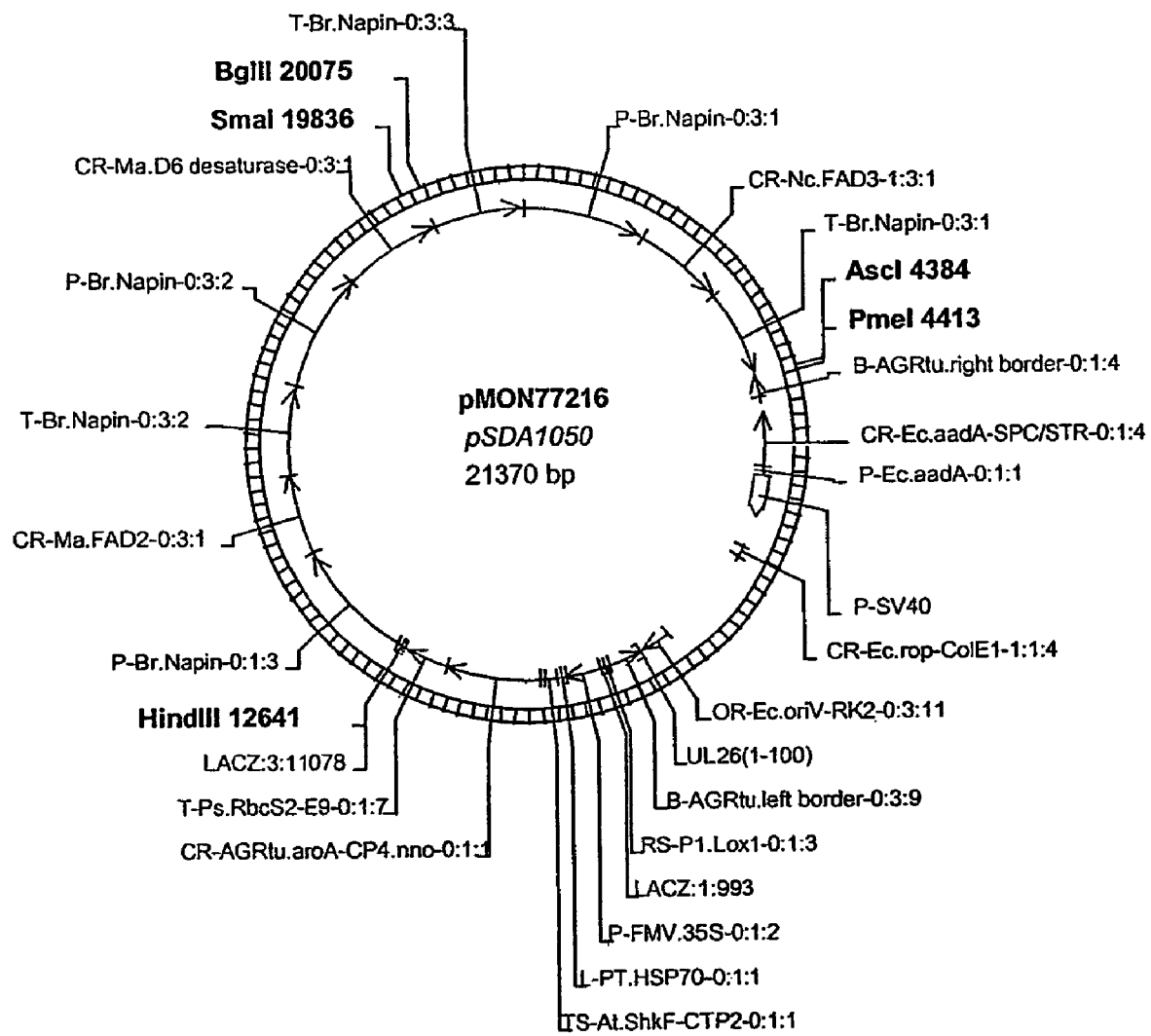

The activity of the *Neurospora* Δ15-desaturase in combination with the Δ6- and Δ12-desaturases from *Mortierella alpina* was evaluated by transforming canola with construct pMON77216 (FIG. 7G), which contains the three desaturases under the control of the Napin promoter. In a number of lines obtained, however, the Δ12-desaturase was found to have been partially deleted. Fatty acid content of 10-seed pools from individual R0 plants was determined. The levels of stearic acid (18:0) (SA), oleic acid (18:1)(OA), LA, ALA, SDA and GLA are shown in Table 6 below. The control line was Ebony. Pooled seed from a majority of the transgenic events produced contained measurable SDA and in 8 events SDA accumulated to greater than 10% of the fatty acids

TABLE 6

Relative Area Percent Results (Approx. wt percent) from pooled R1 seeds

| Event ID | Fatty Acid (wt percent) | | | | | |
|---|---|---|---|---|---|---|
| | SA | OA | LA | GLA | ALA | SDA |
| Control | 1.43 | 66.47 | 16.85 | 0 | 8.7 | 0 |
| Control | 1.43 | 60.27 | 19.65 | 0.52 | 11.94 | 0.07 |
| Control | 1.63 | 64.93 | 17.07 | 0.54 | 9.68 | 0.11 |
| BN_G1116 | 1.66 | 49.77 | 25.58 | 7.16 | 8.33 | 0.7 |
| BN_G1117 | 1.59 | 41.96 | 33.82 | 4.09 | 10.58 | 0.71 |
| BN_G1118 | 1.78 | 47.16 | 25.91 | 10.44 | 7.66 | 0.89 |
| BN_G1119 | 1.97 | 47.88 | 24.81 | 11.54 | 7.09 | 0.91 |
| BN_G1120 | 1.43 | 44.98 | 27.22 | 8.43 | 10.19 | 0.97 |
| BN_G1121 | 1.56 | 43.29 | 26.56 | 13.58 | 7.42 | 1.08 |
| BN_G1122 | 1.74 | 38.92 | 30.67 | 12.01 | 8.53 | 1.11 |
| BN_G1123 | 1.4 | 56.41 | 19.49 | 3.13 | 11.7 | 1.19 |
| BN_G1124 | 1.91 | 49.21 | 24.06 | 4.42 | 11.66 | 1.59 |
| BN_G1125 | 2.32 | 41.71 | 22.05 | 18.62 | 7.12 | 1.61 |
| BN_G1126 | 1.69 | 65.41 | 11.8 | 7.79 | 4.93 | 1.69 |
| BN_G1127 | 2.03 | 37.12 | 20.39 | 25.19 | 6.07 | 1.73 |
| BN_G1128 | 1.78 | 39.25 | 22.36 | 20.9 | 7.4 | 1.9 |
| BN_G1129 | 1.74 | 31.83 | 27.51 | 21.83 | 8.77 | 2.04 |
| BN_G1130 | 2.23 | 31.55 | 22.8 | 29.28 | 5.39 | 2.05 |
| BN_G1131 | 1.84 | 46.36 | 22.06 | 6.47 | 14.99 | 2.08 |
| BN_G1132 | 2.14 | 32.57 | 25.79 | 23.37 | 7.48 | 2.16 |
| BN_G1133 | 1.92 | 36.46 | 25.41 | 19.25 | 8.3 | 2.2 |
| BN_G1124 | 1.66 | 43.74 | 22.34 | 6.57 | 17.25 | 2.45 |
| BN_G1135 | 1.53 | 43.95 | 22.08 | 6.86 | 16.79 | 2.6 |
| BN_G1136 | 2.08 | 35.91 | 27.18 | 7.23 | 18.86 | 2.71 |
| BN_G1137 | 1.77 | 40.53 | 23.41 | 9.63 | 15.83 | 2.73 |
| BN_G1138 | 1.89 | 42.24 | 21.84 | 7 | 18.34 | 2.77 |
| BN_G1139 | 2.17 | 51.7 | 17.44 | 8.07 | 11.56 | 3.02 |
| BN_G1140 | 2.31 | 43.1 | 21.72 | 8.25 | 15.12 | 3.04 |
| BN_G1141 | 1.49 | 40.03 | 22.99 | 5.93 | 19.6 | 3.06 |
| BN_G1143 | 1.7 | 41.86 | 22.61 | 7.97 | 16.57 | 3.18 |
| BN_G1144 | 1.66 | 40.28 | 22.74 | 8.3 | 17.09 | 3.27 |
| BN_G1145 | 1.87 | 38.9 | 22.98 | 8.72 | 17.88 | 3.56 |
| BN_G1146 | 1.87 | 34.99 | 24.42 | 8.54 | 21 | 3.67 |
| BN_G1147 | 2.34 | 35.19 | 23.37 | 8.63 | 21.68 | 3.86 |
| BN_G1148 | 1.85 | 29.28 | 29.24 | 12.95 | 16.18 | 3.95 |
| BN_G1149 | 1.63 | 37.03 | 22.9 | 9.66 | 20.16 | 4.29 |
| BN_G1150 | 2.72 | 35.99 | 20.19 | 10.53 | 19.67 | 4.47 |
| BN_G1151 | 1.62 | 32.92 | 23.19 | 9.25 | 21.68 | 4.88 |
| BN_G1152 | 2.4 | 30.12 | 25.47 | 14.34 | 15.85 | 4.93 |
| BN_G1153 | 2.45 | 35.53 | 22.92 | 11.87 | 15.36 | 4.93 |
| BN_G1154 | 2.31 | 26.49 | 19.78 | 6.29 | 31.62 | 5.06 |
| BN_G1155 | 1.84 | 34.83 | 21.08 | 11.55 | 18.46 | 5.36 |
| BN_G1156 | 1.73 | 55.09 | 8.75 | 2.81 | 20.2 | 5.39 |

TABLE 6-continued

Relative Area Percent Results (Approx. wt percent) from pooled R1 seeds

| Event ID | Fatty Acid (wt percent) | | | | | |
|---|---|---|---|---|---|---|
| | SA | OA | LA | GLA | ALA | SDA |
| BN_G1157 | 1.87 | 34.84 | 21.19 | 10.88 | 19.14 | 5.41 |
| BN_G1158 | 2.98 | 29.18 | 22.71 | 17.48 | 14.23 | 5.9 |
| BN_G1159 | 2.17 | 36.41 | 18.63 | 10.27 | 20.3 | 5.98 |
| BN_G1160 | 1.85 | 40.01 | 17.37 | 13.86 | 13.79 | 6.11 |
| BN_G1161 | 1.94 | 29.5 | 25.74 | 9.15 | 20.3 | 6.12 |
| BN_G1162 | 1.74 | 33.78 | 20.98 | 12.79 | 16.98 | 6.24 |
| BN_G1163 | 1.84 | 34.83 | 21.13 | 10.28 | 18.76 | 6.27 |
| BN_G1164 | 1.96 | 37.43 | 17.03 | 5.79 | 24.34 | 6.45 |
| BN_G1165 | 1.86 | 36.5 | 18.9 | 11.28 | 18.7 | 6.68 |
| BN_G1166 | 1.95 | 29.59 | 24.52 | 13.72 | 18.95 | 6.69 |
| BN_G1167 | 2.62 | 25.92 | 22.63 | 15.39 | 19.76 | 6.69 |
| BN_G1168 | 2.78 | 48.4 | 12.78 | 6.28 | 17.57 | 6.71 |
| BN_G1169 | 2.92 | 37.66 | 17.21 | 13.51 | 14.14 | 7.22 |
| BN_G1170 | 2.57 | 26.3 | 22.62 | 11.07 | 22.43 | 7.25 |
| BN_G1171 | 2.24 | 24.1 | 20.08 | 28.31 | 10.8 | 7.53 |
| BN_G1172 | 2.79 | 26.16 | 20.37 | 13.4 | 21.15 | 7.8 |
| BN_G1173 | 1.88 | 28.4 | 20.84 | 21.11 | 13.55 | 7.93 |
| BN_G1174 | 2.36 | 24.04 | 17.6 | 28.46 | 10.82 | 8.13 |
| BN_G1175 | 3.43 | 24.83 | 20.39 | 21.68 | 15.5 | 8.23 |
| BN_G1176 | 2.06 | 30.09 | 18.23 | 13.06 | 20.9 | 8.23 |
| BN_G1177 | 1.74 | 64.72 | 7.85 | 2.46 | 8.1 | 8.29 |
| BN_G1178 | 1.62 | 25.75 | 19.49 | 9.12 | 27.3 | 8.6 |
| BN_G1179 | 1.72 | 30.98 | 19.19 | 11.78 | 20.65 | 8.95 |
| BN_G1180 | 2.55 | 21.39 | 19.93 | 26.55 | 12.19 | 9.07 |
| BN_G1181 | 2.53 | 21.81 | 21.21 | 15.3 | 22.58 | 9.16 |
| BN_G1182 | 1.75 | 24.68 | 20 | 14.66 | 22.4 | 9.36 |
| BN_G1183 | 2.42 | 31.08 | 16.43 | 15.08 | 17.5 | 9.48 |
| BN_G1184 | 2.2 | 26.92 | 17.92 | 17.43 | 18.69 | 10 |
| BN_G1185 | 2.58 | 63.63 | 4.49 | 5.11 | 6.18 | 10.29 |
| BN_G1186 | 1.13 | 55.27 | 9.21 | 4.08 | 12.73 | 10.29 |
| BN_G1187 | 2.22 | 37.22 | 14.97 | 13.19 | 16.2 | 10.46 |
| BN_G1188 | 2.5 | 26.64 | 18.05 | 19.8 | 14.58 | 10.83 |
| BN_G1189 | 2.41 | 26.12 | 18.44 | 16.81 | 19.27 | 11.01 |
| BN_G1190 | 2.29 | 36.61 | 12.21 | 14.29 | 14.68 | 13.31 |
| BN_G1191 | 2.31 | 18.94 | 12.95 | 18.11 | 22.1 | 17.95 |

Fatty acid data from single seeds of event BN_G1824, including both homozygotes and heterozygotes, is shown below in Table 7. In one case, 18.6.% SDA, 17.8% ALA, 11.2% LA, 24% oleic acid and 18.8% GLA were observed. This event is referred to as a high SDA/high GLA event. In another seed from this event, 16.8% SDA, 7% ALA, 2% LA, 62.1% oleic acid and 3.1% GLA were observed. This event is referred to as a high SDA/low GLA line. Molecular data indicated that, in the high SDA/low GLA lines, the Δ12 coding sequence was not functional. In particular, it was indicated that the high SDA/low GLA lines were comprised of a single copy of a single partial T-DNA insert that has lost all insert DNA between the left border and the terminal 51 base pairs of the coding region of the *Mortierella alpina* Δ12-desaturase (e.g., last 51 bp of SEQ ID NO:41). Notable in the high SDA/low GLA line is that oleic acid is nearly at wild type levels whereas in the high SDA/high GLA lines, oleic acid is reduced approximately 2.5 fold with respect to wild-type. The lines that display the high SDA/high oleic phenotype are highlighted with grey.

TABLE 7

Relative Area Percent Results (Approx. wt percent) R1 Single Seed of BN_G1190

| Line No. | SA | OA | LA | GLA | ALA | SDA |
|---|---|---|---|---|---|---|
| 1 | 1.29 | 64.94 | 19.96 | 0 | 9.07 | 0 |
| 2 | 1.53 | 65.62 | 16.5 | 0 | 10.01 | 0 |
| 3 | 1.4 | 61.38 | 20.02 | 0 | 11.78 | 0.02 |
| 4 | 1.78 | 65.09 | 17.67 | 0.02 | 9.22 | 0.15 |
| 5 | 1.53 | 60.94 | 7.8 | 3.55 | 14.13 | 5.23 |
| 6 | 2.01 | 61.95 | 7.1 | 4.2 | 12.34 | 5.79 |
| 7 | 1.8 | 59.54 | 5.5 | 4.47 | 12.81 | 9.2 |
| 8 | 2.16 | 25.6 | 17.86 | 19.69 | 18.91 | 9.28 |
| 9 | 1.9 | 61.92 | 4.71 | 3.25 | 12.71 | 9.34 |
| 10 | 4.79 | 22.52 | 14.36 | 29.86 | 9.84 | 10.29 |
| 11 | 2.81 | 61.55 | 3.92 | 2.79 | 11.89 | 10.46 |
| 12 | 2.07 | 61.13 | 4.36 | 4.37 | 10.9 | 10.47 |
| 13 | 1.57 | 59.75 | 4.27 | 3.3 | 13.01 | 11 |
| 14 | 1.89 | 63.95 | 3.54 | 2.88 | 10.29 | 11.09 |
| 15 | 1.95 | 62.9 | 4 | 3.53 | 10.35 | 11.29 |
| 16 | 2.04 | 60.91 | 4.2 | 3.2 | 12.16 | 11.37 |
| 17 | 2.37 | 49.02 | 7.68 | 12.6 | 9.45 | 11.48 |
| 18 | 1.88 | 62.52 | 3.41 | 4.25 | 9.09 | 11.79 |
| 19 | 2.4 | 25.65 | 16.6 | 17.6 | 18.36 | 12.03 |
| 20 | 3.31 | 25.5 | 16.45 | 16.69 | 18.76 | 12.12 |
| 21 | 5.64 | 20.98 | 12.57 | 29.74 | 10.03 | 12.17 |
| 22 | 2.51 | 24.55 | 15.7 | 17.28 | 19.83 | 12.23 |
| 23 | 2.62 | 25.54 | 15.55 | 18.14 | 18.87 | 12.45 |
| 24 | 3.35 | 22.96 | 14.87 | 23.38 | 14.62 | 12.98 |
| 25 | 2.2 | 24.61 | 15.99 | 17.98 | 18.5 | 13.61 |
| 26 | 1.62 | 58.5 | 3.48 | 3.09 | 12.36 | 13.66 |
| 27 | 3.77 | 24.48 | 14.69 | 18.4 | 16.75 | 13.85 |
| 28 | 2.51 | 23.72 | 15.35 | 16.53 | 19.8 | 14.24 |
| 29 | 2.46 | 24.04 | 13.81 | 18.61 | 19.94 | 14.31 |
| 30 | 2.44 | 23.63 | 14.82 | 20.44 | 16.85 | 14.35 |
| 31 | 1.85 | 64.75 | 1.94 | 2.85 | 7.01 | 14.55 |
| 32 | 2.04 | 19.45 | 14.32 | 15.63 | 25.95 | 14.73 |
| 33 | 2.24 | 23.34 | 14.79 | 18.9 | 18.22 | 14.84 |
| 34 | 3.55 | 23.16 | 12.92 | 21.86 | 15.59 | 15.12 |
| 35 | 3.17 | 24.94 | 12.74 | 18.41 | 16.98 | 15.26 |
| 36 | 2.36 | 21.79 | 14.57 | 23.35 | 13.99 | 15.38 |
| 37 | 2.55 | 23.14 | 14.94 | 19.56 | 17.3 | 15.39 |
| 38 | 2.53 | 23.44 | 14.99 | 16.32 | 19.84 | 15.46 |
| 39 | 2.09 | 58.1 | 2.87 | 3.21 | 11.23 | 15.52 |
| 40 | 2.22 | 61.6 | 2.44 | 3.32 | 8.34 | 15.58 |
| 41 | 4.1 | 23.71 | 13.78 | 17.72 | 18.09 | 15.63 |
| 42 | 2.34 | 22.81 | 13.35 | 19.72 | 19.09 | 15.67 |
| 43 | 3.71 | 21.49 | 13.43 | 22.95 | 14.94 | 15.98 |
| 44 | 4.05 | 23.04 | 13.77 | 20.1 | 15.43 | 16.18 |
| 45 | 2.57 | 24.02 | 12.05 | 19.87 | 17.05 | 16.46 |
| 46 | 2.09 | 62.09 | 1.98 | 3.08 | 7.06 | 16.75 |
| 47 | 3.17 | 21.82 | 13.7 | 16.23 | 21.06 | 16.82 |
| 48 | 4.07 | 22.52 | 12.25 | 19.85 | 16.27 | 16.86 |
| 49 | 2.46 | 22.48 | 12.5 | 20.28 | 17.02 | 17.66 |
| 50 | 2.78 | 24.11 | 11.17 | 18.82 | 17.75 | 18.59 |

In order to further assess the activity of the *Neurospora crassa* Δ15-desaturase in combination with the *M alpina* Δ6- and Δ12-desaturases, lines homozygous for construct pCGN5544 (containing *M. alpina* Δ6- and Δ12-desaturases), which contained up to 35% GLA in seed oils, were re-transformed with construct pMON77214 containing NcD15D. Twenty-seed pools from 11 R₀ plants were analyzed. The LA, ALA, SDA and GLA in these lines are shown in Table 8.

TABLE 8

Relative Area Percent Results (Approx. wt percent) Analysis of R1 Pool seed

| Line | LA | ALA | SDA | GLA |
|---|---|---|---|---|
| Ebony control | 16.05 | 8.7 | 0 | 0 |
| Ebony control | 17.46 | 9.05 | 0 | 0 |
| BN_1569 | 21.19 | 11 | 0.11 | 30.1 |
| BN_1561 | 25.35 | 14.7 | 1.57 | 6.03 |
| BN_1566 | 29.26 | 14.03 | 1.75 | 9.04 |
| BN_1564 | 17.92 | 26.51 | 2.33 | 4.5 |
| BN_1644 | 24.25 | 16.1 | 4.05 | 16.64 |
| BN_1527 | 22 | 15.97 | 4.17 | 10.44 |

TABLE 8-continued

Relative Area Percent Results (Approx. wt percent) Analysis of R1 Pool seed

| Line | LA | ALA | SDA | GLA |
|---|---|---|---|---|
| BN_1563 | 20.13 | 17.26 | 4.52 | 12.11 |
| BN_1609 | 22.46 | 23.76 | 5.22 | 11.39 |
| BN_1622 | 9.1 | 15.77 | 6.33 | 5.23 |
| BN_1680 | 21.47 | 19.19 | 11.19 | 19.07 |
| BN_1624 | 12.95 | 22.1 | 17.95 | 18.11 |

Example 11

Activity of the *Neurospora crassa* Δ15-Desaturase in Combination With the Δ6Desaturase From *Mortierella alpina*

The activity of the *Neurospora crassa* Δ15-desaturase in combination with the Δ6-desaturase from *Mortierella alpina* was evaluated by transforming canola with the construct pMON77215 (FIG. 7F), which contains the two desaturases under the control of the Napin promoter. This vector was constructed by digesting pCGN5536 (U.S. Pat. No. 6,459,018 B1), which contains the Napin promoter driving expression of the *M. alpina* Δ6-desaturase (MaD6D), with NotI and then by ligating the expression cassette fragment into the Not I site of the binary vector, pMON70660, to form pMON77212. The pMON77215 plasmid was constructed by digesting pMON77214 with PmeI and AscI and then by ligating the resulting Napin-NcD15D expression cassette fragment into the SwaI and AscI sites of pMON77212, to give a construct containing both MaD6D and NcD15D.

Fatty acid content of 10-seed pools from individual R0 canola transformants was determined. The levels of SA, OA, LA, ALA, SDA and GLA are shown in Table 9 below. The control line was Ebony (SP30052). Pooled seed from a majority of the transgenic events produced contained measurable SDA and in 25% of the events (10 out of 40) SDA accumulated to greater than 10% of the fatty acids.

TABLE 9

Relative Area Percent Results (Approx. wt percent) for pMON77215 Pooled R1 Seed

| Event ID | SA | OA | LA | GLA | ALA | SDA |
|---|---|---|---|---|---|---|
| Ebony COntrol | 1.43 | 66.47 | 16.85 | 0 | 8.7 | 0 |
| BN_G2463 | 1.98 | 63.51 | 17.96 | 0.13 | 9.9 | 0.1 |
| BN_G2444 | 1.62 | 60.61 | 19.58 | 0.13 | 11.38 | 0.36 |
| BN_G2443 | 1.47 | 59.39 | 17.8 | 3.42 | 10.2 | 1.1 |
| BN_G1700 | 1.69 | 65.41 | 11.8 | 7.79 | 4.93 | 1.69 |
| BN_G2082 | 1.84 | 59.51 | 16.72 | 4.45 | 10.16 | 1.73 |
| BN_G2316 | 2.19 | 66.1 | 11.49 | 7.17 | 4.24 | 2.24 |
| BN_G2083 | 1.89 | 61.57 | 12.61 | 7.29 | 7.02 | 2.28 |
| BN_G2413 | 1.97 | 64.12 | 9.74 | 1.58 | 11.09 | 4.63 |
| BN_G2317 | 2.74 | 66.72 | 6.92 | 0.44 | 10.42 | 5.13 |
| BN_G2412 | 2.31 | 61.63 | 8.48 | 1.66 | 13.6 | 5.21 |
| BN_G2315 | 2.91 | 64.38 | 10.22 | 0.91 | 6.07 | 5.28 |
| BN_G2028 | 1.91 | 61.48 | 10.25 | 2.2 | 11.59 | 5.59 |
| BN_G2357 | 2.51 | 64.17 | 8.28 | 0.85 | 10.42 | 5.62 |
| BN_G2027 | 2.13 | 53.72 | 12.39 | 2.6 | 15.72 | 5.78 |
| BN_G2360 | 2.51 | 62.75 | 9.47 | 4.89 | 7.17 | 5.84 |
| BN_G2390 | 3.2 | 63.66 | 8.44 | 0.5 | 10.2 | 5.88 |
| BN_G2029 | 1.78 | 61.89 | 10.41 | 1.44 | 11.12 | 6.35 |
| BN_G2414 | 2.07 | 57.13 | 11 | 2.36 | 14.07 | 6.44 |

TABLE 9-continued

Relative Area Percent Results (Approx. wt percent) for pMON77215 Pooled R1 Seed

| Event ID | Fatty Acid (Wt percent) | | | | | |
|---|---|---|---|---|---|---|
| | SA | OA | LA | GLA | ALA | SDA |
| BN_G2416 | 2.26 | 65.01 | 7.17 | 0.83 | 11.86 | 6.45 |
| BN_G2250 | 2.19 | 61.99 | 8.8 | 1.93 | 9.72 | 6.6 |
| BN_G1698 | 1.82 | 68.26 | 6.4 | 3.76 | 6.55 | 6.65 |
| BN_G2356 | 2.82 | 62.46 | 11.52 | 1.75 | 6.99 | 6.84 |
| BN_G1937 | 2 | 56.02 | 10.92 | 2.24 | 12.6 | 7.81 |
| BN_G2319 | 1.99 | 58.47 | 9.63 | 5.86 | 9.05 | 7.91 |
| BN_G1699 | 1.74 | 64.72 | 7.85 | 2.46 | 8.1 | 8.29 |
| BN_G2359 | 2.96 | 64.17 | 7.09 | 2.05 | 7.67 | 8.88 |
| BN_G2460 | 2.54 | 62.4 | 5.33 | 1.43 | 11.43 | 9.63 |
| BN_G2409 | 3.27 | 57.85 | 9.71 | 3.97 | 7.44 | 9.87 |
| BN_G2318 | 2.54 | 61.04 | 7.6 | 2.37 | 8.43 | 9.99 |
| BN_G2358 | 2.76 | 62.33 | 5.88 | 2.06 | 8.72 | 10.08 |
| BN_G1697 | 2.58 | 63.63 | 4.49 | 5.11 | 6.18 | 10.29 |
| BN_G1803 | 1.13 | 55.27 | 9.21 | 4.08 | 12.73 | 10.29 |
| BN_G2391 | 2.83 | 58.33 | 11.45 | 2.42 | 6.6 | 10.57 |
| BN_G1859 | 2.33 | 52.66 | 9.71 | 2.98 | 12.19 | 11.03 |
| BN_G2389 | 2.54 | 59.21 | 6.97 | 3.88 | 8.07 | 11.84 |
| BN_G1860 | 2.22 | 51.02 | 9.49 | 4.62 | 10.5 | 13.44 |
| BN_G2410 | 3.24 | 55.96 | 7.03 | 3.1 | 8.88 | 13.82 |
| BN_G2445 | 2.77 | 57.67 | 6.21 | 2.78 | 9.62 | 14.14 |
| BN_G2361 | 2.31 | 56.5 | 8.86 | 3.77 | 6.48 | 14.78 |

Fatty acid data from single seeds of from event BN_G 1860, including both homozygotes and heterozygotes, is shown below in Table 10. In one case, up to 19% SDA, 10% ALA, 7% LA, 48% Oleic acid and 5% GLA was observed.

TABLE 10

Relative Area Percent Results (Approx. wt percent) for pMON77215 Single R1 Seed of BN_G1860

| Event ID | Fatty Acid (Wt percent) | | | | | |
|---|---|---|---|---|---|---|
| | SA | OA | LA | GLA | ALA | SDA |
| BN_G1860-1 | 1.57 | 65.11 | 16.5 | 0 | 10.47 | 0.01 |
| BN_G1860-2 | 1.4 | 57.32 | 19.05 | 0 | 15.3 | 0.02 |
| BN_G1860-3 | 1.74 | 60.16 | 19.44 | 0 | 11.95 | 0.03 |
| BN_G1860-4 | 1.77 | 56.85 | 8.11 | 6.79 | 9.11 | 9.96 |
| BN_G1860-5 | 2.37 | 57.88 | 5.26 | 2.94 | 12.72 | 11.48 |
| BN_G1860-6 | 1.72 | 60.18 | 5.03 | 2.87 | 11.42 | 11.71 |
| BN_G1860-7 | 2.53 | 55.86 | 9.31 | 6.08 | 5.96 | 12.23 |
| BN_G1860-8 | 2.21 | 56.83 | 7.48 | 5.93 | 8.52 | 12.38 |
| BN_G1860-9 | 2.12 | 60.21 | 4.83 | 2.8 | 10.13 | 12.43 |
| BN_G1860-10 | 3.12 | 56.6 | 10.33 | 4.54 | 4.5 | 12.48 |
| BN_G1860-11 | 2.2 | 53.64 | 12.32 | 5.54 | 4.73 | 12.88 |
| BN_G1860-12 | 2.25 | 55.58 | 10.53 | 5.07 | 5.42 | 13.53 |
| BN_G1860-13 | 2.03 | 57.57 | 7.08 | 4.19 | 8.15 | 13.69 |
| BN_G1860-14 | 1.76 | 54.42 | 7.16 | 6.43 | 8.99 | 13.77 |
| BN_G1860-15 | 2.77 | 57.4 | 8.5 | 4.17 | 5.73 | 13.78 |
| BN_G1860-16 | 1.43 | 55.39 | 9.93 | 5.62 | 6.38 | 13.82 |
| BN_G1860-17 | 2.91 | 53.02 | 10.79 | 4.34 | 5.89 | 13.92 |
| BN_G1860-18 | 1.92 | 60.27 | 3.72 | 1.96 | 10.7 | 13.92 |
| BN_G1860-19 | 1.85 | 59.6 | 4.72 | 2.56 | 9.85 | 14.16 |
| BN_G1860-20 | 2.45 | 58.84 | 6.51 | 3.66 | 6.88 | 14.22 |
| BN_G1860-21 | 1.88 | 57.95 | 5 | 2.85 | 10.56 | 14.42 |
| BN_G1860-22 | 1.91 | 55.15 | 6.02 | 5.3 | 9.2 | 14.75 |
| BN_G1860-23 | 3.01 | 59.08 | 5.36 | 2.88 | 7.33 | 14.85 |
| BN_G1860-24 | 2.94 | 56.48 | 6.78 | 3.95 | 7.83 | 14.86 |
| BN_G1860-25 | 2.34 | 53.88 | 8.64 | 4.49 | 6.42 | 14.94 |
| BN_G1860-26 | 2.75 | 52.92 | 7.04 | 4.38 | 9.4 | 14.96 |
| BN_G1860-27 | 1.7 | 57.28 | 4.41 | 2.99 | 10.74 | 15.05 |
| BN_G1860-28 | 2.3 | 53.15 | 9.42 | 5.79 | 6.53 | 15.29 |
| BN_G1860-29 | 2.9 | 54.49 | 6.2 | 3.73 | 7.92 | 15.38 |
| BN_G1860-30 | 1.8 | 58.02 | 4 | 2.41 | 10.67 | 15.42 |
| BN_G1860-31 | 2.67 | 54.97 | 7.32 | 4.68 | 7.92 | 15.44 |
| BN_G1860-32 | 2.31 | 56.01 | 5.09 | 4.34 | 9.93 | 15.47 |
| BN_G1860-33 | 2.18 | 55.92 | 8.83 | 4.06 | 5.46 | 15.54 |

TABLE 10-continued

Relative Area Percent Results (Approx. wt percent) for pMON77215 Single R1 Seed of BN_G1860

| Event ID | Fatty Acid (Wt percent) | | | | | |
|---|---|---|---|---|---|---|
| | SA | OA | LA | GLA | ALA | SDA |
| BN_G1860-34 | 2.38 | 54.85 | 8.52 | 4.01 | 5.76 | 15.56 |
| BN_G1860-35 | 1.99 | 58.89 | 4.14 | 2.09 | 9.74 | 15.58 |
| BN_G1860-36 | 2.87 | 55.91 | 6.55 | 2.8 | 7.37 | 15.66 |
| BN_G1860-37 | 2.35 | 53.18 | 8.89 | 4.73 | 6.45 | 15.71 |
| BN_G1860-38 | 3.15 | 51.6 | 10.29 | 4.85 | 5.68 | 15.78 |
| BN_G1860-39 | 2.31 | 55.68 | 6.08 | 4.52 | 7.81 | 15.92 |
| BN_G1860-40 | 3.26 | 54.62 | 6.54 | 3.55 | 7.53 | 16.19 |
| BN_G1860-41 | 2.09 | 56.03 | 6.27 | 4.04 | 7.56 | 16.35 |
| BN_G1860-42 | 2.33 | 53.62 | 6.48 | 5.35 | 7.97 | 16.62 |
| BN_G1860-43 | 2.37 | 57.86 | 5.24 | 2.81 | 7.32 | 16.77 |
| BN_G1860-44 | 2.04 | 51.3 | 11.41 | 5.03 | 5.09 | 16.94 |
| BN_G1860-45 | 2.1 | 53.32 | 8.75 | 4.04 | 6.44 | 17.12 |
| BN_G1860-46 | 2.14 | 53.01 | 6.85 | 4.3 | 7.82 | 17.16 |
| BN_G1860-47 | 2.42 | 50.96 | 7.83 | 4.13 | 7.91 | 17.44 |
| BN_G1860-48 | 1.94 | 49.97 | 10.64 | 4.78 | 5.74 | 17.84 |
| BN_G1860-49 | 1.46 | 55.32 | 4.57 | 2.67 | 9.98 | 18 |
| BN_G1860-50 | 2.41 | 47.66 | 6.83 | 5.46 | 9.91 | 19.23 |

Example 12

Codon Optimization of the Δ15Desaturase Sequence from *N. crassa* for Maize

A codon usage table was constructed from 9 highly expressed seed-specific genes from maize (six zeins and three oleosins). Using this table, two codons of NcD15D were mutated using the QuikChange Site-Directed Mutagenesis Kit (Stratagene, La Jolla, Calif.) and the resulting sequence was named NcFAD3m (SEQ ID NO:42). The codons changed were as follows: 1) to make a more preferred translational start site, an alanine in SEQ ID NO:2 is substituted with a threonine by changing the first base of the second codon (position 4 in SEQ ID NO: 42) from an ACG to GCG; and 2) to remove a rare codon, a valine codon was changed from GTA to GTG at position 882 (SEQ ID NO: 42).

Example 13

EPA Equivalence

One measure of seed oil quality for health value is EPA equivalence. The value reflects the metabolic conversion rate to EPA. This is calculated by adding the % ALA divided by 14 and the % SDA divided by 4. The canola oil compositions obtained by the inventors had a high EPA equivalence, indicating excellent characteristics for achieving the health benefits associated increased EPA levels in humans and animals. An example of the analysis is given below by comparison of conventional canola oil relative to an example of a typical high SDA oil composition of 10% ALA and 15% SDA. Canola oil from conventional varieties has approximately 12% ALA and 0% SDA and thus has an EPA equivalence of 12/14+0/4=0.8. In contrast, the high SDA oil composition example has an EPA equivalence of 10/14+15/4=4.4. The relative values are shown below. Values are by wt %, not on a serving basis. The vast difference shows the importance of producing SDA in canola oil.

TABLE 11

EPA Equivalence Comparison

| Vegetable Oil | Total omega-3 (% fatty acids) | n-6:n-3 ratio (% fatty acids) | Relative EPA equivalence (wt % ALA + SDA) |
|---|---|---|---|
| Canola | 12 | 2.6:1 | 0.8 |
| SDA Canola | 50 | 1:5 | 4.4 |

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 4,666,701
U.S. Pat. No. 4,758,592
U.S. Pat. No. 4,826,877
U.S. Pat. No. 4,910,141
U.S. Pat. No. 5,011,770
U.S. Pat. No. 5,116,871
U.S. Pat. No. 5,302,523
U.S. Pat. No. 5,322,783
U.S. Pat. No. 5,378,619
U.S. Pat. No. 5,384,253
U.S. Pat. No. 5,464,765
U.S. Pat. No. 5,508,184
U.S. Pat. No. 5,508,468
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
U.S. Pat. No.5,952,544
Abdullah et al., *Biotechnology*, 4:1087, 1986.
Arondel, *Science*, 258(5086):1353-1355, 1992.
Ausubel et al., In: Current Protocols in Molecular Biology, Green Publishing Assoc., NY, 1987.
Barton et al., *Cell*, 32:1033, 1983.
Bates, *Mol. Biotechnol*, 2(2):135-45, 1994.
Battraw and Hall, *Theor. App. Genet.*, 82(2):161-168, 1991.
Bechtold et al., *CR. Acad. Sci. Life Sci.*, 316:1194-1199, 1993.
Becker and Guarente, *Methods Enzymol.*, 194:182-187, 1991.
Bent et al., *Science*, 265:1856-1860, 1994.
Bent et al. (1994), Science 265:1856-1860
Bevan et al., *Nucleic Acids Res.*, 11(2):369-385, 1983.
Bevan, *Nucleic Acids Res.*, 12:8111, 1984.
Bhattacharjee, An, Gupta, *J. Plant Bioch. Biotech.*, 6(2):69-73, 1997.
Bouchez et al., *EMBO Journal*, 8(13):4197-4204, 1989.
Bower et al., *J. Plant*, 2:409-416, 1992.
Bray, 1987
Brenner et al., *Adv. Exp. Med. Biol.*, 83:85-101, 1976.
Buchanan-Wollaston et al., *Plant Cell Reports*, 11:627-631, 1992
Buising and Benbow, *Mol. Gen. Genet.*, 243(1):71-81, 1994.
Bustos et al., *J. Bacteriol.*, 174:7525-7533, 1991.
Callis et al., *Genes Dev.*, 1:1183-1200, 1987.
Casa et al., *Proc. Natl. Acad. Sci. USA*, 90(23):11212-11216, 1993.
Case et al., *Neurospora Newsletter*, 8:25-26, 1965.
Chandler et al., *The Plant Cell*, 1:1175-1183, 1989.
Chomczynski and Sacchi, *Anal. Biochem.*, 162(1):156-159, 1987.
Chou and Fasman, *Adv. Enzymol*, 47:45-148, 1978.
Christou et al., *Proc. Natl. Acad. Sci. USA*, 84(12):3962-3966, 1987.
Conkling et al., *Plant Physiol.*, 93:1203-1211, 1990.
Crozier, *Lipids*, 24:460, 1989.
De Block et al., *Plant Physiol.*, 91:694-701, 1989.
De Block et al., *The EMBO Journal*, 6(9):2513-2518, 1987.
De Deckerer, *Eur. J. Clin. Nutr.*, 52:749, 1998.
DeBlock et al., *J. EMBO*, 2:2143, 1984.
Dellaporta et al., In: Chromosome Structure and Function: Impact of New Concepts, 18th Stadler Genetics Symposium, 11:263-282, 1988.
Denmark Appl. DE 3642 829
D'Halluin et al., *Plant Cell*, 4(12):1495-1505, 1992.
Ebert et al., *Proc. Natl. Acad. Sci. USA*, 84:5745-5749, 1987
Ellis et al., *EMBO Journal*, 6(11):3203-3208, 1987.
Europ. Appl. 154,204
Fraley et al., *Bio/Technology*, 3:629-635, 1985.
Fromm et al., *Nature* 319:791-793, 1986
Fromm et al., *Nature*, 319:791-793, 1986.
Gallie et al., *The Plant Cell*, 1:301-311,1989.
Gelvin et al., In: Plant Molecular Biology Manual, 1990.
Ghosh-Biswas et al., *J. Biotechnol.*, 32(1):1-10, 1994.
Goeddel, In: Methods in Enzymology, Perbal (Ed.), Academic Press, John Wiley and Sones, 185, 1988.
Hagio, Blowers, Earle, *Plant Cell Rep.*, 10(5):260-264, 1991.
Hamilton et al., *Proc. Natl. Acad. Sci. USA*, 93(18):9975-9979, 1996.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218,1997.
Hinchee et al., *Bio/technol.*, 6:915-922, 1988.
Horrobin et al., *Am. J. Clin. Nutr.*, 57(Suppl):732S-737S, 1993.
Horsch et al., *Science*, 223:496, 1984.
Horsch et al., *Science*, 227:1229, 1985.
Hou and Lin, *Plant Physiology*, 111:166, 1996.
Huang, *Biochem. Biophys. Acta*, 1082:319, 1991.
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
IUPAC-IUB, *Nucl. Acid Res.*, 13:3021-3030,1985.
James et al., *Can. J. Physiol. Pharmacol.*, 75:234, 1997.
James et al., *Semin. Arthritis Rheum.*, 28:85, 2000.
Kaeppler et al., *Plant Cell Reports*, 9:415-418, 1990.
Kaeppler et al., *Theor. Appl. Genet.*, 84(5-6):560-566, 1992.
Katz et al., *J. Gen. Microbiol.*, 129:2703-2714, 1983.
Klee et al., *Bio-Technology*, 3(7):637-642, 1985.
Klein et al., *Nature*, 327:70,1987.
Knittel et al., *Plant Cell Reports*, 14(2-3):81-86, 1994.
Knutzon et al., *Proc. Natl. Acad. Sci. USA*, 89(7):2624-2628, 1992.
Kyte and Doolittle, *J. Mol. Biol.*, 157:105-132, 1982.
Lawton et al., *Plant Mol. Biol.* 9:315-324, 1987.
Lazzeri, *Methods Mol. Biol.*, 49:95-106, 1995.
Lee et al., *Environ. Mol. Mutagen.*, 13(1):54-59, 1989.
Lorz et al., *Mol Gen Genet*, 199:178-182, 1985.
Manzioris et al., *Am. J. Clin. Nutr.*, 59:1304, 1994.
Marcotte et al., *Nature*, 335:454, 1988.

McCabe, Martinell, *Bio-Technology,* 11 (5):596-598, 1993.
McCormac et al., *Euphytica,* 99(1):17-25, 1998.
Meesapyodsuk et al., *Biochemistry,* 39(39):11948-11954, 2000.
Michaelis et al., *Ann. Rev. Microbiol.,* 36:425, 1982.
Murakami et al., *Mol. Gen. Genet.,* 205:42-50, 1986.
Nagatani et al., *Biotech. Tech.,* 11(7):471-473, 1997.
Naylor et al., *Nature,* 405:1017, 2000.
Odell et al., *Nature,* 313:810-812, 1985.
Ogawa et al., *Sci. Rep.,* 13:42-48, 1973.
Omirulleh et al., *Plant Mol. Biol.,* 21(3):415-28, 1993.
Ow et al., *Science,* 234:856-859, 1986.
PCT Appl. WO 9217598
PCT Appl. WO 94/09699
PCT Appl. WO 95/06128
PCT Appl. WO 96/33155
PCT Appl. WO 97/4103
PCT Appl. WO 97/41228
Potrykus et al., *Mol. Gen. Genet.,* 199(2):169-77, 1985.
Potrykus et al., *Mol. Gen. Genet.,* 199:183-188,1985.
Prasher et al., *Biochem. Biophys. Res. Commun.,* 126(3): 1259-1268, 1985.
Reed et al., *Plant Physiol.,* 122:715-720, 2000.
Reichel et al., *Proc. Natl. Acad. Sci. USA,* 93 (12) p. 5888-5893. 1996
Restrepo et al, *Plant Cell,* 2:987, 1990.
Rhodes et al., *Methods Mol. Biol.,* 55:121-131, 1995.
Ritala et al., *Plant Mol. Biol.,* 24(2):317-325, 1994.
Rogers et al., *Methods Enzymol.,* 153:253-277, 1987.
Sambrook et al., *In: Molecular cloning,* Cold Spring Harbor Laboratory Press, Cold Spring Harbor, N.Y., 1989.
Sheen et al., *Plant Journal,* 8(5):777-784, 1995.
Simopoulos et al., *Am. Coll. Nutr.,* 18:487, 1999.
Singsit et al., *Transgenic Res.,* 6(2):169-176, 1997.
Spencer et al., *Plant Molecular Biology,* 18:201-210, 1992.
Stalker et al., *Science,* 242:419-422, 1988.
Sullivan et al., *Mol. Gen. Genet.,* 215(3):431-440, 1989.
Sutcliffe, *Proc. Natl. Acad. Sci. USA,* 75:3737-3741, 1978.
Thillet et al., *J. Biol. Chem.,* 263:12500-12508, 1988.
Thompson et al., *Euphytica,* 85(1-3):75-80, 1995.
Thompson et al., *The EMBO Journal,* 6(9):2519-2523, 1987.
Tian et al., *Plant Cell Rep.,* 16:267-271, 1997.
Tingay et al., *Plant J,* 11(6):1369-1376, 1997.
Tomes et al., *Plant Mol. Biol.,* 14(2):261-268, 1990.
Torbet et al., *Crop Science,* 38(1):226-231, 1998.
Torbet et al., *Plant Cell Reports,* 14(10):635-640, 1995.
Toriyama et al., *Theor Appl. Genet.,* 73:16, 1986.
Tsukada et al., *Plant Cell Physiol.,* 30(4)599-604, 1989.
Twell et al., *Plant Physiol.,* 91:1270-1274, 1989.
Uchimiya et al., *Mol. Gen. Genet.,* 204:204, 1986.
Van den Broeck et al., *Nature,* 313:358, 1985.
Van Eck, Blowers; Earle, *Plant Cell Reports,* 14(5):299-304, 1995.
Vasil et al., *Plant Physiol.,* 91:1575-1579, 1989.
Vasil et al., *Plant Physiol.,* 91:1575-1579, 1989.
Walker et al., *Proc. Natl. Acad. Sci. USA,* 84:6624-6628, 1987.
Wang et al., *Molec. Cell. Biol.,* 12(8):3399-3406, 1992.
Wolk et al., *Proc. Natl. Acad. Sci. USA,* 1561-1565, 1984.
Yamada et al., *Plant Cell Rep.,* 4:85, 1986.
Yamazaki et al., *Biochem. Biophys. Acta,* 1123:18, 1992.
Yang and Russell, *Proc. Natl. Acad. Sci. USA,* 87:41444148, 1990.
Zheng and Edwards, *J. Gen. Virol.,* 71:1865-1868, 1990.
Zhou et al., *Plant Cell Reports,* 12(11):612-616, 1993.
Zukowsky et al., *Proc. Natl. Acad. Sci. USA,* 80:1101-1105, 1983.

---

The invention claimed is:

1. An isolated polynucleotide comprising a nucleic acid sequence that encodes a polypeptide having desaturase activity that desaturates a fatty acid molecule at carbon 15, wherein the polynucleotide is selected from the group consisting of:
   (a) a polynucleotide encoding the polypeptide of SEQ ID NO: 3;
   (b) a polynucleotide comprising the nucleic acid sequence of SEQ ID NO: 1 or SEQ ID NO: 2;
   (c) a polynucleotide with at least 90% identity to SEQ ID NO: 1 or SEQ ID NO: 2; and
   (d) a polynucleotide encoding a polypeptide sequence with at least 90% identity to SEQ ID NO:3.

2. The isolated polynucleotide of claim 1, wherein said polynucleotide is from phyla ascomycota.

3. The isolated polynucleotide of claim 1, wherein the polynucleotide is from *Neurospora crassa*.

4. The isolated polynucleotide of claim 1, wherein the polynucleotide encodes a polypeptide having at least one of the amino acid motifs:

TrpIleLeuAlaHisGluCysGlyHisGlyAlaSerPhe (WILAHECGHGASF) (SEQ ID NO: 6);

LeuAlaHisGluCysGlyHis (LAHECGH) (SEQ ID NO: 7);

HisSerPheLeuLeuValProTyrPheSerTrpLys (HSFLLVPYFSWK) (SEQ ID NO: 8);

LeuLeuValProTyrPheSerTrpLys (LLVPYFSWK) (SEQ ID NO: 9);

His(His/Ala)ArgHisHisArg(Phe/Tyr)ThrThr (H(H/A)RHHR(F/Y)TT) (SEQ ID NO: 10, SEQ ID NO: 19, SEQ ID NO: 20, or SEQ ID NO: 21);

TrpValHisHisTrpLeuValAlaIleThrTyrLeu(His/Gln)HisThrHis (WVHHWLVAITYL(H/Q)HTH) (SEQ ID NO: 11);

AlaIleThrTyrLeu(His/Gln)HisThr (AITYL(H/Q)HT) (SEQ ID NO: 12);

GlyAlaLeuAlaThrValAspArg (GALATVDR) (SEQ ID NO: 13) or

HisValValHisHisLeuPheXaaArgIleProPheTyr (HVVHHLFXCRIPFY) (SEQ ID NO: 14 or SEQ ID NO: 22).

5. The isolated polynucleotide of claim 1, wherein the polynucleotide encodes the polypeptide of SEQ ID NO: 3.

6. The isolated polynucleotide of claim 1, wherein the polynucleotide comprises the nucleic acid sequence of SEQ ID NO: 1 or SEQ ID NO: 2.

7. A recombinant vector comprising the isolated polynucleotide of claim 1.

8. The recombinant vector of claim 7, further comprising at least one additional sequence chosen from the group consisting of:
(a) regulatory sequences operatively linked to the polynucleotide;
(b) selection markers operatively linked to the polynucleotide;
(c) marker sequences operatively linked to the polynucleotide;
(d) a purification moiety operatively linked to the polynucleotide; and
(e) a targeting sequence operatively linked to the polynucleotide.

9. The recombinant vector of claim 7, further defined as comprising a promoter operably linked to said isolated polynucleotide.

10. The recombinant vector of claim 9, wherein the promoter is a developmentally-regulated, organelle-specific, tissue-specific, constitutive or cell-specific promoter.

11. The recombinant vector of claim 9, wherein said promoter is selected from the group consisting of 35S CaMV, 34S FMV, Napin, 7S, Glob, and Lec.

12. The recombinant vector of claim 7, defined as an isolated expression cassette.

13. The recombinant vector of claim 7, further defined as comprising a nucleic acid sequence encoding a polypeptide having desaturase activity that desaturates a fatty acid molecule at carbon 6 and/or a nucleic acid sequence encoding a polypeptide having desaturase activity that desaturates a fatty acid molecule at carbon 12.

14. A transgenic plant transformed with the recombinant vector of claim 7.

15. The transgenic plant of claim 14, further defined as transformed with a nucleic acid sequence encoding a polypeptide having desaturase activity that desaturates a fatty acid molecule at carbon 6.

16. A host cell transformed with the recombinant vector of claim 7.

17. The host cell of claim 16, wherein said host cell expresses a protein encoded by said vector.

18. The host cell of claim 16, wherein the cell has inherited said recombinant vector from a progenitor of the cell.

19. The host cell of claim 16, wherein the cell has been transformed with said recombinant vector.

20. The host cell of claim 16, wherein said host cell is a plant cell.

21. A method of producing seed oil containing omega-3 fatty acids from plant seeds, comprising the steps of:
(a) obtaining seeds of a plant according to claim 14; and
(b) extracting the oil from said seeds.

22. A method of producing a plant comprising seed oil containing, altered levels of omega-3 fatty acids comprising introducing the recombinant vector of claim 7 into an oil-producing plant.

23. The method of claim 22, wherein introducing the recombinant vector comprises plant breeding.

24. The method of claim 22, wherein introducing the recombinant vector comprises the steps of:
(a) transforming a plant cell with said recombinant vector; and
(b) regenerating said plant from the plant cell, wherein the plant has altered levels of omega-3 fatty acids.

25. The method of claim 22, wherein the plant is a plant selected from the group consisting of: *Arabidopsis thaliana*, oilseed *Brassica*, rapeseed, sunflower, safflower, canola, corn, soybean, cotton, flax, jojoba, Chinese tallow tree, tobacco, cocoa, peanut, fruit plants, citrus plants, and plants producing nuts and berries.

26. The method of claim 22, wherein the plant is further defined as transformed with a nucleic acid sequence encoding a polypeptide having desaturase activity that desaturates a fatty acid molecule at carbon 6.

27. The method of claim 26, wherein stearidonic acid is increased.

28. The method of claim 22, further defined as comprising introducing said recombinant vector into a plurality of oil-producing plants and screening said plants or progeny thereof having inherited the recombinant vector for a plant having a desired profile of omega-3 fatty acids.

29. The isolated polynucleotide of claim 1, comprising a polynucleotide with at least 90% identity to SEQ ID NO: 1 or SEQ ID NO: 2.

30. The isolated polynucleotide of claim 1, comprising a polynucleotide with at least 95% identity to SEQ ID NO: 1 or SEQ ID NO: 2.

31. The isolated polynucleotide of claim 1, encoding a polypeptide sequence with at least 90% identity to SEQ ID NO:3.

32. The isolated polynucleotide of claim 1, encoding a polypeptide sequence with at least 95% identity to SEQ ID NO:3.

* * * * *

UNITED STATES PATENT AND TRADEMARK OFFICE
CERTIFICATE OF CORRECTION

PATENT NO. : 7,622,632 B2
APPLICATION NO. : 10/515283
DATED : November 24, 2009
INVENTOR(S) : Ursin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 837 days.

Signed and Sealed this

Twenty-sixth Day of October, 2010

David J. Kappos
*Director of the United States Patent and Trademark Office*